(12) United States Patent
Todd et al.

(10) Patent No.: US 9,506,108 B2
(45) Date of Patent: Nov. 29, 2016

(54) NUCLEIC ACID ENZYME SUBSTRATES

(75) Inventors: Alison Velyian Todd, Glebe (AU);
Elisa Mokany, Caringbah (AU);
Evelyn Meiria Linardy, Woodcroft
(AU); Dina Lonergan, Coogee (AU)

(73) Assignee: SPEEDX PTY LTD (AU)

( * ) Notice: Subject to any disclaimer, the term of this patent is extended or adjusted under 35 U.S.C. 154(b) by 201 days.

(21) Appl. No.: 14/343,840

(22) PCT Filed: Sep. 10, 2012

(86) PCT No.: PCT/AU2012/001081
§ 371 (c)(1),
(2), (4) Date: Aug. 23, 2014

(87) PCT Pub. No.: WO2013/033792
PCT Pub. Date: Mar. 14, 2013

(65) Prior Publication Data
US 2015/0050656 A1 Feb. 19, 2015

(30) Foreign Application Priority Data

Sep. 9, 2011 (AU) ................................ 2011903686

(51) Int. Cl.
*C12Q 1/68* (2006.01)
*C12N 15/11* (2006.01)

(52) U.S. Cl.
CPC ........... *C12Q 1/6818* (2013.01); *C12Q 1/6823* (2013.01); *C12N 15/111* (2013.01); *C12N 2310/12* (2013.01); *C12N 2310/53* (2013.01); *C12N 2320/11* (2013.01)

(58) Field of Classification Search
None
See application file for complete search history.

(56) References Cited

U.S. PATENT DOCUMENTS

2004/0077565 A1 4/2004 Pavco et al.
2007/0231810 A1* 10/2007 Todd .................... C12N 15/111
435/6.18
2010/0136536 A1 6/2010 Todd et al.

FOREIGN PATENT DOCUMENTS

| EP | 2385141 A1 | 9/2011 | |
|---|---|---|---|
| WO | WO 2008040095 A1 * | 4/2008 | ........... C12Q 1/6818 |
| WO | WO 2013/123552 A1 | 8/2013 | |
| WO | WO 2013/188912 A1 | 12/2013 | |

OTHER PUBLICATIONS

EPO Application No. 12830774.1 (Published as EP2753717), Supplementary European Search Report and European Search Opinion, mailed May 27, 2015.
WIPO Application No. PCT/AU2012/001081, International Search Report and Written Opinion of the International Searching Authority, mailed Nov. 7, 2012.
Mokany, et al., "MNAzymes, a Versatile New Class of Nucleic Acid Enzymes That Can Function as Biosensors and Molecular Switches," J. Am. Chem. Soc., 132:1051-1059, (2010).
WIPO Application No. PCT/AU2012/001081, International Preliminary Report on Patentability, issued Dec. 12, 2013.

* cited by examiner

*Primary Examiner* — Aaron Priest
(74) *Attorney, Agent, or Firm* — Alston & Bird LLP

(57) ABSTRACT

The invention relates to nucleic acid substrates for catalytic nucleic acid enzymes and methods utilizing the substrates.

15 Claims, 13 Drawing Sheets

(i)

(ii)

(iii)
a

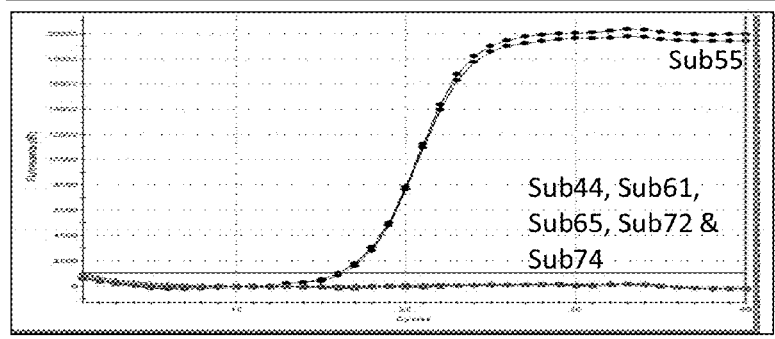

| Sub44 | C A G G T C T C C T C g u C C C T A T A G T G A | SEQ ID NO: 25 |
| Sub72 | A T C A C G C C T C g u C T C C T C C C A G | SEQ ID NO: 75 |
| Sub74 | A T C A C T C C C C g u C C C C T C C C A G | SEQ ID NO: 77 |
| Sub61 | C T C G A C C C C g u C T C C A C G G C A | SEQ ID NO: 73 |
| Sub65 | T C T C G A C C T C g u C T C C A C G G C A | SEQ ID NO: 74 |
| Sub55 | A C C G C A C C T C g u C C C C A G C T C | SEQ ID NO: 29 | b

Sub55

Sub44, Sub61, Sub65, Sub72 & Sub74

(iv)
a

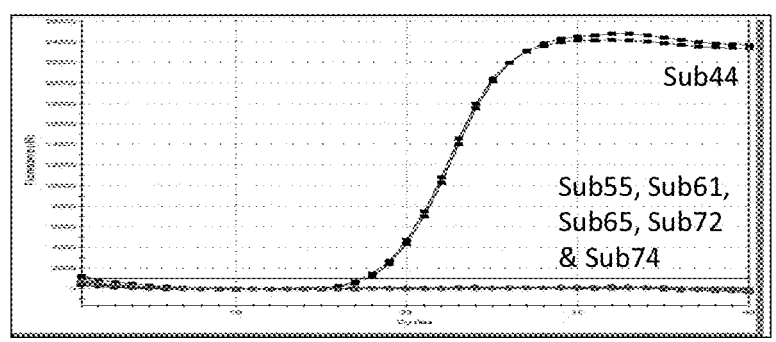

| Sub55 | A C G G C A C C T C g u C C C C A G C T C | SEQ ID NO: 29 |
| Sub61 | C T C G A C C C C g u C T C C A G G G C A | SEQ ID NO: 73 |
| Sub65 | T C T C G A C C T C g u C T C C A C G G C A | SEQ ID NO: 74 |
| Sub72 | A T C A C G C C T C g u C T C C T C C C A G | SEQ ID NO: 75 |
| Sub74 | A T C A C T C C C C g u C C C C T C C C A G | SEQ ID NO: 77 |
| Sub44 | C A G G T C T C C T C g u C C C T A T A G T G A | SEQ ID NO: 75 | b

Sub44

Sub55, Sub61, Sub65, Sub72 & Sub74

FIGURE 9 (Cont)

NUCLEIC ACID ENZYME SUBSTRATES

CROSS-REFERENCE TO RELATED APPLICATIONS

The present application is a US national stage of PCT/AU2012/001081 filed Sep. 10, 2012, which claims the benefit of Australian Provisional Application No. 2011903686 filed Sep. 9, 2011, the entire content of which is incorporated herein by cross-reference.

REFERENCE TO A SEQUENCE LISTING

This application includes an electronic sequence listing in a file named "443217SEQLIST2.txt", created Oct. 21, 2014, and containing 43 kilobytes, which is incorporated by reference.

TECHNICAL FIELD

The invention relates generally to the field of nucleic acid enzymes. More specifically, the invention relates to substrates for nucleic acid enzymes and methods utilising the substrates.

BACKGROUND OF THE INVENTION

A wide variety of nucleic acid molecules with enzymatic or catalytic activity have been discovered in the last 20 years. RNA enzymes ("ribozymes") occur in nature but can be engineered to specifically recognize and modify a target RNA substrate. In vitro evolution techniques have facilitated the discovery and development of many more catalytic nucleic acids, including deoxyribonucleic acids often referred to as "deoxyribozymes", "DNA enzymes" or "DNAzymes". In vitro evolved DNAzymes and/or ribozymes have been discovered which have the capacity to catalyse a broad range of reactions including cleavage of nucleic acids, ligation of nucleic acids, porphyrin metallation, and formation of carbon-carbon bonds, ester bonds or amide bonds.

In particular, DNAzymes and ribozymes have been characterized which specifically cleave distinct nucleic acid sequences after hybridizing via Watson Crick base pairing. DNAzymes are capable of cleaving either RNA or DNA molecules. Ribozymes are also able to cleave both RNA and DNA target sequences. The "10-23" and "8-17" DNAzymes are capable of cleaving nucleic acid substrates at specific RNA phosphodiester bonds to create reaction products which have 2',3'-cyclic phosphate and 5'-hydroxyl groups. Examples of deoxyribozymes (DNAzymes), which can ligate 2',3'-cyclic phosphate and 5'-hydroxyl products include the "7Z81" and "7Z48" ligases.

More recently, Multi-component Nucleic Acid enzymes (MNAzymes) have been described which have the capacity to self-assemble from two or more oligonucleotide components (also referred to herein as "partzymes") in the presence of a MNAzyme assembly facilitator (e.g. a target molecule to be detected).

The versatile nature of catalytic nucleic acids has facilitated their use in many different applications. A key element to the successful use of catalytic nucleic acids is their capacity to modify an appropriate substrate. In general, the substrate is substantially complementary to the hybridizing arms of the catalytic nucleic acid and contains a specific sequence or sequence motif at the site of catalytic action. The nature of the interaction between a given catalytic nucleic acid and its substrate is determinative of how efficiently the enzyme engages and/or catalytically modifies its substrate, and is thus a fundamental consideration in designing any system that utilises catalytic nucleic acids.

Catalytic nucleic acids have in vitro diagnostic applications in the detection of nucleic acids, proteins and small molecules. These applications often involve amplification of either the target or the signal to generate sufficient signal for robust detection of the analyte of interest.

Methods that employ catalytic nucleic acids require substrates that are modified with a sufficient rate of catalytic activity to allow effective discrimination over background noise. Different methods may require the use of different reaction temperatures and so there is a necessity for substrates that are efficiently modified (e.g. cleaved) at the required temperatures. Methods such as those utilizing MNAzymes and DNAzymes permit multiplexed analysis of many targets simultaneously in a single reaction, but the ability to multiplex and distinguish between the multiple targets is dependent on the existence of a suitable range of substrates, usually at least one per target. The number of substrates known in the art that are modified (e.g. cleaved) with high efficiency is currently insufficient for mass multiplexing.

The DNAzyme and MNAzyme substrates previously known in the art were derived by screening multiple possible substrates to empirically determine those that were cleaved most efficiently. Often this screening was performed using large numbers of DNAzymes targeted to cleave theoretically possible cleavage sites within full length mRNA. This screening was usually performed under physiological conditions (temperature and ionic strength, composition and pH of buffers). This bias towards finding efficiently cleaved sequences of mRNA at physiological conditions exists because such studies were focused on therapeutic uses of DNAzymes as inhibitors of RNA expression in vivo. Such studies provide a range of laborious protocols for empirical measurement of a large number of putative substrates to find the few that are cleaved efficiently (see for example Cairns et al., 1999 Nat Biotech 17:480-486). These studies resulted in a limited set of design guidelines for the selection of efficiently cleaved substrates, and in many cases the guidelines focused on the design of the DNAzyme rather than the substrate as the DNAzyme can be easily adjusted and the mRNA cannot. One common guideline generated from these studies is that the exact sequence of the R-Y ribonucleotide motif at the cleavage site of the substrate is important with cleavage efficiency being in the following order: GU≥AU>GC>>>AC.

The efficiency of cleavage of a full length mRNA under in vitro conditions is not an absolute measure of the cleavage efficiency in a cellular environment as the latter includes ribonuclear proteins, and other confounding factors that cannot be easily mimicked in vitro.

The design guidelines generated in the past have some use in selection of sites within a long mRNA molecule that may be efficiently cleaved by DNAzymes and MNAzymes under physiological conditions, but have limited ability to predict which substrates will be cleaved with sufficient efficiency for utility in in vitro diagnostic applications. In vitro diagnostic applications may require conditions very different from the physiological conditions generally screened and used to establish the limited substrate design guidelines that exist in the art.

There is a need for a set of guidelines, or sequence motifs, for substrate sequences that predict with greater certainty if a substrate will be efficiently cleaved by a MNAzyme or DNAzyme in conditions suitable for in vitro diagnostic applications. There is also a need for catalytic nucleic acid substrates with properties that facilitate improved catalytic nucleic acid function. These properties may include, for example, an ability to facilitate improved catalytic nucleic acid function over a range of conditions and/or a capacity to extend the number of targets that can be simultaneously detected in a multiplex reaction.

SUMMARY OF THE INVENTION

While many have attempted to establish a sequence motif or set of design guidelines which consistently produces efficient substrate sequences, to date no effective sequence or set of guidelines has been identified. The present invention provides a series of principles which has facilitated the development of new efficiently cleaved substrates. The present invention thus provides catalytic nucleic acid enzyme substrates with properties that enhance catalytic nucleic acid function thereby addressing a need existing in the art.

In a first aspect, the present invention provides an isolated polynucleotide substrate for a catalytic nucleic acid enzyme, said polynucleotide substrate comprising a sequence $N_1$-$N_2$-$N_3$-$N_4$-$N_6$-$N_7$-$N_8$-rR-rY-$N_9$-$N_{10}$-$N_{11}$-$N_{12}$-$N_{13}$-$N_{14}$-$N_{15}$ wherein:

rR is a purine ribonucleotide;
rY is a pyrimidine ribonucleotide;
each of $N_1$-$N_{15}$ are nucleotides;
six or more of $N_5$-$N_{13}$ are cytosine nucleotides; and
less than three of $N_9$-$N_{15}$ are guanine nucleotides.

In one embodiment of the first aspect, the polynucleotide substrate comprises or consists of a sequence defined by any one of SEQ ID NOs: 25-27, 29-30, 33, 72-90, or 172-175.

In one embodiment of the first aspect, seven or more, or eight or more of $N_5$-$N_{13}$ are cytosine nucleotides.

In one embodiment of the first aspect, seven or more of $N_5$-$N_{13}$ are cytosine nucleotides and the polynucleotide substrate comprises or consists of a sequence defined by any one of SEQ ID NOs: 29, 73, 76-80, 82-83, 85-90, or 172-175.

In one embodiment of the first aspect, eight of $N_5$-$N_{13}$ are cytosine nucleotides and the polynucleotide substrate comprises or consists of a sequence defined by any one of SEQ ID NOs: 76, 77, 80, 83 or 87.

In one embodiment of the first aspect, seven or more, or eight or more of $N_4$-$N_{13}$ are cytosine nucleotides.

In one embodiment of the first aspect, seven or more of $N_4$-$N_{13}$ are cytosine nucleotides and the polynucleotide substrate comprises of a sequence defined by any one of SEQ ID NOs: 27, 29, 73, 76-83, 85-90, or 172-175.

In one embodiment of the first aspect, eight of $N_4$-$N_{13}$ are cytosine nucleotides and the polynucleotide substrate comprises or consists of a sequence defined by any one of SEQ ID NOs: 76, 77, 79-80, 82-83, 87, 88 or 90.

In one embodiment of the first aspect, six or more, seven or more, or eight or more of $N_4$-$N_{12}$ are cytosine nucleotides.

In one embodiment of the first aspect, seven or more of $N_4$-$N_{12}$ are cytosine nucleotides and the polynucleotide substrate comprises or consists of a sequence defined by any one of SEQ ID NOs: 27, 29, 73, 76, 77, 79-83, 85-88, 90 or 172-175.

In one embodiment of the first aspect, eight of $N_4$-$N_{12}$ are cytosine nucleotides and the polynucleotide substrate comprises or consists of a sequence defined by any one of SEQ ID NOs: 76, 77, 80, 83, 87, or 88.

In one embodiment of the first aspect, six or more, seven or more, or eight or more of $N_5$-$N_{12}$ are cytosine nucleotides.

In one embodiment of the first aspect, seven or more of $N_5$-$N_{12}$ are cytosine nucleotides and the polynucleotide substrate comprises or consists of a sequence defined by any one of SEQ ID NOs: 29, 73, 76, 77, 80, 83, 85-88 or 172-175.

In one embodiment of the first aspect, eight of $N_5$-$N_{12}$ are cytosine nucleotides and the polynucleotide substrate comprises or consists of a sequence defined by any one of SEQ ID NOs: 76, 77, 80, 83, or 87.

In one embodiment of the first aspect, any one or more of $N_1$, $N_2$, $N_8$ and/or $N_9$ is a cytosine nucleotide.

In one embodiment of the first aspect, $N_8$ and $N_9$ are cytosine nucleotides, and the polynucleotide substrate comprises or consists of a sequence defined by any one of SEQ ID NOs: 25-26, 29-30, 72-90, or 172-175.

In one embodiment of the first aspect, two, one or none of $N_9$-$N_{15}$ are guanine nucleotides.

In one embodiment of the first aspect, one or none of $N_9$-$N_{15}$ are guanine nucleotides and the polynucleotide substrate comprises or consists of a sequence defined by any one of SEQ ID NOs: 25-27, 29-30, 33, 72-80, 82-90, or 172-175.

In one embodiment of the first aspect, none of $N_9$-$N_{15}$ are guanine nucleotides and the polynucleotide substrate comprises or consists of a sequence defined by any one of SEQ ID NOs: 25, 26, 30, 33, 72, 75, 77-80, 84-85, or 89.

In one embodiment of the first aspect, more than ten, more than eleven, more than twelve, or more than thirteen of $N_1$-$N_{15}$ are pyrimidine nucleotides.

In one embodiment of the first aspect, eleven, twelve, or more than twelve of $N_1$-$N_{15}$ are pyrimidine nucleotides and the polynucleotide substrate comprises or consists of a sequence defined by any one SEQ ID NOs: 25-27, 29, 33, 73-90 or 173-175.

In one embodiment of the first aspect, thirteen or fourteen of $N_1$-$N_{15}$ are pyrimidine nucleotides and the polynucleotide substrate comprises or consists of a sequence defined by any one SEQ ID NOs: 75, 77-80, 82-85 or 88-89.

In one embodiment of the first aspect, more than eight, more than nine, more than ten, or eleven of $N_1$-$N_{14}$ are cytosine nucleotides.

In one embodiment of the first aspect, ten or eleven of $N_1$-$N_{14}$ are cytosine nucleotides and the polynucleotide substrate comprises or consists of a sequence defined by any one SEQ ID NOs: 33, 76-80, 82-83, 85, 87, 88, or 89.

In one embodiment of the first aspect, eleven of $N_1$-$N_{14}$ are cytosine nucleotides and the polynucleotide substrate comprises or consists of a sequence defined by any one SEQ ID NOs: 77-79.

In one embodiment of the first aspect, the polynucleotide substrate further comprises a detectable label for detecting the polynucleotide substrate.

In one embodiment of the first aspect, the polynucleotide substrate further comprising a detectable portion and a quencher portion, wherein a detectable effect provided by the detectable portion is increased or decreased upon modification of the polynucleotide substrate by said catalytic nucleic acid enzyme.

In one embodiment of the first aspect, the purine ribonucleotide comprises guanine.

In one embodiment of the first aspect, the pyrimidine ribonucleotide comprises uracil.

In one embodiment of the first aspect, a portion of the polynucleotide substrate that binds to said catalytic nucleic acid enzyme has a melting temperature (Tm) of between 50° C. and 90° C., between 50° C. and 65° C., between 50° C.

and 60° C., between 52° C. and 58° C., between 66° C. and 76° C., between 68° C. and 76° C., between 64° C. and 70° C., between 70° C. and 76° C., between 70° C. and 75° C., between 72° C. and 76° C., 52° C., 58° C., 64° C., 66° C., 68° C., 70° C., 72° C., or 76° C.

In one embodiment of the first aspect, the catalytic nucleic acid enzyme is:
(i) a multi-component nucleic acid enzyme (MNAzyme) and said portion binds to at least one substrate arm of said MNAzyme; or
(ii) a DNAzyme.

In one embodiment of the first aspect, the polynucleotide substrate is capable of catalytic modification by an MNAzyme.

In one embodiment of the first aspect, the polynucleotide substrate is capable of catalytic modification by a DNAzyme.

In one embodiment of the first aspect, the polynucleotide substrate comprises a detectable label for detection by fluorescence spectroscopy, surface plasmon resonance, mass spectroscopy, NMR, electron spin resonance, polarization fluorescence spectroscopy, circular dichroism, immunoassay, chromatography, radiometry, electrochemical, photometry, scintigraphy, electronic methods, UV, visible light or infra-red spectroscopy, enzymatic methods, or any combination thereof.

In one embodiment of the first aspect, the polynucleotide substrate comprises a detectable label for detection by fluorescence spectroscopy.

In one embodiment of the first aspect, the polynucleotide substrate comprises a detectable label for detection by Fluorescence Resonance Energy Transfer (FRET) spectroscopy.

In a second aspect, the present invention provides an isolated polynucleotide substrate for a catalytic nucleic acid enzyme, said polynucleotide substrate comprising or consisting of a sequence defined by SEQ ID NO: 28.

In one embodiment of the second aspect, the catalytic nucleic acid enzyme is an MNAzyme comprising a pair of oligonucleotide partzymes, said pair comprising or consisting of SEQ ID NOs: 15 and 8, SEQ ID NOs: 93 and 94, or SEQ ID NOs: 114 and 115.

In one embodiment of the second aspect, the catalytic nucleic acid enzyme is a DNAzyme comprising or consisting of a sequence defined by SEQ ID NO: 138.

In a third aspect, the present invention provides a method for detecting the presence of at least one target comprising:
(a) providing two or more oligonucleotide partzymes, wherein at least a first oligonucleotide partzyme and a second oligonucleotide partzyme self-assemble in the presence of said target to form at least a first catalytically active multi-component nucleic acid enzyme (MNAzyme);
(b) providing the isolated polynucleotide substrate of the first or second aspect, wherein said polynucleotide substrate is capable of being modified by said first MNAzyme, wherein said modification of said polynucleotide substrate by said MNAzyme provides a detectable effect;
(c) contacting said two or more oligonucleotide partzymes with a sample putatively containing said target under conditions permitting:
(1) the self-assembly of said at least first MNAzyme, and
(2) the catalytic activity of said at least first MNAzyme; and
(d) detecting said detectable effect.

In one embodiment of the third aspect, the target is an MNAzyme assembly facilitator.

In one embodiment of the third aspect, the target is a nucleic acid.

In one embodiment of the third aspect, the target is a nucleic acid that hybridizes to one or more sensor arms of said MNAzyme by base pair complementarity.

In one embodiment of the third aspect, the nucleic acid is selected from the group consisting of DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof.

In one embodiment of the third aspect, the nucleic acid is amplified.

In one embodiment of the third aspect, the amplification comprises one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

In one embodiment of the third aspect, the polynucleotide substrate hybridises with substrate arms of said MNAzyme at a temperature of between 50° C. and 90° C., between 50° C. and 65° C., between 50° C. and 60° C., between 52° C. and 58° C., between 66° C. and 76° C., between 68° C. and 76° C., between 64° C. and 70° C., between 70° C. and 76° C., between 70° C. and 75° C., between 72° C. and 76° C., 52° C., 58° C., 64° C., 66° C., 68° C., 70° C., 72° C., or 76° C.

In one embodiment of the third aspect, the method further comprises providing:
(a) two or more additional oligonucleotide partzymes capable of self-assembling in the presence of a different target to form a second catalytically active MNAzyme; and
(b) at least one additional polynucleotide substrate;
wherein said additional polynucleotide substrate is capable of being modified by said second MNAzyme in the presence of said different target.

In one embodiment of the third aspect, the additional polynucleotide substrate is not capable of being modified by said first MNAzyme.

In one embodiment of the third aspect, the detecting in part (d) comprises use of fluorescence spectroscopy, surface plasmon resonance, mass spectroscopy, NMR, electron spin resonance, polarization fluorescence spectroscopy, circular dichroism, immunoassay, chromatography, radiometry, electrochemical, photometry, scintigraphy, electronic methods, UV, visible light or infra-red spectroscopy, enzymatic methods, or any combination thereof.

In one embodiment of the third aspect, the detecting in part (d) comprises use of fluorescence spectroscopy.

In one embodiment of the third aspect, the detecting in part (d) comprises detection of a FRET detectable effect.

In one embodiment of the third aspect, the catalytic core of said MNAzyme comprises DNA or an analogue thereof.

In a fourth aspect, the present invention provides use of the isolated polynucleotide substrate of the first or second aspect as a substrate for a catalytic nucleic acid enzyme.

In one embodiment of the fourth aspect, the catalytic nucleic acid enzyme is a multi-component nucleic acid enzyme (MNAzyme),
said MNAzyme comprising at least two or more oligonucleotide partzymes wherein at least a first oligonucleotide partzyme and a second oligonucleotide partzyme self-assemble in the presence of an MNAzyme assembly facilitator to form a catalytically active multi-component nucleic acid enzyme (MNAzyme), wherein each of said at least first and said second oligonucleotide partzymes comprise a substrate arm portion, a catalytic core portion, and a sensor arm portion;

wherein upon self-assembly, the sensor arm portion of said first and second oligonucleotide partzymes act as sensor arms of the MNAzyme, the substrate arm portion of the first and second oligonucleotide partzymes act as substrate arms of the MNAzyme, and the catalytic core portion of the first and second oligonucleotide partzymes act as a catalytic core of the MNAzyme;

and wherein the sensor arms of the MNAzyme interact with said MNAzyme assembly facilitator so as to maintain the first and second oligonucleotide partzymes in proximity for association of their respective catalytic core portions to form the catalytic core of the MNAzyme, said catalytic core capable of modifying said polynucleotide substrate, and wherein said substrate arms of said MNAzyme engage said polynucleotide substrate so that said catalytic core of said MNAzyme can modify said polynucleotide substrate.

In one embodiment of the third or fourth aspect, the catalytic core portion of each said oligonucleotide partzyme comprises DNA or an analogue thereof.

In one embodiment of the fourth aspect, the assembly facilitator is a target to be identified, detected or quantitated.

In one embodiment of the third or fourth aspect, the first and second oligonucleotide partzymes comprise respective sequences defined by:

SEQ ID NO: 9 and SEQ ID NO: 10; SEQ ID NO: 11 and SEQ ID NO: 12; SEQ ID NO: 13 and SEQ ID NO: 14; SEQ ID NO: 16 and SEQ ID NO: 14; SEQ ID NO: 17 and SEQ ID NO: 18; SEQ ID NO: 40 and SEQ ID NO: 41; SEQ ID NO: 42 and SEQ ID NO: 43; SEQ ID NO: 44 and SEQ ID NO: 45; SEQ ID NO: 46 and SEQ ID NO: 45; SEQ ID NO: 47 and SEQ ID NO: 63; SEQ ID NO: 48 and SEQ ID NO: 49; SEQ ID NO: 50 and SEQ ID NO: 51; SEQ ID NO: 52 and SEQ ID NO: 51; SEQ ID NO: 38 and SEQ ID NO: 55; SEQ ID NO: 56 and SEQ ID NO: 57; SEQ ID NO: 58 and SEQ ID NO: 59; SEQ ID NO: 60 and SEQ ID NO: 61; SEQ ID NO: 62 and SEQ ID NO: 63; SEQ ID NO: 64 and SEQ ID NO: 65; SEQ ID NO: 66 and SEQ ID NO: 67; SEQ ID NO: 62 and SEQ ID NO: 68; SEQ ID NO: 69 and SEQ ID NO: 70; SEQ ID NO: 46 and SEQ ID NO: 55; SEQ ID NO: 46 and SEQ ID NO: 59; SEQ ID NO: 38 and SEQ ID NO: 45; SEQ ID NO: 58 and SEQ ID NO: 45; SEQ ID NO: 62 and SEQ ID NO: 45; SEQ ID NO: 46 and SEQ ID NO: 63; SEQ ID NO: 71 and SEQ ID NO: 68; SEQ ID NO: 98 and SEQ ID NO: 99; SEQ ID NO: 100 and SEQ ID NO: 103; SEQ ID NO: 104 and SEQ ID NO: 105; SEQ ID NO: 106 and SEQ ID NO: 107; SEQ ID NO: 108 and SEQ ID NO: 109; SEQ ID NO: 110 and SEQ ID NO: 111; SEQ ID NO: 112 and SEQ ID NO: 113; SEQ ID NO: 116 and SEQ ID NO: 117; SEQ ID NO: 118 and SEQ ID NO: 119; SEQ ID NO: 120 and SEQ ID NO: 121; SEQ ID NO: 122 and SEQ ID NO: 119; SEQ ID NO: 155 and SEQ ID NO: 156; SEQ ID NO: 157 and SEQ ID NO: 158; SEQ ID NO: 159 and SEQ ID NO: 160; SEQ ID NO: 168 and SEQ ID NO: 169; SEQ ID NO: 179 and SEQ ID NO: 180; SEQ ID NO: 181 and SEQ ID NO: 182; SEQ ID NO: 183 and SEQ ID NO: 184 or SEQ ID NO: 185 and SEQ ID NO: 186.

In one embodiment of the third or fourth aspect, said oligonucleotide substrate and said first and second oligonucleotide partzymes are defined by a combination of sequences as set forth in Table 6, 8, 10, 13, 16, 20, 22 and/or 24.

In one embodiment of the fourth aspect, the catalytic nucleic acid enzyme is a DNAzyme, and the DNAzyme and oligonucleotide substrate are defined by a combination of sequences as set forth in Table 15.

In one embodiment of the fourth aspect, the target is a nucleic acid that hybridizes to one or more sensor arms of said MNAzyme by base pair complementarity.

In one embodiment of the fourth aspect, the polynucleotide substrate hybridises with said catalytic nucleic acid enzyme at a temperature of between 50° C. and 90° C., between 50° C. and 65° C., between 50° C. and 60° C., between 52° C. and 58° C., between 66° C. and 76° C., between 68° C. and 76° C., between 64° C. and 70° C., between 70° C. and 76° C., between 70° C. and 75° C., between 72° C. and 76° C., 52° C., 58° C., 64° C., 66° C., 68° C., 70° C., 72° C., or 76° C.

In a fifth aspect, the present invention provides a kit comprising the isolated polynucleotide substrate of the first or second aspect.

In one embodiment of the fifth aspect, the kit further comprises a catalytic nucleic acid enzyme capable of catalytically modifying said polynucleotide substrate.

In one embodiment of the fifth aspect, the catalytic nucleic acid enzyme is a multi-component nucleic acid enzyme (MNAzyme).

In a sixth aspect, the present invention provides a kit comprising the isolated polynucleotide substrate of the first or second aspect and a plurality of oligonucleotide partzymes designed to assemble a multi-component nucleic acid enzyme (MNAzyme) capable of detecting at least one target, wherein said MNAzyme is capable of catalytically modifying the polynucleotide substrate.

In one embodiment of sixth aspect, said oligonucleotide substrate and said plurality of oligonucleotide partzymes are defined by a combination of sequences as set forth in Table 6, 8, 10, 13, 16, 20, 22 and/or 24.

In a seventh aspect, the present invention provides an assembly comprising a solid support bound to a polynucleotide substrate of the first or second aspect.

In one embodiment of the first or third to seventh aspects, any one or more of $N_1$-$N_{15}$ are deoxyribonucleotides.

In one embodiment of the first or third to seventh aspects, any one or more of $N_1$-$N_{15}$ are ribonucleotides.

In one embodiment of the first or third to seventh aspects, all of $N_1$-$N_{15}$ are deoxyribonucleotides.

In one embodiment of the first or third to seventh aspects, all of $N_1$-$N_{15}$ are ribonucleotides.

In one embodiment of the first or third to seventh aspects, $N_1$-$N_{15}$ comprises a mixture of deoxyribonucleotides and ribonucleotides.

In one embodiment of the seventh aspect, the assembly comprises a plurality of different solid supports bound to a plurality of different polynucleotide substrates.

In one embodiment of the first, second, fourth, or fifth aspect, the catalytic nucleic acid enzyme is a DNAzyme.

In one embodiment of the first, second, fourth, or fifth aspect, the catalytic nucleic acid enzyme is a ribozyme.

In one embodiment of the first, second, fourth, or fifth aspect, the catalytic nucleic acid enzyme is a multi-component nucleic acid enzyme (MNAzyme).

In one embodiment of the above aspects, the catalytic nucleic acid enzyme is capable of modifying the polynucleotide substrate by cleavage.

In one embodiment of the first, second, or fifth aspect, the catalytic nucleic acid enzyme is an MNAzyme comprising first and second oligonucleotide partzymes, and said oligonucleotide substrate and said first and second oligonucleotide partzymes are defined by a combination of sequences as set forth in Table 6, 8, 10, 13, 16, 20, 22 and/or 24.

In one embodiment of the first, second, or fifth aspect, the catalytic nucleic acid enzyme is a DNAzyme, and the DNAzyme and oligonucleotide substrate are defined by a combination of sequences as set forth in Table 15.

In one embodiment of the first, second, or fifth aspect, the polynucleotide substrate is capable of hybridising to said catalytic nucleic acid enzyme by complementary base pairing.

In one embodiment of the fourth aspect, the polynucleotide substrate hybridises to said catalytic nucleic acid enzyme by complementary base pairing.

In one embodiment of the third and fourth aspect, the polynucleotide substrate hybridises to said MNAzyme by complementary base pairing.

In one embodiment of the first, second, fifth, and sixth aspect, the polynucleotide substrate the polynucleotide substrate is capable of hybridising to said MNAzyme by complementary base pairing.

In one embodiment of the above aspects, a portion of the isolated polynucleotide substrate binds to at least one substrate arm of said MNAzyme.

In one embodiment of the above aspects, the polynucleotide substrate is a universal substrate capable of being bound and catalytically modified by more than one different type of catalytic nucleic acid enzyme.

In one embodiment of the above aspects, the polynucleotide substrate is a universal substrate capable of being bound and catalytically modified by more than one different type of multi-component nucleic acid enzyme (MNAzyme).

In one embodiment of the above aspects, at least one of said oligonucleotide partzymes, assembly facilitator or substrate comprises DNA or an analogue thereof.

In one embodiment of the third and sixth aspect, the modifying is cleavage of the polynucleotide substrate by the MNAzyme.

BRIEF DESCRIPTION OF THE FIGURES

Preferred embodiments of the present invention will now be described, by way of example only, with reference to the accompanying figures wherein:

In FIG. 6 (i) the different columns of data refer to results for different reaction temperatures (as indicated in the legend 52° C., 54° C., 56° C. and 58° C.). FIG. 6 (i) illustrates the signal to noise ratio on the y-axis. FIG. 6 (ii) illustrates the standard deviation of the average of the signal to noise ratio from all four temperatures tested and the different series of substrates are indicated by different shading of columns.

In FIG. 8 (i) the different columns of data refer to results for different reaction temperatures (as indicated in the legend—50° C. to 60° C.) with the signal to noise ratio on the y-axis. In FIG. 8 (ii) the columns of data refer to the standard deviation of the average of the signal to noise ratio from all six temperatures tested and the different series of substrates are indicated by different shading of columns.

DEFINITIONS

Figure 1:
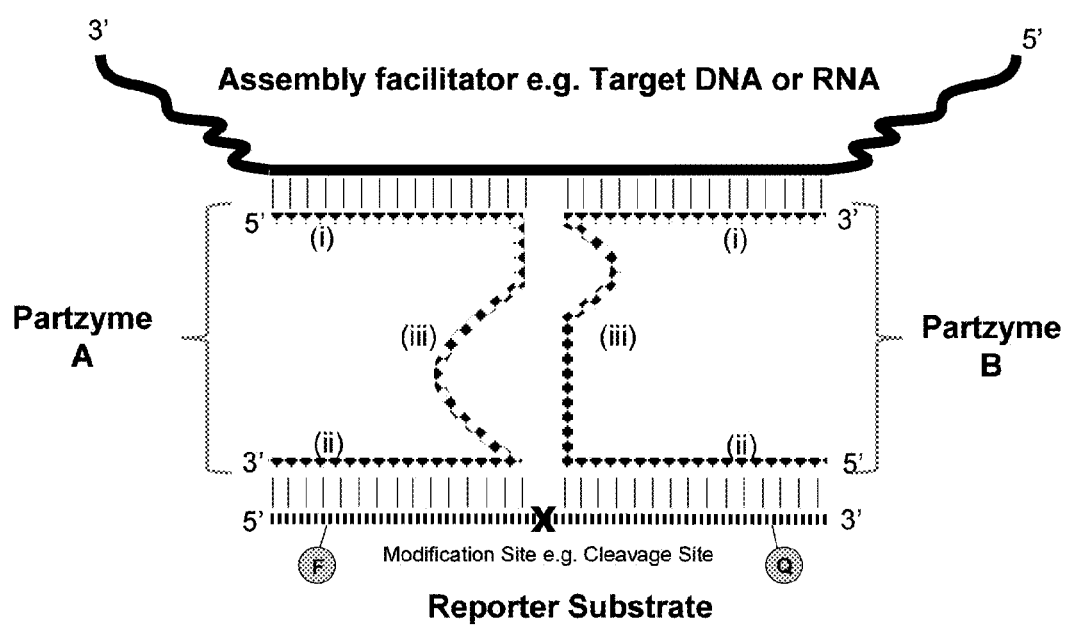
FIG. 1 is a diagram depicting an exemplary design of a Multi-component nucleic acid (MNAzyme). By way of exemplary disclosure, a MNAzyme is comprised of two oligonucleotide components (partzyme A and partzyme B), which self assemble in the presence of an assembly facilitator. When the two partzymes assemble in the presence of the assembly facilitator, a catalytically active MNAzyme forms which is capable of modifying (e.g. cleaving or ligating) a substrate. The two component partzymes have (i) sensor arms, which bind to the assembly facilitator, (ii) substrate arms, which bind the substrate, and (iii) partial catalytic core sequences. The presence of an assembly facilitator molecule (e.g. a target nucleic acid sequence) provides the "input" signal which directs the assembly of partzyme components in a highly specific fashion which is amenable to modulation. In some embodiments, the assembly facilitator may be, for example, a target nucleic acid sequence present in a test sample. In other embodiments, the assembly facilitator may be, for example a synthetic oligonucleotide included in the milieu to direct the self-assembly of the partzyme components in the presence of a detectable entity or event. Modification of the substrate by the assembled MNAzyme can provide a "detectable effect" which may be detected and/or quantified. For example, when the substrate is dual labelled with a fluorophore (F) and a quencher (Q), cleavage of this "reporter substrate" by an active MNAzyme separates the fluorophore and the quencher resulting in a concomitant increase in fluorescence.

Certain terms are used herein which shall have the meanings set forth as follows.

As used herein, the singular form "a", "an" and "the" include plural references unless the context clearly dictates otherwise. For example, the term "a polynucleotide substrate" also includes a plurality of polynucleotide substrates.

The term "comprising" means "including principally, but not necessarily solely". Furthermore, variations of the word "comprising", such as "comprise" and "comprises", have correspondingly varied meanings.

Use of the term "about" herein in reference to a recited numerical value includes the recited numerical value and numerical values within plus or minus ten percent of the recited value.

Use of the term "between" herein when referring to a range of numerical values encompasses the numerical values at each endpoint of the range. For example, a polynucleotide of between 10 nucleotides and 20 nucleotides in length is inclusive of a polynucleotide of 10 nucleotides in length and a polynucleotide of 20 nucleotides in length.

The terms "polynucleotide" and "nucleic acid" are used interchangeably herein and refer to a single- or double-stranded polymer of deoxyribonucleotide and/or ribonucleotide bases, and/or analogues, derivatives, variants, fragments or combinations thereof, including but not limited to DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof. By way of non-limiting example, the source of a nucleic acid may be selected from the group consisting of synthetic, mammalian, human, animal, plant, fungal, bacterial, viral, archael sources or any combination thereof.

The term "oligonucleotide" typically denotes a segment of DNA or a DNA-containing nucleic acid molecule, or RNA or RNA-containing molecule, or a combination thereof. An oligonucleotide may thus comprise or consist of deoxyribonucleotide and/or ribonucleotide bases, and/or analogues, derivatives, variants, fragments or combinations thereof, including but not limited to DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof. Examples of oligonucleotides include nucleic acid targets; substrates, for example, those which can be modified by a DNAzyme or an MNAzyme with cleavage, ligase or other enzymatic activity; primers such as those used for in vitro target amplification by methods such as PCR; and components of MNAzymes including, but not limited to partzymes, and assembly facilitators.

The term "pyrimidine nucleotide" encompasses any nucleotide comprising a pyrimidine base including, but not limited to, cytosine, thymine and uracil. A pyrimidine nucleotide may comprise a ribose sugar molecule (ie. a "pyrimidine ribonucleotide") or a deoxyribose sugar molecule (ie. a "pyrimidine deoxyribonucleotide").

The term "purine nucleotide" encompasses any nucleotide comprising a purine base including, but not limited to, adenine and guanine. A purine nucleotide may comprise a ribose sugar molecule (ie. a "purine ribonucleotide") or a deoxyribose sugar molecule (ie. a "purine deoxyribonucleotide").

The terms "nucleic acid enzyme", "catalytic nucleic acid", "nucleic acid with catalytic activity", and "catalytic nucleic acid enzyme" are used herein interchangeably and shall mean a DNA or DNA-containing molecule or complex or an RNA or RNA-containing molecule or complex, or a combination thereof being a DNA-RNA hybrid molecule or complex, which may bind at least one substrate and catalyse a modification (such as ligation or cleavage) of the at least one substrate. The nucleotide residues in the catalytic nucleic acids may include the bases A, C, G, T, and U, as well as derivatives and analogues thereof. The terms above include uni-molecular nucleic acid enzymes which may comprise a single DNA or DNA-containing molecule (also known in the art as a "DNA enzyme", "deoxyribozyme" or "DNAzyme") or an RNA or RNA-containing molecule (also known in the art as a "RNA enzyme" or "ribozyme") or a combination thereof, being a DNA-RNA hybrid molecule which may recognize at least one substrate and catalyse a modification (such as ligation or cleavage) of the at least one substrate. The terms above include nucleic acid enzymes which comprise a DNA or DNA-containing complex or an RNA or RNA-containing complex or a combination thereof, being a DNA-RNA hybrid complex which may recognize at least one substrate and catalyse a modification (such as ligation or cleavage) of the at least one substrate. The terms "nucleic acid enzyme", "catalytic nucleic acid", "nucleic acid with catalytic activity", and "catalytic nucleic acid enzyme" include within their meaning MNAzymes.

The terms "MNAzyme" and "multi-component nucleic acid enzyme" as used herein have the same meaning and refer to two or more oligonucleotide sequences (e.g. partzymes) which, only in the presence of an MNAzyme assembly facilitator (for example, a target), form an active nucleic acid enzyme that is capable of catalytically modifying a substrate. MNAzymes can catalyse a range of reactions including cleavage of a substrate, ligation of substrates and other enzymatic modifications of a substrate or substrates. An exemplary MNAzyme comprising partzyme A and partzyme B which has cleavage activity is depicted in FIG. 1. MNAzymes with endonuclease or cleavage activity are also known as "MNAzyme cleavers". With reference to FIG. 1, partzymes A and B each bind to an assembly facilitator (e.g. a target DNA or RNA sequence) through Watson-Crick base pairing. The MNAzyme only forms when the sensor arms of partzymes A and B hybridize adjacent to each other on the assembly facilitator. The substrate arms of the MNAzyme engage the substrate, the modification (e.g. cleavage) of which is catalyzed by the catalytic core of the MNAzyme, formed by the interaction of the catalytic domains of partzymes A and B. Cleavage of a DNA/RNA chimeric reporter substrate is exemplified in the drawing. The MNAzyme cleaves the substrate between a fluorophore and a quencher dye pair, thus generating signal. The terms "multi-component nucleic acid enzyme" and "MNAzyme" comprise bipartite structures, composed of two molecules, or tripartite structures, composed of three nucleic acid molecules, or other multipartite structures, for example those formed by four or more nucleic acid molecules.

It will be understood that the terms "MNAzyme" and "multi-component nucleic acid enzyme" as used herein encompass all known MNAzymes and modified MNAzymes including those disclosed in any one or more of PCT patent publication numbers WO/2007/041774, WO/2008/040095, WO2008/122084, and related US patent publication numbers 2007-0231810, 2010-0136536, and 2011-0143338 (the contents of each of these documents are incorporated herein by reference in their entirety). Non-limiting examples of MNAzymes and modified MNAzymes encompassed by the terms "MNAzyme" and "multi-component nucleic acid enzyme" include MNAzymes with cleavage catalytic activity (as exemplified herein), disassembled or partially assembled MNAzymes comprising one or more assembly inhibitors, MNAzymes comprising one or more aptamers ("apta-MNAzymes"), MNAzymes comprising one or more truncated sensor arms and optionally one or more stabilizing oligonucleotides, MNAzymes comprising one or more activity inhibitors, multi-component nucleic acid inactive proenzymes (MNAi), and MNAzymes with ligase catalytic activity ("MNAzyme ligases"), each of which is described in detail in one or more of WO/2007/041774, WO/2008/040095, WO2008/122084, US 2007-0231810, US 2010-0136536, and/or US 2011-0143338.

As used herein, the terms "partzyme", "component partzyme", "partzyme component", "component oligonucleotide", "oligonucleotide component" and "oligonucleotide partzyme" refer to a DNA-containing or RNA-containing or DNA-RNA-containing oligonucleotide, two or more of which, only in the presence of an MNAzyme assembly facilitator as herein defined, can together form an "MNAzyme." In certain preferred embodiments, one or more component partzymes, and preferably at least two, may comprise three regions or domains: a "catalytic" domain, which forms part of the catalytic core that catalyzes a modification; a "sensor arm" domain, which may associate with and/or bind to an assembly facilitator; and a "substrate arm" domain, which may associate with and/or bind to a substrate. Illustrations of these regions or domains are shown in FIG. 1. Partzymes may comprise at least one additional component including but not limited to an aptamer, referred to herein as an "apta-partzyme." A partzyme may comprise multiple components, including but not limited to, a partzyme component with a truncated sensor arm and a stabilizing arm component which stabilises the MNAzyme structure by interacting with either an assembly facilitator or a substrate.

The terms "assembly facilitator molecule", "assembly facilitator", "MNAzyme assembly facilitator molecule", and "MNAzyme assembly facilitator" as used herein refer to entities that can facilitate the self-assembly of component partzymes to form a catalytically active MNAzyme by interaction with the sensor arms of the MNAzyme. As used herein, assembly facilitators may facilitate the assembly of MNAzymes which have cleavage, ligase or other enzymatic activities. In preferred embodiments an assembly facilitator is required for the self-assembly of an MNAzyme. An assembly facilitator may be comprised of one molecule, or may be comprised of two or more "assembly facilitator components" that may pair with, or bind to, the sensor arms of one or more oligonucleotide "partzymes". The assembly facilitator may be a target. The target may be a nucleic acid selected from the group consisting of DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof. The nucleic acid may be amplified. The amplification may comprise one or more of: polymerase chain reaction (PCR), strand displacement amplification, loop-mediated isothermal amplification, rolling circle amplification, transcription-mediated amplification, self-sustained sequence replication, ligase chain reaction, nucleic acid sequence based amplification, or reverse transcription polymerase chain reaction (RT-PCR).

An "assembly facilitator component" is a molecule which can be used to control the assembly of active MNAzymes or facilitate the transition from inactive MNAzyme components to active MNAzymes.

The term "target" as used herein includes any natural or synthetic entity, constituent or analyte which is sought to be detected, identified or quantitated by a method which uses a particular nucleic acid enzyme such as an MNAzyme(s), with or without an additional amplification step and/or cascade. Targets therefore encompass the broadest range of detectable entities, constituents or analytes for which methods of sensitive detection, identification and/or quantification are desirable. Some exemplary targets include, but are not limited to, nucleic acid, protein, polypeptide, peptide, glycoproteins, lipids, lipoproteins, entire organisms, cells, viruses, bacteria, archaea, yeast, fungi, antibodies, metabolites, pathogens, toxins, contaminants, poisons, small molecules, polymers, metal ions, metal salts, prions or any derivatives, portions or combinations thereof. Other targets are also contemplated for use herein. It will be understood that the target may also be an assembly facilitator or assembly facilitator component.

A "detectable effect" is an effect that can be detected or quantified as an indication that modification of substrate/s has occurred. The magnitude of the effect may be indicative of the quantity of an input such as an assembly facilitator (e.g. a target). The detectable effect may be detected by a variety of methods, including fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

The terms "polynucleotide substrate" and "substrate" as used herein include any single- or double-stranded polymer of deoxyribonucleotide or ribonucleotide bases, or analogues, derivatives, variants, fragments or combinations thereof, including but not limited to DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof (including mixed polymers of deoxyribonucleotide and ribonucleotide bases), which is capable of being recognized, acted upon or modified by an enzyme including a catalytic nucleic acid enzyme. A "polynucleotide substrate" or "substrate" may be modified by various enzymatic activities including but not limited to cleavage or ligation. Modification of a "polynucleotide substrate" or "substrate" may provide a "detectable effect" for monitoring the catalytic activity of a enzyme.

A "reporter substrate" as used herein is a substrate that is particularly adapted to facilitate measurement of either the disappearance of a substrate or the appearance of a product in connection with a catalyzed reaction. Reporter substrates can be free in solution or bound (or "tethered"), for example, to a surface, or to another molecule. A reporter substrate can be labelled by any of a large variety of means including, for example, fluorophores (with or without one or more additional components, such as quenchers), radioactive labels, biotin (e.g. biotinylation) or chemiluminescent labels.

As used herein, a "generic substrate" or a "universal substrate" is a substrate, for example, a reporter substrate, that is recognized by and acted on catalytically by a plurality of MNAzymes, each of which can recognize a different assembly facilitator. The use of such substrates facilitates development of separate assays for detection, identification or quantification of a wide variety of assembly facilitators using structurally related MNAzymes all of which recognize a universal substrate. These universal substrates can each be independently labelled with one or more labels. In preferred embodiments, independently detectable labels are used to label one or more universal substrates to allow the creation of a convenient system for independently or simultaneously detecting a variety of assembly facilitators using MNAzymes. In some embodiments, substrates cleaved by MNAzymes could be reconstituted, and hence recycled, using an MNAzyme or DNAzyme ligase. In some embodiments, substrate(s) cleaved or ligated by MNAzymes can be further used as components or modulators of additional MNAzyme(s) or DNAzyme(s).

In some embodiments, "universal substrates" may be tethered to a solid support in different positions to provide a substrate array. In such embodiments, the tethered universal substrates may all be labelled with the same fluorophore. In certain cases, each universal substrate can be cleaved only by an MNAzyme formed in the presence of a specific MNAzyme assembly facilitator molecule and signal can be localised by positioning of the substrate on the surface, thus allowing specific detection of different assembly facilitators.

The term "product" refers to the new molecule or molecules that are produced as a result of enzymatic modification of a substrate. As used herein the term "cleavage product" refers to a new molecule produced as a result of cleavage or endonuclease activity by an enzyme. The term "ligation product" refers to a new molecule produced as a result of the ligation of substrates by an enzyme.

As used herein, use of the terms "melting temperature" and "Tm" in the context of a polynucleotide substrate of the present invention will be understood to be a reference to the melting temperature (Tm) as calculated using the Wallace rule, whereby Tm=2° C.(A+T)+4° C.(G+C) (see Wallace et al., (1979) Nucl. Acids Res. 6(11):3543-3558), unless specifically indicated otherwise.

As used herein, the term "base" will be understood to encompass the entire ribonucleotide or deoxyribonucleotide to which the base is attached.

ABBREVIATIONS

The following abbreviations are used herein and throughout the specification:

MNAzyme: multi-component nucleic acid enzyme, or multipartite nucleic acid enzyme;
DNAzyme: deoxyribonucleic acid enzyme;
Ribozyme: ribonucleic acid enzyme;
Partzyme: Partial enzyme containing oligonucleotide
PCR: polymerase chain reaction;
qPCR: Real-time quantitative PCR;
NF-$H_2O$: nuclease-free water;
LNA: locked nucleic acid;
F: fluorophore;
Q: quencher;
N=A, C, T/U, G, or any analogue thereof;
N'=any nucleotide complementary to N, or able to base pair with N;
$(N)_x$: any number of N;
$(N')_x$: any number of N';
W: A or T;
R: A, G, or AA;
rN: any ribonucleotide;
$(rN)_x$: any number of rN;
rR: A or G ribonucleotide;
rY: C or U; ribonucleotide
M: A or C;
H: A, C, or T/U;
D: G, A, or T/U;
JOE or 6-JOE: 6-carboxy-4',5'-dichloro-2',7'-dimethoxyfluorescein;
FAM or 6-FAM: 6-Carboxyfluorescein.
BHQ1: Black Hole Quencher® 1
BHQ2. Black Hole Quencher® 2
IB: Iowa Black® FQ
IBR: Iowa Black® RQ
shRNA: short hairpin RNA
siRNA: short interfering RNA
mRNA: messenger RNA
tRNA: transfer RNA
snoRNA: small nucleolar RNA
stRNA: small temporal RNA
smRNA: small modulatory RNA
pre-microRNA: precursor microRNA
pri-microRNA: primary microRNA
UV: ultra violet

DETAILED DESCRIPTION OF ILLUSTRATIVE EMBODIMENTS

It is to be understood at the outset, that the figures and examples provided herein are to exemplify rather than limit the present invention and its various embodiments.

A need exists for catalytic nucleic acid substrates with properties that facilitate improved catalytic nucleic acid function. In particular, many applications involving MNAzymes and DNAzymes will benefit significantly from the provision of new universal substrate families having increased capacity for catalytic modification by different MNAzymes with the same or distinct target specificities. For example, these substrate families would be advantageous in increasing the efficiency and/or accuracy of multiplex assays involving MNAzymes. Additional universal substrates are particularly useful in applications where substrate arrays are created by tethering substrates to solid supports.

The present invention provides a set of guidelines for producing universal oligonucleotide substrates with a higher probability of being catalytically modified (e.g. cleaved) efficiently over a broad temperature range with improved performance at elevated temperatures. These guidelines include, but are not limited to, any one or more of: (i) seven or more cytosine nucleotides in the ten bases surrounding the two central ribonucleotides; (ii) bases immediately adjacent to the two central ribonucleotides are cytosines ($N_8$ and $N_9$); (iii) total pyrimidine content of the oligonucleotide substrate is greater than 64%; (iv) total Tm of the oligonucleotide substrate is 66° C. or greater, applicable if the reaction temperature for catalytic modification (e.g. cleavage) of the oligonucleotide substrate by the nucleic acid enzyme is above 50° C.; and/or (v) a low number of guanine nucleotides (e.g. three, two, one or none) in the 10 bases surrounding the two central ribonucleotides.

The development of these guidelines has facilitated the development of catalytic nucleic acid enzyme substrates with features that augment catalytic nucleic acid function. It has been identified that the catalytic modification of nucleotide/s within a substrate targeted by a given nucleic acid enzyme can be enhanced by the presence of certain specific nucleotides proximate to those which are catalytically modified.

Accordingly, certain aspects of the present invention relate to polynucleotide substrates for catalytic nucleic acid enzymes. The polynucleotide substrates may comprise a series of pyrimidine nucleotides 5' (ie. upstream) and/or 3' (ie. downstream) of nucleotide/s that are catalytically modified by a nucleic acid enzyme that targets the substrate. The pyrimidine nucleotides may be cytosine nucleotides.

Other aspects of the present invention relate to the use of polynucleotide substrates described herein as substrates for nucleic acid enzymes (e.g. a DNAzyme, ribozyme or an MNAzyme). In certain embodiments, the substrates are used as substrates for MNAzymes. In certain embodiments, the substrates are used as substrates for DNAzymes.

Additional aspects of the present invention relate to methods for detecting a target molecule. The methods comprise modifying a polynucleotide substrate described herein to provide a detectable effect. In certain embodiments, the methods comprise modifying the polynucleotide substrate using an MNAzyme that is capable of detecting a target.

Further aspects of the present invention relate to kits comprising one or more polynucleotide substrate/s described herein. The kits may comprise a nucleic acid enzyme capable of catalytically modifying the substrate/s. In certain embodiments, the nucleic acid enzyme may be an MNAzyme.

1. Catalytic Nucleic Acid Enzyme Substrate/s

The present invention provides polynucleotide substrates for catalytic nucleic acid enzymes. The present invention also provides substrate families the members of which have increased capacity for catalytic modification by different nucleic acids (e.g. MNAzymes) with the same or distinct target specificities.

The polynucleotide substrates comprise at least one sequence motif that can be modified by a catalytic nucleic acid enzyme. No limitation exists regarding the particular type of catalytic nucleic acid enzyme that may modify a polynucleotide substrate of the present invention. The sequence motif may comprise any one or more of at least one DNA nucleotide, at least one RNA nucleotide, at least one analogue of a DNA nucleotide, and at least one analogue of a RNA nucleotide.

Non-limiting examples of suitable sequence motifs include those recognised and modified by DNAzymes (e.g. 10-23 DNAzymes; 8-17 DNAzymes; "7Z81", "7Z48" and "7Q10" DNAzyme ligases; "UV1C" thymine dimer photo-reversion DNAzymes, "DAB22" carbon-carbon bond forming DNAzymes; and derivatives thereof), ribozymes (e.g. hammerhead ribozymes; homodimeric ribozymes, heterodimeric ribozymes; and derivations thereof), and MNAzymes (see, for example, MNAzymes described in PCT patent publication numbers WO/2007/041774, WO/2008/040095 and WO2008/122084, and related US patent publication numbers 2007-0231810, 2010-0136536, and 2011-0143338; each of which is incorporated herein by reference in its entirety).

Non-limiting examples of suitable sequence motifs include those set out in Table 1 below.

TABLE 1

Exemplary catalytic motifs

| Catalytic Enzyme | Substrate Catalytic Motif |
|---|---|
| 8-17 DNAzyme | (N')$_x$ (rN)$_x$ G (N')$_x$ |
| 10-23 DNAzyme | (N')$_x$ rR rY (N')$_x$ |

N = A, C, T G or any analogue;
N' = any nucleotide complementary to N;
(N)$_x$ or (N')$_x$ = any number of nucleotides;
W = A or T;
R = A, G or AA;
rN = any ribonucleotide base;
(rN)$_x$ = any number of ribonucleotides;
rR = A or G ribonucleotides;
rY = C or U ribonucleotides;
M = A or C;
H = A, C or T;
D = G, A or T Catalytic nucleic acids have been shown to tolerate only certain modifications in the area that forms the catalytic core (Perreault et al., 1990 Nature 344(6266): 565-7; Perreault et al., 1991 Biochemistry 30(16): 4020-5; Zaborowska et al., 2002 J Biol Chem. 277(43): 240617-22; Cruz et al., 2004 Chem Biol. January; 11(1): 57-6; Silverman, 2004 Chem Biol. January; 11(1): 7-8). Examples of sequences responsible for catalytic activity of DNAzymes are listed in Table 2.

TABLE 2

Exemplary sequences for some active DNAzymes and their substrates

| DNAzyme type | DNAzyme sequence | Substrate sequence |
|---|---|---|
| 8-17 | (N)$_x$TNNNAGCNNNWCGR(N)$_x$ SEQ ID NO: 189 | (N')$_x$ (rN)$_x$ G (N')$_x$ |
| 10-23 | (N)$_x$GGMTMGHNDNNNMGD(N)$_x$ SEQ ID NO: 190 | (N')$_x$ rR rY (N')$_x$ |

For the DNAzyme sequence N is generally A, C, T or G or any analogue, in some instances N can be U; for the substrate sequence N = A, C, T/U, G or any analogue; ; N' = any nucleotide complementary to N; (N)$_x$ or (N')$_x$ = any number of nucleotides; W = A or T, in some instances W can be U; R = A, G or AA; rN = any ribonucleotide base; (rN)$_x$ = any number of ribonucleotides; rR = A or G ribonucleotide; rY = C or U ribonucleotide; M = A or C; H = A, C or T, in some instances H can be U; D = G, A or T, in some instances D can be U.

The polynucleotide substrates may comprise multiple sequence motifs. The motifs may be recognised and modified by one type of catalytic nucleic acid enzyme. Alternatively, different sequence motifs within the substrate may be recognised and modified by different types of catalytic nucleic acid enzymes.

As noted above, polynucleotide substrates of the present invention comprise at least one sequence motif capable of modification by a catalytic nucleic acid enzyme. In some embodiments, nucleotides in the proximity of the sequence motif are pyrimidine nucleotides. For example, 1, 2, 3, 4, 5, 6, 7, 8, 9, 10 or more nucleotides preceding and/or succeeding (i.e. following) the sequence motif may be pyrimidine nucleotides. Any one or more of the pyrimidine nucleotides may be cytosine nucleotides.

In other embodiments, the sequence motif is preceded and/or succeeded (ie. followed) directly (ie. in continuous sequence) by one or more pyrimidine nucleotides. For example, the sequence motif may be directly preceded and/or directly succeeded by a sequence of 1, 2, 3, 4, 5, 6, 7, 8, 9, 10 or more pyrimidine nucleotides. Any one or more of the pyrimidine nucleotides may be cytosine nucleotides.

In further embodiments, 1, 2, 3, 4, 5, 6, 7, 8, 9, or 10 or more nucleotides within ten nucleotides 5' (ie. upstream) and/or within ten nucleotides 3' (ie. downstream) of the sequence motif are pyrimidine nucleotides. Any one or more of the pyrimidine nucleotides may be cytosine nucleotides.

In still further embodiments, more than 9, more than 10, or more than 11 nucleotides of the polynucleotide substrate may be cytosine nucleotides. For example, the substrate may comprise or consist of 10, 11, 12, 13, 14, 15, or more than 15 nucleotides, and 9, 10, 11 or more than 11 of these nucleotides may be cytosine nucleotides.

Additionally or alternatively, less than 5, less than 4, less than 3, or less than 2 nucleotides of the polynucleotide substrate may be guanine nucleotides. For example, the substrate may comprise or consist of 10, 11, 12, 13, 14, 15, or more than 15 nucleotides, and 4, 3, 2, 1 or none of these nucleotides may be guanine nucleotides.

No particular limitation exists regarding the length of a polynucleotide substrate of the present invention. For example, the substrate may be less than 100, 75, 50, 40, 30, 25, 24, 23, 22, 21, 20, 19, 18, 17, 16, 15, 14, 13, 12, 11, 10, 9, 8, 7, 6, or 5 nucleotides in length. For example, the substrate may be between 5 and 30, 10 and 15, 10 and 20, 10 and 25, 10 and 30, 16 and 23, 16 and 21, 16 and 18, 18 and 21, 18 and 23, or 21 and 23 nucleotides in length.

A polynucleotide substrate of the present invention may be designed to possess a specific melting temperature (Tm) as calculated using the Wallace rule, whereby Tm=2° C.(A+T)+4° C.(G+C) (see Wallace et al., (1979) Nucl. Acids Res. 6(11):3543-3558). In certain embodiments, the substrate may be recognised and catalytically modified by an MNAzyme, and the Tm of the bases that are bound by the partzyme substrate arm/s of the MNAzyme may be between about 52° C. and about 76° C., between about 55° C. and about 75° C., between about 60° C. and about 70° C., between about 65° C. and about 70° C., between about 64° C. and 68° C., or between 64° C. and 70° C. (as calculated using the Wallace rule).

In other embodiments, the substrate may be recognised and catalytically modified by an MNAzyme or a DNAzyme, and the Tm of the bases that are bound by the partzyme substrate arm/s of the MNAzyme may be between 68° C. and 90° C., between 66° C. and 76° C., between 68° C. and 76° C., between 64° C. and 70° C., between 70° C. and 76° C., between 70° C. and 75° C., between 72° C., and 76° C., 52° C., 58° C., 64° C., 66° C., 68° C., 70° C., 72° C., or 76° C.

By way of non-limiting example only, a polynucleotide substrate of the present invention may comprise a sequence defined in any one or more of SEQ ID NOs: 25-27, 29-30, 72-90, or 172-175. In certain embodiments, the polynucleotide substrate may consist of a sequence defined in any one or more of SEQ ID NOs: 25-27, 29-30, 72-90, or 172-175.

In some embodiments, a polynucleotide substrate of the present invention may comprise a sequence defined by SEQ ID NO: 28. In other embodiments, the polynucleotide substrate may consist of a sequence defined by SEQ ID NO: 28.

In some embodiments, polynucleotide substrates of the present invention are capable of catalytic modification by an MNAzyme comprising two oligonucleotide partzymes. The sequences of the polynucleotide substrate and the oligonucleotide partzymes may be any specific combination of three sequences (as depicted by SEQ ID NOs) that is shown in Table 6, 8, 10, 13, 16, 20, 22 and/or 24.

In other embodiments, polynucleotide substrates of the present invention are capable of catalytic modification by a DNAzyme. The sequences of the polynucleotide substrate and DNAzyme may be any specific pair of sequences (as depicted by SEQ ID NOs) that is shown in Table 15.

Polynucleotide substrates of the present invention may contain one or more substitutions such as analogues, derivatives, modified or altered bases, ribonucleotides, alterations of the sugar or phosphate backbone, various deletions, insertions, substitutions, duplications or other modifications, or any combination of these, well known to those skilled in the art.

Non-limiting examples of additions or substitutions include LNA phosphoramidite, 4-acetylcytidine, 5-(carboxyhydroxylmethyl)uridine, 2'-O-methylcytidine, 5-carboxymethylaminomethyl thiouridine, dihydrouridine, 2'-O-methylpseudouridine, beta D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta D-mannosylmethyluridine, 5-methoxycarbonylmethyluridine, 5-methoxyuridine, 2-methylthio-N6-isopentenyladenosine, N-((9-beta-ribofuranosyl-2-methylthiopurine-6-yl)carbamoyl)threonine, N-((9-beta-ribofuranosylpurine-6-yl)N-methyl-carbamoyl)threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-beta-D-ribofuranosylpurine-6-yl) carbamoyl)threonine, 2'-O-methyl-5-methyluridine, 2'-O-methyluridine, wybutosine, 3-(3-amino-3-carboxypropyl) uridine, beta D-arabinosyl uridine, and beta D-arabinosyl thymidine.

Non-limiting examples of derivatives include functionally equivalent nucleic acids or nucleotides, including any fusion molecules produced integrally (e.g. by recombinant means) or added post-synthesis (e.g. by chemical means). Such fusions may comprise oligonucleotides of the invention with RNA or DNA added thereto or conjugated to a polypeptide (e.g. puromycin or other polypeptide), a small molecule (e.g. psoralen), a microcarrier or nanocarrier, or an antibody.

Non-limiting examples of analogues include compounds having a physical structure that is related to a DNA or RNA molecule or residue, and may be capable of forming a hydrogen bond with a DNA or RNA residue or an analogue thereof (i.e. it is able to anneal with a DNA or RNA residue or an analogue thereof to form a base-pair), but such bonding is not so required for said compound to be encompassed within the term "analogue". Such analogues may possess different chemical and biological properties to the ribonucleotide or deoxyribonucleotide residue to which they are structurally related. Methylated, iodinated, brominated or biotinylated residues are examples of analogues. Active DNAzymes have been described which contain nucleotide analogues, including deoxyinosine, C-5-imidazole deoxyuridine, 3-(aminopropynyl)-7-deaza-dATP, 2'-O-methyl RNA, 2' O-methyl cap. Other analogues could also be compatible with catalytic activity of DNAzymes and MNAzymes. Alteration of a nucleic acid with catalytic activity, for example by substitution of one base for another, by substitution of an analogue for a base, or alteration of the sugar component or phosphodiester backbone, can be straight forward for the skilled artisan. For example, alterations can be made during synthesis, or by modification of specific bases after synthesis. Empirical testing of catalytic nucleic acids incorporating alterations such as base changes or base analogues allows for assessment of the impact of the altered sequences, or specific analogues, on catalytic activity. Analogues of the bases A, C, G, T and U are known in the art, and a subset is listed in Table 3.

TABLE 3

Exemplary nucleotide analogues

| Abbreviation | Name |
| --- | --- |
| ac4c | 4-acetylcytidine |
| chm5u | 5-(carboxyhydroxylmethyl)uridine |
| Cm | 2'-O-methylcytidine |
| Cmnm5s2u | 5-carboxymethylaminomethyl thiouridine |
| D | Dihydrouridine |
| Fm | 2'-O-methylpseudouridine |
| Galq | beta, D-galactosylqueosine |
| Gm | 2'-O-methylguanosine |
| I | Inosine |
| i6a | N6-isopentenyladenosine |
| m1a | 1-methyladenosine |
| m1f | 1-methylpseudouridine |
| m1g | 1-methyl guanosine |
| Ml1 | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5u | 5-methylaminomethyluridine |
| mam5s2u | 5-methoxyaminomethyl-2-thiouridine |
| Manq | beta, D-mannosylmethyluridine |
| mcm5s2u | 5-methoxycarbonylmethyluridine |
| Mo5u | 5-methoxyuridine |
| Ms2i6a | 2-methylthio-N6-isopentenyladenosine |
| Ms2t6a | N-(9-beta-ribofuranosyl-2-methylthiopurine-6-yl)carbamoyl)threonine |
| Mt6a | N-(9-beta-ribofuranosylpurine-6-yl)N-methyl-carbamoyl)threonine |
| Mv | Uridine-5-oxyacetic acid methylester |
| o5u | Uridine-5-oxyacetic acid (v) |
| Osyw | Wybutoxosine |
| P | Pseudouridine |
| Q | Queosine |
| s2c | 2-thiocytidine |
| s2t | 5-methyl-2-thiouridine |
| s2u | 2-thiouridine |
| s4u | 4-thiouridine |
| T | 5-methyluridine |
| t6a | N-((9-beta-D-ribofuranosylpurine-6-yl)carbamoyl)threonine |
| Tm | 2'-O-methyl-5-methyluridine |
| Um | 2'-O-methyluridine |
| Yw | Wybutosine |
| X | 3-(3-amino-3-carboxypropyl)uridine, (acp3)u |
| AraU | beta D-arabinosyluridine |
| AraT | beta D-arabinosylthymidine |

Polynucleotide substrates of the present invention may incorporate additional entities such as labelled nucleic acids, nanoparticles, microparticles, proteins, antibodies, RNA, DNA, nucleic acid analogues, proteins, glycoproteins, lipoproteins, peptide nucleic acids, locked nucleic acids, peptide-nucleic acid chimeras, or any combination thereof. The nanoparticles may be gold nanoparticles.

Polynucleotide substrates of the present invention may be catalytically modified by a catalytic nucleic acid enzyme. Non-limiting examples of potential catalytic modifications include cleavage of nucleic acids, ligation of nucleic acids, phosphorylation of nucleic acids, nucleic acid capping, amino acid adenylation, cofactor synthesis, RNA polymerization, template-directed polymerization, RNA-protein conjugation, aldol reaction, alcohol oxidation, aldehyde reduction, purine and pyrimidine nucleotide synthesis, alkylation, amide synthesis, urea synthesis, formation of peptide bonds, peptidyl-RNA synthesis, acyl transfer, aminoacylation, carbonate hydrolysis, phosphorothioate alkylation, porphyrin metallation, formation of carbon-carbon bonds, Pd nanoparticle formation, biphenyl isomerization, formation of ester bonds, formation of amide bonds, DNA deglycosylation, thymine dimer photoreversion and phosphoramidate cleavage.

In certain applications, it may be desirable to detect product/s arising from catalytic modification of polynucleotide substrates of the present invention. This can be achieved using any number of standard techniques known in the art.

For example, the substrate may comprise a detectable portion and a quencher portion, wherein upon modification of said substrate by a catalytic nucleic acid, a detectable effect provided by said detectable portion is increased or decreased. The detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, electrochemical; photometry, scintigraphy, electronic methods, UV, visible light or infra red spectroscopy, enzymatic methods or any combination thereof.

Additionally or alternatively, product/s arising from catalytic modification of polynucleotide substrates of the present invention may be detected on the basis of size (e.g. by standard electrophoresis), nucleic acid sequencing, fluorescence resonance energy transfer, chemiluminescence, potentiometry, mass spectrometry, plasmon resonance, colorimetry, polarimetry, flow cytometry, scanometry, and DNA sequencing or any combination thereof.

Nucleic acid product/s arising from catalytic modification of polynucleotide substrates of the present invention may be amplified in order to assist detection using techniques such as, for example the polymerase chain reaction (PCR).

Polynucleotide substrates of the present invention may be recognized and modified by catalytic nucleic acid enzymes (e.g. MNAzymes) designed to detect a target that differs from the substrate to be modified by the enzyme. Accordingly, polynucleotide substrates of the present invention may be "generic" or "universal" substrates that are recognized by and acted on catalytically by a plurality of catalytic nucleic acid enzymes (e.g. a plurality of MNAzymes), each of which can recognize a different target. The use of such substrates may facilitate the development of separate assays for detection, identification or quantification of a wide variety of targets using catalytic nucleic enzymes which recognize a universal substrate. The universal substrates may each be independently labelled with one or more labels. In certain embodiments, independently detectable labels may be used to label one or more universal substrates to allow for the independent or simultaneous detection of a variety of targets using MNAzymes. For example, a series of universal substrates may be used in a multiplex reaction allowing simultaneous detection of multiple targets.

Polynucleotide substrates of the present invention may be provided bound, attached or tethered to an insoluble or solid support for use in various applications (e.g. enzymatic cascades or any other signal transduction cascades). The support may be an insoluble material, or a matrix which retains the substrate and excludes it from freely moving in the bulk of the reaction mixture. Such supports are known in the art for immobilizing or localizing substrates, including nucleic acid targets. The skilled addressee will appreciate that the support can be selected from a wide variety of matrices, polymers, and the like in a variety of forms including beads convenient for use in microassays, as well as other materials compatible with the reaction conditions. In certain preferred embodiments, the support can be a plastic material, such as plastic beads or wafers, or that of the well or tube in which a particular assay is conducted. In certain embodiments, the support may be a microcarrier or a nanocarrier. The attachment of the substrate to the support may be designed so that upon modification (e.g. cleavage) of the substrate by the catalytic nucleic acid (e.g. MNAzyme), a portion of the modified substrate remains attached to the support, while the other is freed to move into the bulk of the reaction mixture, away from the portion remaining attached.

2. Exemplary Methods

Polynucleotide substrates of the present invention may be used in any number of potential applications utilising catalytic nucleic acids which recognise/modify the substrates.

For example, the substrates may be used in applications involving DNAzymes (e.g. 10-23 DNAzymes; 8-17 DNAzymes; "7Z81", "7Z48" and "7Q10" DNAzyme ligases; "UV1C" thymine dimer photoreversion DNAzymes, "DAB22" carbon-carbon bond forming DNAzymes; and derivations thereof), ribozymes (e.g. hammerhead ribozymes; homodimeric ribozymes, heterodimeric ribozymes; and derivations thereof), and/or MNAzymes.

In certain embodiments of the invention, the substrates may be used as substrates for MNAzymes. The features of MNAzymes and various applications using MNAzymes are described in detail in PCT patent publication numbers WO/2007/041774, WO/2008/040095 and WO2008/122084, and related US patent publication numbers 2007-0231810, 2010-0136536, and 2011-0143338 (the contents of each of these documents are incorporated herein by reference in their entirety).

MNAzymes are capable of self-assembling from two or more oligonucleotide components, also referred to herein as partzymes. The partzyme oligonucleotides self-assemble in the presence of an MNAzyme self assembly facilitator to form an MNAzyme. MNAzymes are therefore catalytically active nucleic acid enzymes. In some embodiments, the presence of an MNAzyme can be detected, and is indicative of the presence of a target, because the MNAzyme forms only in the presence of the target, wherein the target comprises the assembly facilitator.

In preferred embodiments, the MNAzyme structures are based on one or more DNAzymes and/or ribozymes. More preferred are those MNAzyme structures which are based on a particular DNAzyme structure. Presently preferred structures are based on DNAzymes including the 10-23 and 8-17 DNAzymes. In various embodiments the MNAzymes comprise either or both ribonucleotide bases and deoxyribonucleotide bases. In more preferred embodiments, an MNAzyme structure is based at least in part on the structure of a DNAzyme. In other preferred embodiments, MNAzymes comprise at least some deoxyribonucleotide bases or analogues thereof. In more preferred embodiments, the catalytic core of an MNAzyme comprises one or more deoxyribonucleotide bases or analogues thereof. In still more preferred embodiments, one or more deoxyribonucleotide bases or analogues thereof are involved in the catalysis of a substrate.

In other embodiments, at least one deoxyribonucleotide base, or its analogue, in the catalytic core improves catalytic activity. In yet other embodiments, there is a strict requirement for at least one deoxyribonucleotide base, or its analogue, in the catalytic core of the MNAzyme for catalysis to occur at a measurable rate, relative to that of a comparable MNAzyme without the deoxyribonucleotide base present.

The MNAzymes may contain one or more substitutions such as analogues, derivatives, modified or altered bases, ribonucleotides, alterations of the sugar or phosphate backbone, various deletions, insertions, substitutions, duplications or other modifications, or any combination of these, well known to those skilled in the art. Such modifications, substitutions, deletions, insertions, etc may be made in the sensor and/or substrate arms and/or in the catalytic core portions, such that the molecule retains catalytic activity. Substitutions and modifications to arms that bind the substrate or assembly facilitator may be well tolerated and in fact are the basis of allowing tailoring of the molecules to different substrates/assembly facilitators. For example, modification of the sensor arms will allow tailoring to different assembly facilitators, while modification of the substrate arms will allow tailoring to different substrates.

The MNAzyme may comprise either deoxyribonucleotides or ribonucleotides, or even both. MNAzymes comprising at least one and more preferably, all, deoxyribonucleotide component oligonucleotides are preferred. Also preferred are MNAzymes comprising at least one deoxyribonucleotide base, or its analogue, within the catalytic core of the MNAzyme. Even more preferred are those embodiments where such a base is required for catalytic activity.

MNAzyme assembly and disassembly may also be controlled by changing the microenvironment. Examples of such changes include, but are not limited to, temperature, divalent cation type and concentration, salt concentration, pH, additives, and the presence or absence of critical components essential for assembly and/or activity of an active MNAzyme. Accordingly, disassembled or partially assembled MNAzymes may be prevented from assembling into a catalytically active MNAzyme in the presence of an assembly facilitator by modulating the microenvironment, thus providing a "molecular switch".

A basic example of a MNAzyme structure is depicted in FIG. 1. The structure shown comprises partzyme A and partzyme B, the sensor arms (i) of which have base-paired with an MNAzyme assembly facilitator molecule, for example a target DNA or RNA. Partzymes A and B by interacting with the assembly facilitator have allowed the partial catalytic cores (iii) to come into close proximity and thereby form a single catalytic core. The substrate arms (ii) of the MNAzyme have interacted with and base-paired with a substrate, depicted here as a Reporter Substrate. Thus the MNAzyme has self-assembled and this process is facilitated through the presence of the MNAzyme assembly facilitator molecule. In the absence of assembly facilitator, no MNAzyme will form. Modification (in this case, cleavage) of a polynucleotide substrate of the present invention is catalyzed by the catalytic core of the MNAzyme at the MNAzyme Modification Site (e.g. Cleavage Site within the substrate denoted by a cross (X)). The polynucleotide substrate in this particular embodiment comprises a detectable portion having a detectable signal, for example fluorophore F, and a quencher portion Q having a quenching effect on the detectable signal F through the action of quencher Q. Upon cleavage at the MNAzyme Cleavage Site, there is a substantial increase in detectable signal, here fluorescence, which can readily detected and quantified if so desired.

FIG. 1 can further be understood to depict an example of a basic method of using MNAzymes to detect a target, which in some embodiments comprises an assembly facilitator. More specifically, partzyme A and partzyme B are shown in FIG. 1, each comprising a substrate arm portion (ii), catalytic core portion (iii), and a sensor arm portion (i). In the presence of a target, the sensor arm portions of partzyme A and partzyme B can begin to hybridize to, and base pair with complementary portions, of the target, for example a DNA or RNA sequence. Upon contacting the target in this fashion, the MNAzyme self-assembles forming a catalytic core which can modify a substrate which is bound by the substrate arms. Preferably the presence of the MNAzyme is detected through the detection or measurement of its catalytic activity. The substrate arms of the thus assembled MNAzyme can engage a polynucleotide substrate of the present invention through the interaction of the complementary sequences on the substrate arms and the substrate. Once the substrate is so engaged with the substrate arms, the catalytic core can promote the modification (e.g. cleavage) of the substrate, which can in turn be measured or detected, directly or indirectly.

The skilled artisan will readily appreciate that the methods described herein may involve amplification of a target before, during or after MNAzyme catalytic activity. Such target amplification finds particular application in embodiments of the present invention where the amount of target being sought to be detected, identified or quantified is of such quantum so as to provide a signal that may otherwise not be detectable. Such amplification may comprise one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

Figure 2:
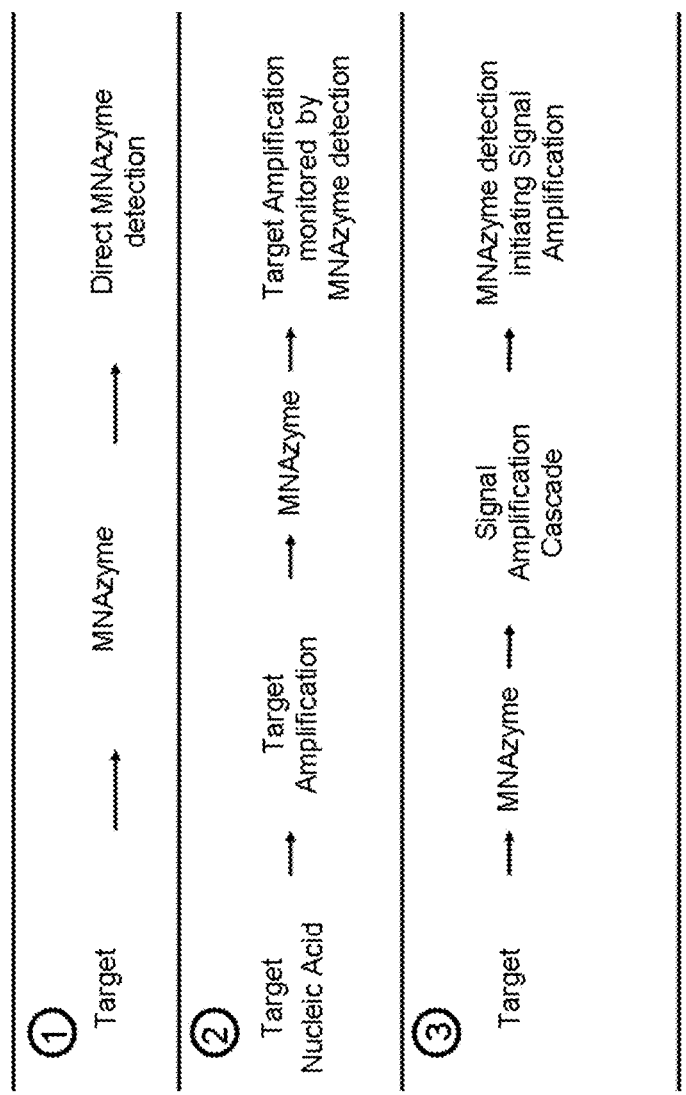
FIG. 2 provides a flow chart showing exemplary applications of methods for target detection using MNAzymes. MNAzymes can be used for (1) direct detection; (2) detecting amplicons generated, for example, by PCR, SDA, LAMP, RCA, TMA, 3SR or NASBA either during, or following, target amplification; and (3) initiating a signal amplification cascade.

FIG. 2 provides exemplary applications of methods for target detection using MNAzymes. Strategy 1 exemplifies MNAzymes adapted for detection of targets including DNA, RNA and proteins. As described above (see description of FIG. 1) an MNAzyme composed of two separate oligonucleotides with recognition sequences for both a target and a substrate forms when the oligonucleotides recognize and bind a target. The substrate, e.g. reporter substrate, is modified by the catalytic action of the MNAzyme and causes generation of a detectable signal, either directly (Strategy 1), during or after target amplification (Strategy 2) or via a signal cascade (Strategy 3). In some embodiments, both target and signal amplification occur simultaneously or sequentially.

Strategy 2 of FIG. 2 exemplifies the use of an MNAzyme adapted to monitor the accumulation of amplicons during, or following, in vitro amplification of nucleic acid targets. Techniques for in vitro amplification of nucleic acid sequences are known in the art. These include techniques mediated by a DNA polymerase, such as the polymerase chain reaction ("PCR") (see, for example, U.S. Pat. No. 4,683,202; U.S. Pat. No. 4,683,195; U.S. Pat. No. 4,800,159; U.S. Pat. No. 4,965,188; U.S. Pat. No. 5,176,995), strand displacement amplification ("SDA"), rolling circle amplification ("RCA"), reverse transcription polymerase chain reaction (RT-PCR) and loop-mediated isothermal amplification ("LAMP"). Other target amplification techniques are mediated by an RNA polymerase, for example, transcription-mediated amplification ("TMA"), self-sustained sequence replication ("3SR") and nucleic acid sequence replication based amplification ("NASBA"). The amplification products ("amplicons") produced by PCR, RT-PCR, SDA, RCA and LAMP are composed of DNA, whereas RNA amplicons are produced by TMA, 3SR and NASBA.

With further reference to strategy 2 of FIG. 2 an MNAzyme that recognises and modifies a polynucleotide substrate of the present invention can be used in conjunction with target amplification methods which include, for example, the aforementioned PCR, RT-PCR, SDA, RCA, LAMP, TMA, 3SR and NASBA. The accumulation of amplicons produced by PCR using either asymmetric or symmetric primer ratios can be monitored using MNAzymes. Examples 1, 2, 4, 6, 8 and 9 of the present specification demonstrate the detection of PCR amplicons in real time utilising MNAzymes that catalytically modify various polynucleotide substrates of the present invention.

Again referring to strategy 2 of FIG. 2, a target nucleic acid may be amplified in accordance with a procedure for amplifying that nucleic acid (ie. DNA or RNA). Preferably, standard methods of in vitro amplification are used. The amplicons generated during the amplification may serve as target assembly facilitators for an MNAzyme. The MNAzyme activity, which is made detectable by modification of a polynucleotide substrate of the present invention by the MNAzyme, is indicative of the presence of the target. The skilled artisan will appreciate that assays of this nature can be conducted in a single vessel under conditions that permit both the target nucleic acid amplification and the MNAzyme assembly and catalytic activity. Additionally or alternatively, they can be conducted subsequent to, or at time points throughout, the target nucleic acid amplification, by removing samples at the end or during the course of the amplification reactions.

Strategy 3 of FIG. 2 shows an overview of a method of using a MNAzyme to initiate amplification of a signal through the use of a signal cascade. Example 3 of the present specification demonstrates the isothermal direct detection of a target utilising MNAzymes that catalytically modify various polynucleotide substrates of the present invention, which could be used to initiate a signal cascade.

The skilled addressee will appreciate that methods or protocols that combine target amplification with catalytic nucleic acid activity may require specific reaction conditions (e.g. those described in Examples 1, 2, 4, 6, 8 and 9 of the present specification). Preferably, reaction conditions are compatible with both polymerase activity (for amplification), and catalytic nucleic acid modification of a substrate (for detection). Protocols for determining conditions for concurrent catalytic activity and polymerase activity at high temperature, such as during PCR, have been described for DNAzymes. The influence of factors including DNAzyme arm length, buffer, temperature, divalent ion concentration and effects of additives are known in the art. DNA enzymes are suited for use in combination with in vitro amplification strategies. For example, they are not irreversibly denatured by exposure to high temperatures during amplification.

In certain embodiments, a polynucleotide substrate of the present invention capable of recognition and modification by an MNAzyme may be bound, attached or tethered to an insoluble or solid support. For example, with reference to FIG. 3, Panel (i), an exemplary method for detecting targets using an MNAzyme and a polynucleotide substrate of the present invention anchored to a support is depicted. In this embodiment, the substrate is preferably a substrate with a detectable portion comprising a detectable signal, for example a fluorophore, and a quencher portion which diminishes or eliminates the detectable signal while the detectable portion and the quencher portion of the substrate remain in close proximity, for example, until the substrate is modified (e.g. by cleavage). The substrate is attached to a support. Preferably the support is an insoluble material, or a matrix which retains the substrate and excludes it from freely moving in the bulk of the reaction mixture. The attachment of the substrate to the support may be designed such that upon modification (e.g. by cleavage) of the substrate by the MNAzyme, either the detectable portion or the quencher portion, but not both, remains attached to the support, while the other is freed to move into the bulk of the reaction mixture, away from the portion remaining attached. Thus, in a cleavage example, the detectable signal vastly increases as the quencher portion and the detectable portion are separated upon cleavage. In the embodiment shown in FIG. 3, Panel (i), the fluorophore-containing detectable. portion remains attached after cleavage. This has the benefit of allowing localization of the signal on the support but in certain instances, the fluorophore/s may be released into solution. In a further embodiment where, for example, ligation occurs, the quencher may be ligated to a fluorophore thus decreasing the detectable signal.

Figure 3:
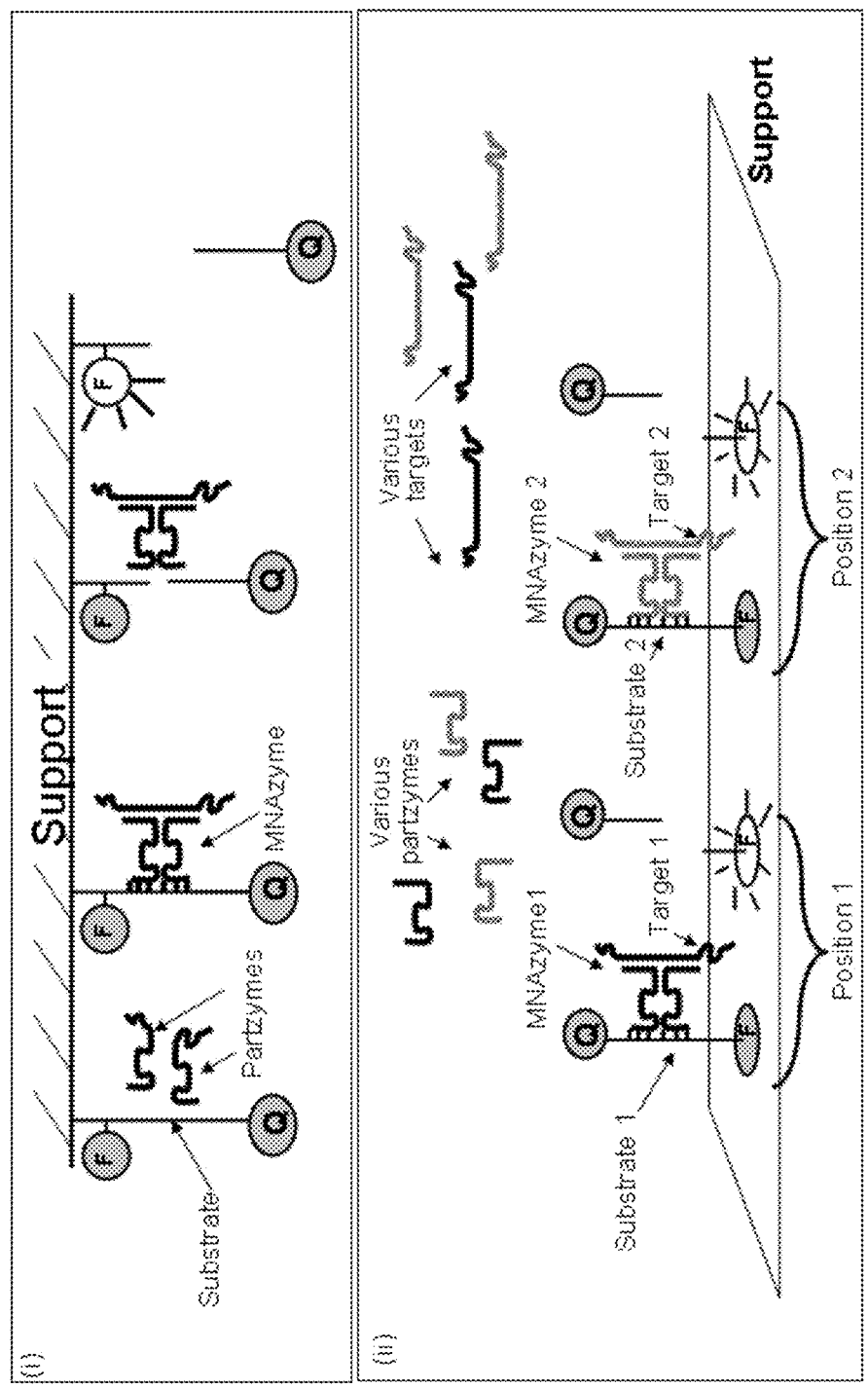
FIG. 3 provides a depiction of exemplary MNAzymes and a method for target detection using MNAzymes that cleave substrates tethered to a support. In this embodiment, the MNAzyme forms only in the presence of an assembly facilitator (target). When the MNAzyme cleaves the tethered substrate between a fluorophore and quencher, a signal is generated. As shown here, upon cleavage between fluorophore F and quencher Q, there is a resultant increase in fluorescence. In general, the method may be designed such that either fluorophore F or quencher Q may stay attached to the support once cleavage occurs. Panel (i): The support shown has only one substrate type (Substrate 1) tethered to it. Panel (ii): There may be multiple substrate types tethered in different positions. Each substrate can be cleaved only by a MNAzyme formed in the presence of a specific MNAzyme assembly facilitator molecule—here, Targets 1 and 2 facilitate the self-assembly of MNAzymes 1 and 2 respectively. Thus, in this example MNAzyme 1 only self-assembles in the presence of Target 1 and only cleaves Substrate 1. Similarly, MNAzyme 2 only self-assembles in the presence of Target 2 and only cleaves Substrate 2. The signal can be localised by positioning of the substrate on the surface, thus allowing specific detection of different assembly facilitators. The exemplary assay in Panel (ii) requires two distinct substrate sequences.

In certain embodiments, multiple universal substrates may be tethered to a solid support in different positions to provide a substrate array. With reference to FIG. 3 Panel (ii), two substrates may be attached at defined positions on a solid surface. Each universal substrate can be cleaved only by an MNAzyme formed in the presence of a specific MNAzyme assembly facilitator molecule (e.g. target 1 or target 2) and signal can be localised by positioning of the substrate on the surface (position 1 or position 2), thus allowing specific detection of different assembly facilitators. In such embodiments tethered universal substrates may all be labelled with the same fluorophore. In other embodiments tethered universal substrates may be labelled with different fluorophores. The strategy depicted in FIG. 3 (ii) can be extended to create universal substrate arrays with many different universal substrates attached in defined positions on a solid surface. In such embodiments increasing the number of universal substrates that are available for use in arrays may provide an advantage by allowing the creation of more complex arrays. Such universal arrays of universal substrates may have utility for use in highly multiplexed analysis of target analytes. The present invention provides additional universal substrates with features that may augment catalytic activity function which may be useful in improving the capacity to perform increasingly more complex analysis using MNAzymes.

In certain embodiments, a polynucleotide substrate of the present invention may be recognised and modified by a MNAzyme to provide an assembly facilitator, assembly facilitator component, or partzyme for a second different MNAzyme.

Figure 4:
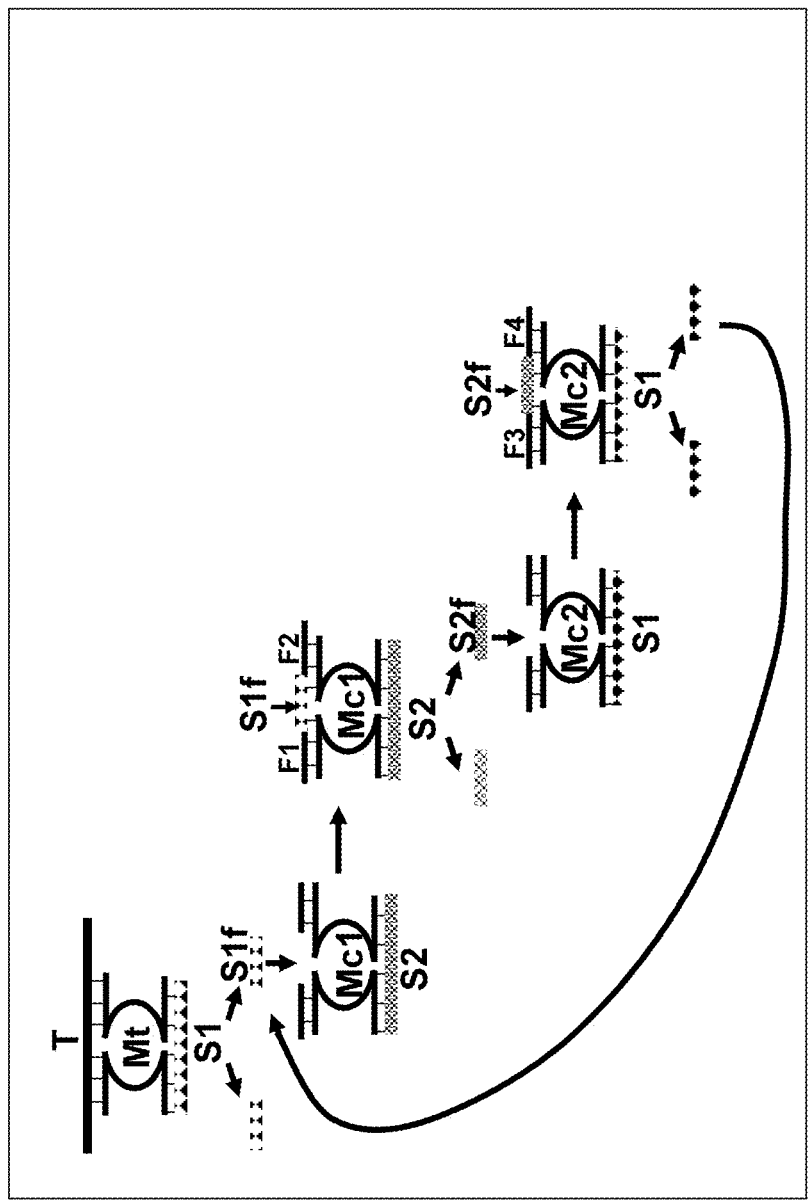
FIG. 4 shows an exemplary assay using catalytically modified substrate products as MNAzyme assembly facilitator components. In this strategy an initiating MNAzyme (Mt) is formed in the presence of a target (T). The initiating MNAzyme (Mt) cleaves a first substrate (S1) to create a first assembly facilitator component (S1f), which directs formation of a first cascading MNAzyme (cascading MNAzyme Mc1). In this example the first cascading MNAzyme (Mc1) comprises two partzymes and three assembly facilitator components designated F1, F2 and S1f. Mc1 can cleave an additional substrate (S2) thus liberating an additional assembly facilitator component (S2f), which directs formation of a second cascading MNAzyme (cascading MNAzyme Mc2). In this example the second cascading MNAzyme (Mc2) comprises two partzymes and three assembly facilitator components designated F3, F4 and S2f. Mc2 can then cleave more of the first substrate (S1) thus creating more of the first assembly facilitator component (S1f). This leads to the formation of further first cascading MNAzyme (Mc1) thereby forming an amplification cascade. This exemplary assay requires two distinct substrate sequences.

With reference to FIG. 4, an initiating MNAzyme (Mt) may be formed in the presence of a target (T). The initiating MNAzyme (Mt) cleaves a (first) polynucleotide substrate of the present invention (S1) to create a first assembly facilitator component (S1 f), which directs formation of a first cascading MNAzyme (cascading MNAzyme Mc1). In this example the first cascading MNAzyme (Mc1) comprises two partzymes and three assembly facilitator components designated F1, F2 and S1f. Mc1 can cleave an additional substrate (S2) thus liberating an additional assembly facilitator component (S2f), which directs formation of a second cascading MNAzyme (cascading MNAzyme Mc2). In this example the second cascading MNAzyme (Mc2) comprises two partzymes and three assembly facilitator components designated F3, F4 and S2f. Mc2 can then cleave more of the first substrate (S1) thus creating more of the first assembly facilitator component (S1f). This leads to the formation of further first cascading MNAzyme (Mc1) thereby forming an amplification cascade. The skilled addressee will recognise that FIG. 4 shows three assembly facilitator components are required to facilitate active MNAzyme assembly. More or less assembly facilitator components could be utilised in a similar schema.

The skilled artisan will readily understand that the methods described herein may be optimized using a variety of experimental parameters in order to optimize the detection, identification and/or quantification of a target, and/or the recognition and catalytic modification of a polynucleotide substrate of the present invention by a catalytic nucleic acid (e.g. an MNAzyme or a DNAzyme). The particular experimental parameters that are optimized, and the level of such optimization, will depend upon the particular method being employed and the particular target and/or substrate involved. Such parameters include, but are not limited to, time, temperature, concentration of salts, detergents, cations and other reagents including but not limited to dimethylsulfoxide (DMSO), and length, complementarity, GC content and melting point (Tm) of nucleic acids.

In some embodiments, for example those methods involving detection of sequence variation and/or detection of methylated DNA, the experimental parameters, and preferably including the temperature at which the method is performed, may be optimized so as to discriminate between binding of an MNAzyme component nucleic acid to a target nucleic acid that does or does not comprise a sequence variation or a methylated nucleotide, respectively. The temperature at which such methods may be performed may be in the range of about 20° C. to about 96° C., about 20° C. to about 75° C., 20° C. to about 60° C. or about 20 to about 55° C.

In some embodiments, optimized reactions for practicing the methods of using MNAzymes and DNAzymes are provided herein. In such optimized reactions, catalytic activity is increased by up to 10, 20, or 30% above unoptimized reactions. More preferred reaction conditions improve catalytic activity by at least 35%, or 40%, and preferably up to 50% or more. In still more preferred embodiments, optimized reactions have an increase of catalytic activity of more than 50%, and up to 66%, 75% or even 100%. In yet more preferred embodiments, a fully optimized reaction method will offer 100, 200 or even 300% or more increase in catalytic activity. Other preferred reaction conditions can improve the catalytic activity by up to 1,000% or more over methods practiced with unoptimized reaction conditions. A highly preferred reaction condition for optimizing the methods provided herein is the inclusion of certain divalent cations. The catalytic activity of most nucleic acid enzymes may be influenced in a concentration-dependent fashion by the concentration of divalent cations. Preferred optimized reactions are optimized for one or more of $Ba^{2+}$, $Sr^{2+}$, $Mg^{2+}$, $Ca^{2+}$, $Ni^{2+}$, $Co^{2+}$, $Mn^{2+}$, $Zn^{2+}$, and $Pb^{2+}$.

In some embodiments, the use of polynucleotide substrates of the present invention in assays with nucleic acid enzymes (e.g. MNAzymes or DNAzymes) may increase a detectable effect (e.g. an increase or decrease in fluorescent signal) arising from catalytic modification of the substrate by the enzyme above the detectable effect gained using a known substrate in the same assay under the same conditions. For example, the detectable effect may be increased by more than 2%, more than 3%, more than 4%, more than 5%, more than 6%, 7%, 8%, 9%, 10%, 11%, 12%, 13%, 14%, 15%, 20%, 25%, 30%, 40%, or more than 50% compared to the known substrate. In certain embodiments, the detectable effect is a fluorescent signal.

In some embodiments, the methods of the invention involve using a polynucleotide substrate for an MNAzyme in combination with an MNAzyme comprising two oligonucleotide partzymes. The sequences of the polynucleotide substrate and the oligonucleotide partzymes may be any specific combination of three sequences (as depicted by SEQ ID NOs) that is shown in Table 6, 8, 10, 13, 16, 20, 22 and/or 24.

In some embodiments, the methods of the invention involve using a polynucleotide substrate in combination with a DNAzyme. The sequences of the polynucleotide substrate and DNAzyme may be any specific pair of sequences (as depicted by SEQ ID NOs) that is shown in Table 15.

3. Kits

Also provided herein are kits comprising one or more polynucleotide substrates of the present invention.

The kits may comprise additional reagents for practising the methods disclosed herein. For example, the kits may comprise one or more catalytic nucleic acids capable of recognising and modifying the substrate. Non-limiting examples of suitable catalytic nucleic acids include DNAzymes (e.g. 10-23 DNAzymes; 8-17 DNAzymes; "7Z81", "7Z48" and "7Q10" DNAzyme ligases; "UV1C" thymine dimer photoreversion DNAzymes, "DAB22" carbon-carbon bond forming DNAzymes; and derivations thereof), ribozymes (e.g. hammerhead ribozymes; homodimeric ribozymes, heterodimeric ribozymes; and derivations thereof), and MNAzymes.

Kits of the present invention may be "compartmentalised" kits. A compartmentalised kit encompasses any kit in which reagents are provided in separate containers such as, for example, small glass containers, plastic containers or strips of plastic or paper. Such containers may allow the efficient transfer of reagents from one compartment to another compartment whilst avoiding cross-contamination of samples and reagents, and/or allow the addition of agents or solutions of each container from one compartment to another in a quantitative fashion. Such kits may also include a container which will accept a sample to be tested, a container which contains reagents to be used in the assay, containers which contain wash reagents, and containers which contain a detection reagent.

In certain embodiments, the kits comprise one or more polynucleotide substrates of the present invention and a plurality of oligonucleotide partzymes designed to assemble an MNAzyme capable of recognising and catalytically modifying the polynucleotide substrate in the presence of target. The target may act as an assembly facilitator causing assembly of the oligonucleotide partzymes into a catalytically active MNAzyme capable of recognising and modifying the polynucleotide substrate.

In some embodiments, the kits comprise a polynucleotide substrate of the present invention and an MNAzyme comprising two oligonucleotide partzymes. The sequences of the polynucleotide substrate and the oligonucleotide partzymes may be any specific combination of three sequences (as depicted by SEQ ID NOs) that is shown in Table 6, 8, 10, 13, 16, 20, 22 and/or 24.

In other embodiments, the kits comprise a polynucleotide substrate of the present invention and a DNAzyme. The sequences of the polynucleotide substrate and DNAzyme may be any specific pair of sequences (as depicted by SEQ ID NOs) that is shown in Table 15.

Individual oligonucleotide partzymes may be present in the same container. Alternatively, individual oligonucleotide partzyme/s may be present in separate containers. It will be understood that not all components for all MNAzymes intended to be used in a given method need necessarily to be provided in a kit as such component/s may be generated as part of a cascade reaction.

In other embodiments, components for additional catalytic nucleic acids with, for example, either cleavage or ligase activity may also form part of the kits of the present invention. In yet other embodiments the kits of the present invention may include DNAzymes or components thereof.

Kits of the present invention may include instructions for using the kit components in order to conduct desired methods.

Kits and methods of the invention may be used in conjunction with automated analysis equipment and systems including, but not limited to, real time PCR machines.

Kits of the present invention may include additional reagents for conducting target amplification reactions (e.g. PCR) including, for example, oligonucleotide primers, buffers, magnesium ions, polymerase enzymes and the like.

Kits of the present invention may comprise one or more assemblies comprising one or more solid supports and one or more polynucleotide substrates of the present invention. One or more of the solid supports may be bound to one or more of the polynucleotide substrates. In certain embodiments, the kits may comprise one or more assemblies comprising a plurality of different solid supports. The plurality of different solid supports may be bound to a plurality of different polynucleotide substrates of the present invention.

EXAMPLES

In the following examples, the ability of MNAzymes based on the 10-23 DNAzyme, and 10-23 DNAzymes, to efficiently cleave universal substrates was tested. The universal substrates tested included some of those previously known in the art (Table 4) and the novel substrates designed according to either all or a subset of the design guidelines of the present invention (Table 5). These examples demonstrate the robustness, as indicated by efficient cleavage in a range of conditions, of universal substrates designed according to all or a subset of the design guidelines of the present invention.

TABLE 4

Previously known universal substrates used in Examples

| Name | Sequence* |
|---|---|
| Sub2 (SEQ ID NO: 21) | AAGGTTTCCTCguCCCTGGGCA |
| Sub3 (SEQ ID NO: 22) | CAGCACAACCguCACCAACCG |
| Sub6 (SEQ ID NO: 23) | ATCACGCCTCguTCCTCCCAG |
| Sub7 (SEQ ID NO: 24) | TTAACATGGCACguTGGCTGTGATA |
| Sub4 (SEQ ID NO: 171) | CATGGCGCACguTGGGAGAAGTA |

*Uppercase letters indicate DNA, lower case letters indicate RNA.

TABLE 5

Improved universal substrates from the current invention used in Examples

| Name | Sequence* |
|---|---|
| Sub44 (SEQ ID NO: 25) | CAGGTCTCCTCguCCCTATAGTGA |
| Sub45 (SEQ ID NO: 26) | ACGGGTCCCguCTCCTTTGGAA |
| Sub46 (SEQ ID NO: 27) | ACCGCACCTguCCCCAGCTC |
| Sub49 (SEQ ID NO: 28) | TAAACTTGGCTCguTGGCTGTGATA |
| Sub55 (SEQ ID NO: 29) | ACCGCACCTCguCCCCAGCTC |
| Sub59 (SEQ ID NO: 33) | CCTCCTCCCTguCCCTCCTCCT |
| Sub60 (SEQ ID NO: 30) | GCCAACCACguCCAACACGAC |
| Sub60T (SEQ ID NO: 72) | TGCCAACCACguCCAACACGAC |
| Sub61 (SEQ ID NO: 73) | CTCGACCCCguCTCCACGCCA |
| Sub65 (SEQ ID NO: 74) | TCTCGACCTCguCTCCACGCCA |
| Sub72 (SEQ ID NO: 75) | ATCACGCCTCguCTCCTCCCAG |
| Sub73 (SEQ ID NO: 76) | TGGCGTCCCCguCCCCTCGTG |
| Sub74 (SEQ ID NO: 77) | ATCACTCCCCguCCCCTCCCAG |
| Sub75 (SEQ ID NO: 78) | TGACCCTCCTCguCTCCCCACTA |
| Sub77 (SEQ ID NO: 79) | CTCCTCCCTCguCCCTCCTCCT |
| Sub79 (SEQ ID NO: 80) | TCCTCTCCCCguCCCCTTCAACC |
| Sub80 (SEQ ID NO: 81) | AACCGCCCTCguCCCGTGAACC |
| Sub82 (SEQ ID NO: 82) | CTCCTCCCTCguCCCTCGTCCA |
| Sub83 (SEQ ID NO: 83) | TCCGCTCCCCguCCCCTGCAAC |
| Sub84 (SEQ ID NO: 84) | ACCGCACCTCguCTCCTCCCAG |
| Sub85 (SEQ ID NO: 85) | ACCGCACCTCguCCCCTCCCAG |
| Sub86 (SEQ ID NO: 86) | ATCACGCCTCguCCCCAGCTC |
| Sub87 (SEQ ID NO: 87) | ATCACTCCCCguCCCCAGCTC |
| Sub88 (SEQ ID NO: 88) | CTCCTCCCTCguCCCCAGCTC |
| Sub89 (SEQ ID NO: 89) | ACCGCACCTCguCCCTCCTCCT |
| Sub90 (SEQ ID NO: 90) | CTCGACCCTCguCCCTCGTCCA |
| Sub55(16) (SEQ ID NO: 172) | GCACCTCguCCCCAGC |
| Sub55(18) (SEQ ID NO: 173) | CGCACCTCguCCCCAGCT |
| Sub55(23A) (SEQ ID NO: 174) | AACCGCACCTCguCCCCAGCTCA |
| Sub55(23C) (SEQ ID NO: 175) | CACCGCACCTCguCCCCAGCTCC |

*Uppercase letters indicate DNA, lower case letters indicate RNA.

Example 1

Use of Universal Substrates with MNAzymes in Real-Time Quantitative PCR (qPCR), at an Annealing Temperature of 52° C.

MNAzymes can be used to monitor amplification of target nucleic acids in real-time using in vitro target amplification methods such as PCR, referred to as MNAzyme qPCR. Further, real-time monitoring during qPCR using MNAzyme substrates labelled with fluorophore and quencher pairs generates a curve on which a threshold line, of an arbitrary level of fluorescence, can be placed over the exponential phase of the reactions, producing a value which can be known as a Ct (cycle threshold). Reactions that produce a lower Ct value are indicative of more efficient cleavage of a specific substrate since such reactions reach the threshold cycle faster. In this example amplification and detection are performed in a one-step process, wherein PCR amplification and MNAzyme-mediated detection occur simultaneously in a single tube. The amount of time taken to reach the threshold fluorescence, measured by the Ct value generated, can be influenced by the sequence of the universal substrate.

In this example, previously known universal substrates from series 1 (Sub2, Sub3, Sub6 and Sub7, see Table 4) are compared to new improved universal substrates, series 2 (Sub44, Sub45, Sub46, Sub49, Sub55 and Sub60, see Table 5) that are the subject of the present invention to determine if the series 2 substrates have the same, higher or lower level of activity in real-time PCR as series 1 substrates. The level of activity was determined by the Ct obtained for each reaction containing individual substrates during real-time PCR.

1.1. Partzyme Oligonucleotides

In the experiments conducted to measure the efficiency of cleavage of universal substrates previously known (Table 4) and novel universal substrates (Table 5) in real-time, all the partzyme oligonucleotides A and B were designed with sensor arms complementary to the same sequence of the human RPLPO gene. The sequences of the A and B partzymes are listed below from 5' to 3', where the bases underlined hybridize to their matched substrate. The "-P" indicates 3' phosphorylation of the oligonucleotide.

```
                                          SEQ ID NO: 1
partzyme A RPLPOA/2-P:
CAAACGAGTCCTGGCCTTGTCTACAACGAGAGGAAACCTT SEQ ID NO: 2
partzyme B RPLPOB/2-P:
TGCCCAGGGAGGCTAGCTGTGGAGACGGATTACACCTTC SEQ ID NO: 3
partzyme A RPLPOA/3-P:
CAAACGAGTCCTGGCCTTGTCTACAACGAGGTTGTGCTG SEQ ID NO: 4
partzyme B RPLPOB/3-P:
CGGTTGGTGAGGCTAGCTGTGGAGACGGATTACACCTTC SEQ ID NO: 5
partzyme A RPLPOA/6-P:
CAAACGAGTCCTGGCCTTGTCTACAACGAGAGGCGTGAT SEQ ID NO: 6
partzyme B RPLPOB/6-P:
CTGGGAGGAAGGCTAGCTGTGGAGACGGATTACACCTTC SEQ ID NO: 7
partzyme A RPLPOA/7-P:
CAAACGAGTCCTGGCCTTGTCTACAACGAGTGCCATGTTAA SEQ ID NO: 8
partzyme B RPLPOB/7-P:
TATCACAGCCAAGGCTAGCTGTGGAGACGGATTACACCTTC SEQ ID NO: 9
partzyme A RPLPOA/44-P:
CAAACGAGTCCTGGCCTTGTCTACAACGAGAGGAGACCTG
```

-continued

SEQ ID NO: 10
partzyme B RPLPOB/44-P:
TCACTATAGGGAGGCTAGCTGTGGAGACGGATTACACCTTC

SEQ ID NO: 11
partzyme A RPLPOA/45-P:
CAAACGAGTCCTGGCCTTGTCTACAACGAGGGACCCGT

SEQ ID NO: 12
partzyme B RPLPOB/45-P:
TTCCAAAGGAGAGGCTAGCTGTGGAGACGGATTACACCTTC

SEQ ID NO: 13
partzyme A RPLPOA/46-P:
CAAACGAGTCCTGGCCTTGTCTACAACGAAGGTGCGGT

SEQ ID NO: 14
partzyme B RPLPOB/46-P:
GAGCTGGGGAGGCTAGCTGTGGAGACGGATTACACCTTC

SEQ ID NO: 15
partzyme A RPLPOA/49-P:
CAAACGAGTCCTGGCCTTGTCTACAACGAGAGCCAAGTTTA

SEQ ID NO: 16
partzyme A RPLPOA/55-P:
CAAACGAGTCCTGGCCTTGTCTACAACGAGAGGTGCGGT

SEQ ID NO: 17
partzyme A RPLPOA/60-P:
CAAACGAGTCCTGGCCTTGTCTACAACGAGTGGTTGGC

SEQ ID NO: 18
partzyme B RPLPOB/60-P:
GTCGTGTTGGAGGCTAGCTGTGGAGACGGATTACACCTTC 1.2. Reporter Substrates The reporter substrates tested in this example are shown below with the sequence, 5' to 3'. The lower case bases represent RNA and the upper case bases represent DNA. In the current example the substrates, other than Sub60, were end labelled with a 6-FAM moiety at the 5' end and a quencher moiety at the 3' end. The quencher molecule was either Black Hole Quencher 1 (indicated by a "B" in the name of the substrate below) or Iowa Black® FQ (indicated by an "IB" in the name of the substrates below). Sub60 was end labelled with a quencher moiety at the 5' end and a FAM moiety at the 3' end (due to the 5' terminal base being a "G" which is known to quench FAM fluorescence). Cleavage of the substrates was monitored between 510-530 nm (FAM emission wavelength range on CFX96 (BioRad)) with excitation between 450-490 nm (FAM excitation wavelength range on CFX96 (BioRad)).

SEQ ID NO: 21
Sub2-FIB:
AAGGTTTCCTCguCCCTGGGCA

SEQ ID NO: 22
Sub3-FB:
CAGCACAACCguCACCAACCG

SEQ ID NO: 23
Sub6-FIB:
ATCACGCCTCguTCCTCCCAG

SEQ ID NO: 24
Sub7-FB:
TTAACATGGCACguTGGCTGTGATA

SEQ ID NO: 25
Sub44-FIB:
CAGGTCTCCTCguCCCTATAGTGA

SEQ ID NO: 26
Sub45-FIB:
ACGGGTCCCguCTCCTTTGGAA

SEQ ID NO: 27
Sub46-FIB:
ACCGCACCTguCCCCAGCTC

SEQ ID NO: 28
Sub49-FB:
TAAACTTGGCTCguTGGCTGTGATA

SEQ ID NO: 29
Sub55-FIB:
ACCGCACCTCguCCCCAGCTC

SEQ ID NO: 30
Sub60-IBF:
GCCAACCACguCCAACACGAC 1.3. PCR Primers for Amplification of RPLPO The target PCR amplicon for this example was generated by in vitro PCR amplification of human genomic DNA using the oligonucleotide PCR primers listed below. Primer sequences are written 5' to 3'.

SEQ ID NO: 31
Forward primer 5RPLPO:
CCCATTCTATCATCAACGGGTA

SEQ ID NO: 32
Reverse primer 3RPLPO:
GCCCACTGTGGTCCTGGTG 1.4. Target Sequence

The target sequence for this example was a PCR amplicon of the RPLPO gene generated by in vitro PCR amplification of human genomic DNA extracted from K562 cells.

1.5. Reaction Components: Amplification and Detection of a Target Sequence

Real-time PCR amplification and detection of the target sequence was performed in a total reaction volume of 25 μL. All reactions were conducted in a CFX96 Real-Time PCR Detection System (Bio-Rad). The cycling parameters were 95° C. for 10 minutes, 10 cycles of 95° C. for 15 seconds and 60° C. for 30 seconds (−1° C. per cycle for the latter temperature), 40 cycles of 95° C. for 15 seconds and 52° C. for 60 seconds (data collected at the 52° C. step). Reactions were set up with substrates and their associated partzymes as in Table 6. Each set of reaction conditions were run in duplicate and contained 80 nM 5RPLPO and 400 nM of 3RPLPO, 200 nM each of partzyme A and partzyme B, 200 nM of substrate, 8 mM MgCl$_2$, 200 μM of each dNTP, 10 units RiboSafe RNase inhibitor (Bioline), 1× Immobuffer (Bioline), 2 units of Immolase (Bioline) and either genomic DNA template (50 ng) or no-DNA target (nuclease free H$_2$O (NF-H$_2$O)). Separate reactions were set up to test each substrate with its matched partzymes. The same PCR primers were used for all reactions and all partzymes had the same target-sensing portions. Any differences in efficiency of reactions will therefore be attributable to differences in the efficiency of cleavage of the substrates.

TABLE 6

Partzyme combinations used for each universal substrate

| Substrate | Partzyme A | Partzyme B |
|---|---|---|
| Sub2 | RPLPOA/2-P | RPLPOB/2-P |
| SEQ ID NO: 21 | SEQ ID NO: 1 | SEQ ID NO: 2 |

TABLE 6-continued

Partzyme combinations used for each universal substrate

| Substrate | Partzyme A | Partzyme B |
|---|---|---|
| Sub3 SEQ ID NO; 22 | RPLP0A/3-P SEQ ID NO: 3 | RPLP0B/3-P SEQ ID NO: 4 |
| Sub6 SEQ ID NO: 23 | RPLP0A/6-P SEQ ID NO: 5 | RPLP0B/6-P SEQ ID NO: 6 |
| Sub7 SEQ ID NO: 24 | RPLP0A/7-P SEQ ID NO: 7 | RPLP0B/7-P SEQ ID NO: 8 |
| Sub44 SEQ ID NO: 25 | RPLP0A/44 SEQ ID NO: 9 | RPLP0B/44-P SEQ ID NO: 10 |
| Sub45 SEQ ID NO: 26 | RPLP0A/45-P SEQ ID NO: 11 | RPLP0B/45-P SEQ ID NO: 12 |
| Sub46 SEQ ID NO: 27 | RPLP0A/46-P SEQ ID NO: 13 | RPLP0B/46-P SEQ ID NO: 14 |
| Sub49 SEQ ID NO: 28 | RPLP0A/49-P SEQ ID NO: 15 | RPLP0B/7-P SEQ ID NO: 8 |
| Sub55 SEQ ID NO: 29 | RPLP0A/55-P SEQ ID NO: 16 | RPLP0B/46-P SEQ ID NO: 14 |
| Sub60 SEQ ID NO: 30 | RPLP0A/60-P SEQ ID NO: 17 | RPLP0B/60-P SEQ ID NO: 18 |

1.6. Results: Amplification of Target and Cleavage of Reporter Substrate

Each MNAzyme qPCR reaction containing human genomic DNA, with each different substrate, showed an increase in fluorescence over time for the real-time detection of RPLP0 from human genomic DNA. For all substrates, the fluorescence of the no-DNA target control was lower than that in the DNA target-containing reactions. This demonstrates that the increase in fluorescence produced in target-containing reactions is due to target dependent assembly of catalytically active MNAzymes that then cleaved one of the universal substrates.

The series 1 and 2 substrates all crossed the threshold producing a Ct value, as seen in Table 7. The series 1 substrates had Ct values in the range from 16.9 (Sub6) to 18.4 (Sub3 and Sub7) and the series 2 substrates had Ct values in the range of 17.1 (Sub55) to 19.2 (Sub45). This indicates that the series 2 substrates are highly active and very comparable to series 1 substrates under the reaction conditions tested. These results demonstrate that, on average, the substrates that were cleaved with the greatest efficiency (i.e. lowest Ct) were those with a higher number of pyrimidines in the eight bases surrounding the ribonucleotides in the substrate (underlined in Table 7).

TABLE 7

Efficiency of cleavage of universal substrates (listed in order of cleavage efficiency based on Ct)

| Name | Sequence^ | # pyrimidines in 8 bases surrounding ribonucleotides | Tm* | Ct |
|---|---|---|---|---|
| Sub6 SEQ ID NO: 23 | ATCACGCCTCguTCCTCCCAG | 8 | 64 | 16.9 |
| Sub2 SEQ ID NO: 21 | AAGGTTTCCTCguCCCTGGGCA | 8 | 66 | 17.0 |
| Sub55 SEQ ID NO: 29 | ACCGCACCTCguCCCCAGCTC | 8 | 68 | 17.1 |
| Sub44 SEQ ID NO: 25 | CAGGTCTCCTCguCCCTATAGTGA | 8 | 70 | 18.0 |
| Sub46 SEQ ID NO: 27 | ACCGCACCTguCCCCAGCTC | 7 | 64 | 18.1 |
| Sub60 SEQ ID NO: 30 | GCCAACCACguCCAACACGAC | 5 | 64 | 18.3 |
| Sub3 SEQ ID NO: 22 | CAGCACAACCguCACCAACCG | 5 | 64 | 18.4 |
| Sub7 SEQ ID NO: 24 | TTAACATGGCACguTGGCTGTGATA | 4 | 68 | 18.4 |
| Sub49 SEQ ID NO: 28 | TAAACTTGGCTCguTGGCTGTGATA | 5 | 68 | 18.5 |
| Sub45 SEQ ID NO: 26 | ACGGGTCCCguCTCCTTTGGAA | 8 | 66 | 19.2~ |

^Uppercase represent DNA and lowercase represent RNA
*Tm given here equates to the melting temperature of the bases bound to the two partzymes calculated using the Wallace rule. When the substrate is bound to the MNAzyme based on the 10-23 DNAzyme the "g" ribonucleotide remains unbound therefore does not contribute to the overall bound Tm.
~Only one replicate due to experimental error.

Example 2

Use of Universal Substrates with MNAzymes qPCR at an Annealing Temperature of 58° C.

MNAzymes can be used to monitor amplification of target nucleic acids in real-time using in vitro target amplification methods such as PCR. Furthermore, real-time monitoring during qPCR using MNAzyme substrates labelled with fluorophore and quencher pairs generates a curve on which a threshold line, of an arbitrary level of fluorescence, can be placed over the exponential phase of the reactions, producing a value which can be known as a Ct (cycle threshold). Reactions that produce a lower Ct value are indicative of more efficient cleavage of a specific substrate since such reactions reach the threshold cycle faster. In this example, amplification and detection are performed in a one-step process, wherein PCR amplification and MNAzyme-mediated detection occur simultaneously in a single tube. Where all other reaction conditions are the same the Ct value can be influenced by the sequence of the universal substrate. The annealing/detection temperature for MNAzyme qPCR used in the art is between 50 and 54° C. This temperature was dictated by the fact that the universal substrates known in the art had a limitation on the temperature at which they were efficiently cleaved with 54° C. being the upper limit for the series 1 universal substrates. There is a need for universal substrates that cleave at higher temperatures to allow greater flexibility in design of primers and partzymes that anneal at higher temperatures. This design flexibility for primers and partzymes could be of great benefit for many applications such as genetic targets of interest that have high percentages of G and C bases in their sequence, requiring higher reaction temperatures and hence partzymes and primers with higher Tms for specific detection.

Investigation into efficiency of cleavage of substrates based on the performance of the series 1 and 2 substrates, lead to the development of guidelines to aid in a third round of substrate designs, resulting in the series 3 substrates. These guidelines included but were not limited to (i) seven or more cytosine nucleotides in the ten bases surrounding the ribonucleotides ($N_4$-$N_{13}$), (ii) bases immediately adjacent to the ribonucleotides are cytosines ($N_8$ and $N_9$) (iii) total content of substrate has >64% pyrimidines and (iv) total Tm of the oligonucleotide is 66° C. or greater (where this latter guideline is only applicable if the reaction temperature for substrate cleavage is above 50° C.).

In this example, the series 1 universal substrates (Sub2, Sub3 and Sub6) are compared to the series 2 universal substrates (Sub44, Sub 45, Sub46, Sub60T and Sub55), and the series 3 substrates (Sub61, Sub65, Sub72, Sub73, Sub74, Sub75, Sub77, Sub79, Sub80, Sub82, Sub83, Sub84, Sub85, Sub86, Sub87, Sub88, Sub89 and Sub90) to compare the cleavage efficiency of all substrates in real-time PCR at 58° C. to ensure that the design guidelines produce universal substrates with a high probability of applicability to MNAzyme qPCR at an elevated temperature. The level of cleavage efficiency was determined by measuring the Ct value for reactions containing different universal substrates.

2.1. Partzyme Oligonucleotides

In the experiments conducted to measure the efficiency of cleavage of the series 1, 2 and 3 universal substrates in real-time PCR, all the partzyme oligonucleotides A and B were designed with sensor arms complementary to the same sequence of the human TFRC gene. The sequences of the A and B partzymes are listed below from 5' to 3', where the bases underlined hybridize to their matched universal substrate. The "-P" indicates 3' phosphorylation of the oligonucleotide.

SEQ ID NO: 34
partzyme A TFRCA/2-P:
GGAATATGGAAGGAGACTGTCACAACGA<u>GAGGAAACCTT</u>

SEQ ID NO: 35
partzyme B TFRCB/2-P:
<u>TGCCCAGGGA</u>GGCTAGCTCCTCTGACTGGAAAACAGACT SEQ ID NO: 36
partzyme A TFRCA/3-P:
GGAATATGGAAGGAGACTGTCACAACGA<u>GGTTGTGCTG</u>

SEQ ID NO: 37
partzyme B TFRCB/3-P:
<u>CGGTTGGTGA</u>GGCTAGCTCCTCTGACTGGAAAACAGACT SEQ ID NO: 38
partzyme A TFRCA/6-P:
GGAATATGGAAGGAGACTGTCACAACGA<u>GAGGCGTGAT</u>

SEQ ID NO: 39
partzyme B TFRCB/6-P:
<u>CTGGGAGGAA</u>GGCTAGCTCCTCTGACTGGAAAACAGACT SEQ ID NO: 40
partzyme A TFRCA/44-P:
GGAATATGGAAGGAGACTGTCACAACGAGA<u>GGAGACCTG</u>

SEQ ID NO: 41
partzyme B TFRCB/44-P:
<u>TCACTATAGGGA</u>GGCTAGCTCCTCTGACTGGAAAACAGACT SEQ ID NO: 42
partzyme A TFRCA/45-P:
GGAATATGGAAGGAGACTGTCACAACGA<u>GGGACCCGT</u>

SEQ ID NO: 43
partzyme B TFRCB/45-P:
<u>TTCCAAAGGAGA</u>GGCTAGCTCCTCTGACTGGAAAACAGACT SEQ ID NO: 44
partzyme A TFRCA/46-P:
GGAATATGGAAGGAGACTGTCACAACGA<u>AGGTGCGGT</u>

SEQ ID NO: 45
partzyme B TFRCB/46-P:
<u>GAGCTGGGGA</u>GGCTAGCTCCTCTGACTGGAAAACAGACT SEQ ID NO: 46
partzyme A TFRCA/55-P:
GGAATATGGAAGGAGACTGTCACAACGA<u>GAGGTGCGGT</u>

SEQ ID NO: 48
partzyme A TFRCA/60-P:
GGAATATGGAAGGAGACTGTCACAACGA<u>GTGGTTGGC</u>

SEQ ID NO: 49
partzyme B TFRCB/60-P:
<u>GTCGTGTTGGA</u>GGCTAGCTCCTCTGACTGGAAAACAGACT SEQ ID NO: 50
partzyme A TFRCA/61-P:
GGAATATGGAAGGAGACTGTCACAACGA<u>GGGGTCGAG</u>

SEQ ID NO: 51
partzyme B TFRCB/61-P:
<u>TGGCGTGGAGA</u>GGCTAGCTCCTCTGACTGGAAAACAGACT SEQ ID NO: 52
partzyme A TFRCA/65-P:
GGAATATGGAAGGAGACTGTCACAACGA<u>GAGGTCGAGA</u>

SEQ ID NO: 55
partzyme B TFRCB/72-P:
<u>CTGGGAGGAGA</u>GGCTAGCTCCTCTGACTGGAAAACAGACT -continued

```
                                              SEQ ID NO: 56
partzyme A TFRCA/73-P:
GGAATATGGAAGGAGACTGTCACAACGAGGGGACGCCA SEQ ID NO: 57
partzyme B TFRCB/73-P:
CACGAGGGGAGGCTAGCTCCTCTGACTGGAAAACAGACT SEQ ID NO: 58
partzyme A TFRCA/74-P:
GGAATATGGAAGGAGACTGTCACAACGAGGGGAGTGAT SEQ ID NO: 59
partzyme B TFRCB/74-P:
CTGGGAGGGGAGGCTAGCTCCTCTGACTGGAAAACAGACT SEQ ID NO: 60
partzyme A TFRCA/75-P:
GGAATATGGAAGGAGACTGTCACAACGAGAGGAGGGTCA SEQ ID NO: 61
partzyme B TFRCB/75-P:
TAGTGGGGAGAGGCTAGCTCCTCTGACTGGAAAACAGACT SEQ ID NO: 62
partzyme A TFRCA/77-P:
GGAATATGGAAGGAGACTGTCACAACGAGAGGGAGGAG SEQ ID NO: 63
partzyme B TFRCB/77-P:
AGGAGGAGGGAGGCTAGCTCCTCTGACTGGAAAACAGACT SEQ ID NO: 64
partzyme A TFRCA/79-P:
GGAATATGGAAGGAGACTGTCACAACGAGGGGAGAGGA SEQ ID NO: 65
partzyme B TFRCB/79-P:
GGTTGAAGGGGAGGCTAGCTCCTCTGACTGGAAAACAGACT SEQ ID NO: 66
partzyme A TFRCA/80-P:
GGAATATGGAAGGAGACTGTCACAACGAGAGGGCGGTT SEQ ID NO: 67
partzyme B TFRCB/80-P:
GGTTCACGGGAGGCTAGCTCCTCTGACTGGAAAACAGACT SEQ ID NO: 68
partzyme B TFRCB/82-P:
TGGACGAGGGAGGCTAGCTCCTCTGACTGGAAAACAGACT SEQ ID NO: 69
partzyme A TFRCA/83-P:
GGAATATGGAAGGAGACTGTCACAACGAGGGGAGCGGA SEQ ID NO: 70
partzyme B TFRCB/83-P:
GTTGCAGGGGAGGCTAGCTCCTCTGACTGGAAAACAGACT SEQ ID NO: 71
partzyme A TFRCA/90-P:
GGAATATGGAAGGAGACTGTCACAACGAGAGGGTCGAG
```

2.2. Reporter Substrates

The reporter substrates for this example are shown below with the sequence, 5' to 3'. The lower case bases represent RNA and the upper case bases represent DNA. In the current example, the substrates were end labelled with a 6-FAM moiety at the 5' end (indicated by a "F" in the name of the substrates below) and an Iowa Black® FQ quencher moiety at the 3' end (indicated by a "IB" in the name of the substrates below). The sequence of Sub60 was been modified to include a "T" at the 5' end, this enabled it to be 5' end-labelled with 6-FAM. The partzyme A substrate binding sequence has not changed and therefore cleavage efficiency is comparable to the Sub60 sequence in Example 1 which lacks the extra "T" at the 5' end. Cleavage of the substrates was monitored between 510-530 nm (FAM emission wavelength range on CFX96 (BioRad)) with excitation between 450-490 nm (FAM excitation wavelength range on CFX96 (BioRad)).

```
                                              SEQ ID NO: 21
Sub2-FIB:
AAGGTTTCCTCguCCCTGGGCA

SEQ ID NO: 22
Sub3-FIB:
CAGCACAACCguCACCAACCG

SEQ ID NO: 23
Sub6-FIB:
ATCACGCCTCguTCCTCCCAG

SEQ ID NO: 25
Sub44-FIB:
CAGGTCTCCTCguCCCTATAGTGA

SEQ ID NO: 26
Sub45-FIB:
ACGGGTCCCguCTCCTTTGGAA

SEQ ID NO: 27
Sub46-FIB:
ACCGCACCTguCCCCAGCTC

SEQ ID NO: 29
Sub55-FIB:
ACCGCACCTguCCCCAGCTC

SEQ ID NO: 72
Sub60T-FIB:
TGCCAACCACguCCAACACGAC

SEQ ID NO: 73
Sub61-FIB:
CTCGACCCCguCTCCACGCCA

SEQ ID NO: 74
Sub65-FIB:
TCTCGACCTCguCTCCACGCCA

SEQ ID NO: 75
Sub72-FIB:
ATCACGCCTCguCTCCTCCCAG

SEQ ID NO: 76
Sub73-FIB:
TGGCGTCCCCguCCCCTCGTG

SEQ ID NO: 77
Sub74-FIB:
ATCACTCCCCguCCCCTCCCAG

SEQ ID NO: 78
Sub75-FIB:
TGACCCTCCTCguCTCCCCACTA

SEQ ID NO: 79
Sub77-FIB:
CTCCTCCCTCguCCCTCCTCCT

SEQ ID NO: 80
Sub79-FIB:
TCCTCTCCCCguCCCCTTCAACC

SEQ ID NO: 81
Sub80-FIB:
AACCGCCCTCguCCCGTGAACC

SEQ ID NO: 82
Sub82-FIB:
CTCCTCCCTCguCCCTCGTCCA
```

-continued

Sub83-FIB:
TCCGCTCCCCguCCCTGCAAC
SEQ ID.NO: 83

Sub84-FIB:
ACCGCACCTCguCTCCTCCCAG
SEQ ID NO: 84

Sub85-FIB:
ACCGCACCTCguCCCCTCCCAG
SEQ ID NO: 85

Sub86-FIB:
ATCACGCCTCguCCCCAGCTC
SEQ ID NO: 86

Sub87-FIB:
ATCACTCCCCguCCCCAGCTC
SEQ ID NO: 87

Sub88-FIB:
CTCCTCCCTCguCCCCAGCTC
SEQ ID NO: 88

Sub89-FIB:
ACCGCACCTCguCCCTCCTCCT
SEQ ID NO: 89

Sub90-FIB:
CTCGACCCTCguCCCTCGTCCA
SEQ ID NO: 90

2.3. Target Sequence and PCR Primers for Amplification of TFRC

The target sequence for this example was a PCR amplicon from the TFRC gene generated by in vitro amplification of human genomic DNA, extracted from the IM9 cell line (Promega), using the oligonucleotide PCR primers listed below. The sequence in bold in the primer sequences corresponds to a universal tag (U1 or U2) that increases the Tm of the primer without affecting the specificity of the primer to the gene target. This tag improves amplification efficiency in PCR reactions. Primer sequences are listed 5' to 3'.

Forward primer 5TFRC_U1:
GCTAAAACAATAACTCAGAACTTACG
SEQ ID NO: 91

Reverse primer 3TFRC_U2:
CAGCTTTCTGAGGTTACCATCCTA
SEQ ID NO: 92

2.4. Reaction Components: Amplification and Quantification of Target Sequence

Real-time PCR amplification and detection of the target sequence was performed in a total reaction volume of 25 µL. All reactions were conducted in a CFX96 Real-Time PCR Detection System (Bio-Rad). Reactions were set up with substrates and their associated partzymes as in Table 8. The cycling parameters were, 95° C. for 2 minutes, 50 cycles of 95° C. for 15 seconds and 58° C. for 60 seconds (data collected at the 58° C. step). Each set of reaction conditions were run in duplicate and contained 40 nM 5TFRC_U1, 200 nM of 3TFRC_U2, 200 nM each of partzyme A and partzyme B, 200 nM substrate, 8 mM $MgCl_2$, 200 µM of each dNTP, 10 units RiboSafe RNase inhibitor (Bioline), 1× Immobuffer (Bioline), 2 units of MyTaqHS™ DNA polymerase (Bioline) and either genomic DNA template (50 ng) or no target (NF-$H_2O$).

TABLE 8

Partzyme combinations used for each universal substrate

| Substrate | Partzyme A | Partzyme B |
|---|---|---|
| Sub2 | TFRCA/2-P | TFRCB/2-P |
| SEQ ID NO: 21 | SEQ ID NO: 34 | SEQ ID NO: 35 |
| Sub3 | TFRCA/3-P | TFRCB/3-P |
| SEQ ID NO: 22 | SEQ ID NO: 36 | SEQ ID NO: 37 |
| Sub6 | TFRCA/6-P | TFRCB/6-P |
| SEQ ID NO: 23 | SEQ ID NO: 38 | SEQ ID NO: 39 |
| Sub44 | TFRCA/44 | TFRCB/44-P |
| SEQ ID NO: 25 | SEQ ID NO: 40 | SEQ ID NO: 41 |
| Sub45 | TFRCA/45-P | TFRCB/45-P |
| SEQ ID NO: 26 | SEQ ID NO: 42 | SEQ ID NO: 43 |
| Sub46 | TFRCA/46-P | TFRCB/46-P |
| SEQ ID NO: 27 | SEQ ID NO: 44 | SEQ ID NO: 45 |
| Sub55 | TFRCA/55-P | TFRCB/46-P |
| SEQ ID NO: 29 | SEQ ID NO: 46 | SEQ ID NO: 45 |
| Sub60T | TFRCA/60-P | TFRCB/60-P |
| SEQ ID NO: 72 | SEQ ID NO: 48 | SEQ ID NO: 49 |
| Sub61 | TFRCA/61-P | TFRCB/61-P |
| SEQ ID NO: 73 | SEQ ID NO: 50 | SEQ ID NO: 51 |
| Sub65 | TFRCA/65-P | TFRCB/61-P |
| SEQ ID NO: 74 | SEQ ID NO: 52 | SEQ ID NO: 51 |
| Sub72 | TFRCA/6-P | TFRCB/72-P |
| SEQ ID NO: 75 | SEQ ID NO: 38 | SEQ ID NO: 55 |
| Sub73 | TFRCA/73-P | TFRCB/73-P |
| SEQ ID NO: 76 | SEQ ID NO: 56 | SEQ ID NO: 57 |
| Sub74 | TFRCA/74-P | TFRCB/74-P |
| SEQ ID NO: 77 | SEQ ID NO: 58 | SEQ ID NO: 59 |
| Sub75 | TFRCA/75-P | TFRCB/75-P |
| SEQ ID NO: 78 | SEQ ID NO: 60 | SEQ ID NO: 61 |
| Sub77 | TFRCA/77-P | TFRCB/77-P |
| SEQ ID NO: 79 | SEQ ID NO: 62 | SEQ ID NO: 63 |
| Sub79 | TFRCA/79-P | TFRCB/79-P |
| SEQ ID NO: 80 | SEQ ID NO: 64 | SEQ ID NO: 65 |
| Sub80 | TFRCA/80-P | TFRCB/80-P |
| SEQ ID NO: 81 | SEQ ID NO: 66 | SEQ ID NO: 67 |
| Sub82 | TFRCA/77-P | TFRCB/82-P |
| SEQ ID NO: 82 | SEQ ID NO: 62 | SEQ ID NO: 68 |
| Sub83 | TFRCA/83-P | TFRCB/83-P |
| SEQ ID NO: 83 | SEQ ID NO: 69 | SEQ ID NO: 70 |
| Sub84 | TFRCA/55-P | TFRCB/72-P |
| SEQ ID NO: 84 | SEQ ID NO: 46 | SEQ ID NO: 55 |
| Sub85 | TFRCA/55-P | TFRCB/74-P |
| SEQ ID NO: 85 | SEQ ID NO: 46 | SEQ ID NO: 59 |
| Sub86 | TFRCA/6-P | TFRCB/46-P |
| SEQ ID NO: 86 | SEQ ID NO: 38 | SEQ ID NO: 45 |
| Sub87 | TFRCA/74-P | TFRCB/46-P |
| SEQ ID NO: 87 | SEQ ID NO: 58 | SEQ ID NO: 45 |
| Sub88 | TFRCA/77-P | TFRCB/46-P |
| SEQ ID NO: 88 | SEQ ID NO: 62 | SEQ ID NO: 45 |
| Sub89 | TFRCA/55-P | TFRCB/77-P |
| SEQ ID NO: 89 | SEQ ID NO: 46 | SEQ ID NO: 63 |
| Sub90 | TFRCA/90-P | TFRCB/82-P |
| SEQ ID NO: 90 | SEQ ID NO: 71 | SEQ ID NO: 68 |

2.5. Results: Amplification of Target and Cleavage of Reporter Substrate

Each MNAzyme qPCR reaction containing human genomic DNA showed an increase in fluorescence over time for the real-time detection of TFRC from human genomic DNA. For all reactions the fluorescence of the no-DNA target control was lower than that in the DNA target-containing reactions. This demonstrates that the increase in fluorescence produced in target-containing reactions is due to target dependent assembly of catalytically active MNAzymes that then cleaved one of the universal reporter substrates.

Comparison of the Ct values for each universal substrate (FIG. 5 and Table 9) show the series 1 substrates (Sub2, Sub3 and Sub6) and series 2 substrates (Sub44, Sub45, Sub46 and Sub60T) all have Ct values>27, whereas the other series 2 and all series 3 substrates tested (Sub55, Sub61, Sub65, Sub72, Sub73, Sub74, Sub75, Sub77, Sub79, Sub80, Sub82, Sub83, Sub84, Sub85, Sub86, Sub87, Sub88, Sub89 and Sub90) had Ct values less than 27. This indicates that the latter series 2 universal substrate and all series 3 universal substrates tested showed increased efficiency of the MNAzyme cleavage reaction at a higher annealing/detection temperature than that previously possible for MNAzyme qPCR. This improved efficiency of cleavage now permits efficient and robust detection of target using MNAzyme qPCR at a higher temperature than previously possible. This may also prove beneficial when using DNA polymerase formulations that require a higher temperature for amplification.

Of note is the importance of the nature of the nucleotide sequence of these efficiently cleaved substrates and the proximity of specific nucleotides to the ribonucleotides of the substrates. These features form the basis of a set of guidelines that result in universal substrates with a higher probability of being cleaved efficiently at elevated temperatures. These design guidelines include but are not limited to (not all may be necessary): (i) seven or more cytosine nucleotides in the ten bases surrounding the ribonucleotides ($N_4$-$N_{13}$); (ii) the bases immediately adjacent to the ribonucleotides are cytosines ($N_8$ and $N_9$); (iii) total content of substrate has >64% pyrimidine's; (iv) total Tm of the oligonucleotide is 66° C. or greater (where this latter guideline is only applicable if the reaction temperature for substrate cleavage is above 50° C.) (Table 9). In addition, it was observed that a low number of guanine nucleotides (e.g. three, two, one or none) in the 10 bases surrounding the ribonucleotides is also beneficial.

Figure 5:
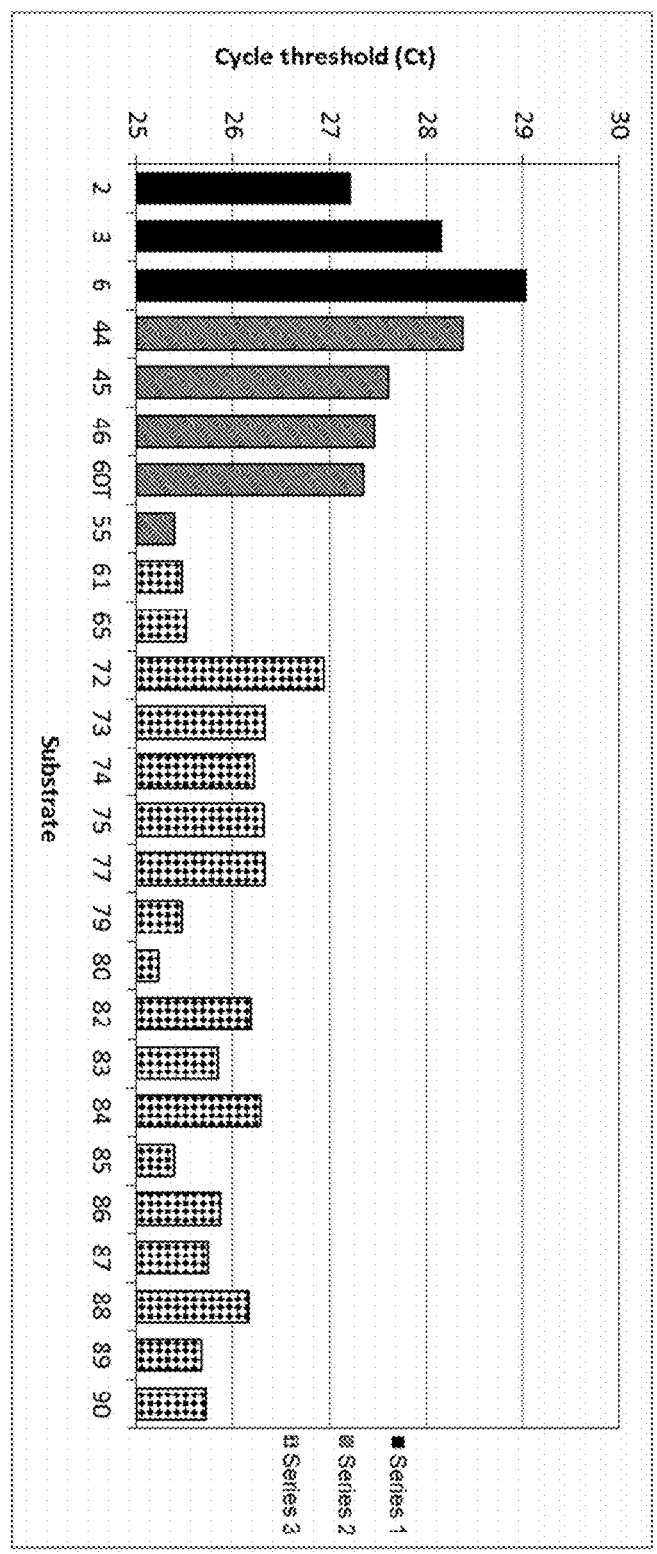
FIG. 5 provides a graph illustrating Ct values generated by MNAzyme qPCR using a range of different universal substrates for detection of the human TFRC gene. The identity of the universal substrates used in reactions are indicated on the x-axis (where "2" refers to Sub2, "3" refers to Sub3 etc.). The same primer set and genomic DNA were used for all reactions, and all partzymes had the same target-sensor regions and catalytic domains. The only differences between reactions were the substrate-sensor arms of the partzymes and the fluorescently labelled universal substrates. Thus the difference in Ct values between reactions is correlated with efficiency of cleavage of the universal substrates. Lower Ct values indicate a faster number of cycles to achieve a threshold level of fluorescence, and therefore indicate more efficiently cleaved universal substrates.

All universal substrates in FIG. 5 that had at Ct<27 at an annealing temperature of 58° C. obeyed three or more of these design guidelines (Table 9).

TABLE 9

Efficiency of cleavage of universal substrates (listed in order of cleavage efficiency based on Ct)

| Name | Sequence^ | # C's $N_4$-$N_{13}$ | CguC | % C/T+ | Tm* | Ct | #(i - iv)⁻ |
|---|---|---|---|---|---|---|---|
| Sub80 | AACCGCCCTCguCCCGTGAACC<br>SEQ ID NO: 81 | 7 | Yes | 65 | 70 | 25.2 | 4 |
| Sub55 | ACCGCACCTCguCCCCAGCTC<br>SEQ ID NO: 29 | 7 | Yes | 74 | 68 | 25.4 | 4 |
| Sub85 | ACCGCACCTCguCCCCTCCCAG<br>SEQ ID NO: 85 | 7 | Yes | 75 | 72 | 25.4 | 4 |
| Sub79 | TCCTCTCCCCguCCCCTCCTACC<br>SEQ ID NO: 80 | 8 | Yes | 90 | 72 | 25.5 | 4 |
| Sub61 | CTCGACCCCguCTCCACGCCA<br>SEQ ID NO: 73 | 7 | Yes | 74 | 68 | 25.5 | 4 |
| Sub65 | TCTCGACCTCguCTCCACGCCA<br>SEQ ID NO: 74 | 6 | Yes | 75 | 68 | 25.5 | 3 |
| Sub89 | ACCGCACCTCguCCCTCCTCCT<br>SEQ ID NO: 89 | 7 | Yes | 85 | 70 | 25.7 | 4 |
| Sub90 | CTCGACCCTCguCCCTCGTCCA<br>SEQ ID NO: 90 | 8 | Yes | 80 | 70 | 25.7 | 4 |
| Sub87 | ATCACTCCCCguCCCCAGCTC<br>SEQ ID NO: 87 | 8 | Yes | 79 | 66 | 25.7 | 4 |
| Sub83 | TCCGCTCCCCguCCCCTGCAAC<br>SEQ ID NO: 83 | 8 | Yes | 80 | 72 | 25.8 | 4 |
| Sub86 | ATCACGCCTCguCCCCAGCTC<br>SEQ ID NO: 86 | 7 | Yes | 74 | 66 | 25.9 | 4 |
| Sub88 | CTCCTCCCTCguCCCCAGCTC<br>SEQ ID NO: 88 | 8 | Yes | 89 | 68 | 26.2 | 4 |
| Sub82 | CTCCTCCCTCguCCCTCGTCCA<br>SEQ ID NO: 82 | 8 | Yes | 90 | 70 | 26.2 | 4 |
| Sub74 | ATCACTCCCCguCCCCTCCCAG<br>SEQ ID NO: 77 | 8 | Yes | 80 | 70 | 26.2 | 4 |
| Sub84 | ACCGCACCTCguCTCCTCCCAG<br>SEQ ID NO: 84 | 6 | Yes | 75 | 70 | 26.3 | 3 |
| Sub75 | TGACCCTCCTCguCTCCCCACTA<br>SEQ ID NO: 78 | 7 | Yes | 81 | 70 | 26.3 | 4 |
| Sub73 | TGGCGTCCCCguCCCCTCGTG<br>SEQ ID NO: 76 | 8 | Yes | 74 | 70 | 26.3 | 4 |

TABLE 9-continued

Efficiency of cleavage of universal substrates (listed in order of cleavage efficiency based on Ct)

| Name | Sequence^ | # C's $N_4$-$N_{13}$ | CguC | % C/T+ | Tm* | Ct | #(i - iv)~ |
|---|---|---|---|---|---|---|---|
| Sub77 | CTCCTCCCTCguCCCTCCTCCT SEQ ID NO: 79 | 8 | Yes | 100 | 70 | 263 | 4 |
| Sub72 | ATCACGCCTCguCTCCTCCCAG SEQ ID NO: 75 | 6 | Yes | 75 | 68 | 26.9 | 3 |
| Sub2 | AAGGTTTCCTCguCCCTGGGCA SEQ ID NO: 21 | 6 | Yes | 60 | 66 | 27.2 | 2 |
| Sub60T§ | TGCCAACCACguCCAACACGAC SEQ ID NO: 72 | 6 | Yes | 53 | 64 | 273 | 2 |
| Sub46 | ACCGCACCTguCCCCAGCTC SEQ ID NO: 27 | 7 | No | 72 | 64 | 27.5 | 2 |
| Sub45 | ACGGGTCCCguCTCCTTTGGAA SEQ ID NO: 26 | 6 | Yes | 60 | 66 | 27.6 | 2 |
| Sub3 | CAGCACAACCguCACCAACCG SEQ ID NO: 22 | 6 | Yes | 53 | 64 | 28.2 | 1 |
| Sub44 | CAGGTCTCCTCguCCCTATAGTGA SEQ ID NO: 25 | 6 | Yes | 64 | 70 | 28.4 | 2 |
| Sub6 | ATCACGCCTCguTCCTCCCAG SEQ ID NO: 23 | 6 | No | 74 | 64 | 29.0 | 1 |

^uppercase bases represent DNA and lowercase bases represent RNA and position of base in a substrate is represented by $(N_x)$-$N_1$-$N_2$-$N_3$-$N_4$-$N_5$-$N_6$-$N_7$-$N_8$-rR-rY-$N_9$-$N_{10}$-$N_{11}$-$N_{12}$-$N_{13}$-$N_{14}$-$N_{15}$-$(N_x)$
+% C/T (pyrimidines) of sequence length shown above for each substrate, does not include ribonucleotides
*Tm given here equates to the melting temperature of the bound bases calculated using the Wallace rule - only calculated for bases that hybridize to their complement. When the substrate is bound to the MNAzyme based on the 10-23 DNAzyme the "g" ribonucleotide remains unbound therefore does not contribute to the overall bound Tm.
~The number of the design guidelines (i), (ii), (iii) and/or (iv) that have been met by the substrate sequence.
§The additional "T" in Sub6OT is not bound by a partzyme arm and is therefore not included in the calculations of % C/T and Tm.

Example 3

Use of Universal Substrates with MNAzymes in a Format for Direct Detection of a Nucleic Acid Target Investigation into efficiency of cleavage of substrates based on the performance of the series 1 and 2 substrates, lead to the development of guidelines to aid in designing a third round of substrates, series 3. These guidelines included but were not limited to (i) seven or more cytosine nucleotides in the ten bases surrounding the ribonucleotides ($N_4$-$N_{13}$), (ii) bases immediately adjacent to the ribonucleotides are cytosines ($N_8$ and $N_9$) (iii) total content of substrate has >64% pyrimidines and (iv) total Tm of the oligonucleotide is 66° C. or greater (where this latter guideline is only applicable if the reaction temperature for substrate cleavage is above 50° C.).

MNAzymes can be used to directly detect target nucleic acids in an isothermal reaction without any target amplification. This method of direct target detection can be used to assess the efficiency of cleavage of substrates. Partzymes were designed to test the efficiency of cleavage of a range of universal substrates when coupled with direct detection of the gene TFRC at a range of temperatures. In this example, the previously known series 1 universal substrates (Sub2, Sub3, and Sub6) were compared to the series 2 universal substrates (Sub44, Sub45, Sub46, Sub49, Sub55 and Sub60T) and series 3 substrates (Sub61, Sub65, Sub72, Sub73, Sub74, Sub75, Sub77, Sub79, Sub80, Sub82, Sub83, Sub84, Sub85, Sub86, Sub87, Sub88, Sub89 and Sub90) to determine if the design guidelines derived from analyses of series 1 and 2 substrates would be useful in the development of series 3 substrates that are cleaved with the same or a higher level of activity as substrates from series 1 and 2. The level of cleavage efficiency was determined by calculating the signal to noise ratio (from results of a "test" reaction containing template and a no template control reaction) after 10 minutes over a temperature range of 52, 54, 56 and 58° C. The standard deviation of the signal to noise ratios over this temperature range was also calculated as a measure of robustness of the substrates with regards to temperature.

3.1. Partzyme Oligonucleotides

In the experiments conducted to measure the cleavage efficiency of series 1, 2 and 3 universal substrates described in Tables 4 and 5 using direct target detection, all the partzyme oligonucleotides A and B were designed with sensor arms complementary to the same sequence of the human TFRC gene. The sequences of the A and B partzymes are listed below from 5' to 3', where the bases underlined hybridize to the substrate. The "-P" indicates 3' phosphorylation of the oligonucleotide.

SEQ ID NO: 34
partzyme A TFRCA/2-P:
GGAATATGGAAGGAGACTGTCACAACGAGAGGAAACCTT

SEQ ID NO: 35
partzyme B TFRCB/2-P:
TGCCCAGGGAGGCTAGCTCCTCTGACTGGAAAACAGACT

SEQ ID NO: 36
partzyme A TFRCA/3-P:
GGAATATGGAAGGAGACTGTCACAACGAGGTTGTGCTG

SEQ ID NO: 37
partzyme B TFRCB/3-P:
CGGTTGGTGAGGCTAGCTCCTCTGACTGGAAAACAGACT

SEQ ID NO: 38
partzyme A TFRCA/6-P:
GGAATATGGAAGGAGACTGTCACAACGAGAGGCGTGAT

SEQ ID NO: 39
partzyme B TFRCB/6-P:
CTGGGAGGAAGGCTAGCTCCTCTGACTGGAAAACAGACT

SEQ ID NO: 40
partzyme A TFRCA/44-P:
GGAATATGGAAGGAGACTGTCACAACGAGAGGAGACCTG

SEQ ID NO: 41
partzyme B TFRCB/44-P:
TCACTATAGGGAGGCTAGCTCCTCTGACTGGAAAACAGACT

SEQ ID NO: 42
partzyme A TFRCA/45-P:
GGAATATGGAAGGAGACTGTCACAACGAGGGACCCGT

SEQ ID NO: 43
partzyme B TFRCB/45-P:
TTCCAAAGGAGAGGCTAGCTCCTCTGACTGGAAAACAGACT

SEQ ID NO: 44
partzyme A TFRCA/46-P:
GGAATATGGAAGGAGACTGTCACAACGAAGGTGCGGT

SEQ ID NO: 45
partzyme B TFRCB/46-P:
GAGCTGGGGAGGCTAGCTCCTCTGACTGGAAAACAGACT

SEQ ID NO: 93
partzyme A TFRCA/49-P:
GGAATATGGAAGGAGACTGTCACAACGAGAGCCAAGTTTA

SEQ ID NO: 94
partzyme B TFRCB/49-P:
TATCACAGCCAAGGCTAGCTCCTCTGACTGGAAAACAGACT

SEQ ID NO: 46
partzyme A TFRCA/55-P:
GGAATATGGAAGGAGACTGTCACAACGAGAGGTGCGGT

SEQ ID NO: 48
partzyme A TFRCA/60-P:
GGAATATGGAAGGAGACTGTCACAACGAGTGGTTGGC

SEQ ID NO: 49
partzyme B TFRCB/60-P:
GTCGTGTTGGAGGCTAGCTCCTCTGACTGGAAAACAGACT

SEQ ID NO: 50
partzyme A TFRCA/61-P:
GGAATATGGAAGGAGACTGTCACAACGAGGGGTCGAG

SEQ ID NO: 51
partzyme B TFRCB/61-P:
TGGCGTGGAGAGGCTAGCTCCTCTGACTGGAAAACAGACT

SEQ ID NO: 52
partzyme A TFRCA/65-P:
GGAATATGGAAGGAGACTGTCACAACGAGAGGTCGAGA

SEQ ID NO: 55
partzyme B TFRCB/72-P:
CTGGGAGGAGAGGCTAGCTCCTCTGACTGGAAAACAGACT

SEQ ID NO: 56
partzyme A TFRCA/73-P:
GGAATATGGAAGGAGACTGTCACAACGAGGGGACGCCA

SEQ ID NO: 57
partzyme B TFRCB/73-P:
CACGAGGGGAGGCTAGCTCCTCTGACTGGAAAACAGACT

SEQ ID NO: 58
partzyme A TFRCA/74-P:
GGAATATGGAAGGAGACTGTCACAACGAGGGGAGTGAT

SEQ ID NO: 59
partzyme B TFRCB/74-P:
CTGGGAGGGGAGGCTAGCTCCTCTGACTGGAAAACAGACT

SEQ ID NO: 60
partzyme A TFRCA/75-P:
GGAATATGGAAGGAGACTGTCACAACGAGAGGAGGGTCA

SEQ ID NO: 61
partzyme B TFRCB/75-P:
TAGTGGGGAGAGGCTAGCTCCTCTGACTGGAAAACAGACT

SEQ ID NO: 62
partzyme A TFRCA/77-P:
GGAATATGGAAGGAGACTGTCACAACGAGAGGGAGGAG

SEQ ID NO: 63
partzyme B TFRCB/77-P:
AGGAGGAGGGAGGCTAGCTCCTCTGACTGGAAAACAGACT

SEQ ID NO: 64
partzyme A TFRCA/79-P:
GGAATATGGAAGGAGACTGTCACAACGAGGGGAGAGGA

SEQ ID NO: 65
partzyme B TFRCB/79-P:
GGTTGAAGGGGAGGCTAGCTCCTCTGACTGGAAAACAGACT

SEQ ID NO: 66
partzyme A TFRCA/80-P:
GGAATATGGAAGGAGACTGTCACAACGAGAGGGCGGTT

SEQ ID NO: 67
partzyme B TFRCB/80-P:
GGTTCACGGGAGGCTAGCTCCTCTGACTGGAAAACAGACT

SEQ ID NO: 68
partzyme B TFRCB/82-P:
TGGACGAGGGAGGCTAGCTCCTCTGACTGGAAAACAGACT

SEQ ID NO: 69
partzyme A TFRCA/83-P:
GGAATATGGAAGGAGACTGTCACAACGAGGGGAGCGGA

SEQ ID NO: 70
partzyme B TFRCB/83-P:
GTTGCAGGGGAGGCTAGCTCCTCTGACTGGAAAACAGACT

SEQ ID NO: 71
partzyme A TFRCA/90-P:
GGAATATGGAAGGAGACTGTCACAACGAGAGGGTCGAG 3.2. Reporter Substrates The reporter substrates for this example are shown below with the sequence, 5' to 3'. The lower case bases represent RNA and the upper case bases represent DNA. In the current example, the substrates were end labelled with a 6-FAM moiety at the 5' end (indicated by a "F" in the name of the substrates below) and an Iowa Black® FQ quencher moiety at the 3' end (indicated by an "IB" in the name of the substrates below). Cleavage of the substrates was monitored between 510-530 nm (FAM emission wavelength range on CFX96 (BioRad)) with excitation between 450-490 nm (FAM excitation wavelength range on CFX96 (BioRad)).

```
Sub2-FIB:                           SEQ ID NO: 21
AAGGTTTCCTCguCCCTGGGCA

Sub3-FIB:                           SEQ ID NO: 22
CAGCACAACCguCACCAACCG

Sub6-FIB:                           SEQ ID NO: 23
ATCACGCCTCguTCCTCCCAG

Sub44-FIB:                          SEQ ID NO: 25
CAGGTCTCCTCguCCCTATAGTGA

Sub45-FIB:                          SEQ ID NO: 26
ACGGGTCCCguCTCCTTTGGAA

Sub46-FIB:                          SEQ ID NO: 27
ACCGCACCTguCCCCAGCTC

Sub49-FB:                           SEQ ID NO: 28
TAAACTTGGCTCguTGGCTGTGATA

Sub55-FIB:                          SEQ ID NO: 29
ACCGCACCTCguCCCCAGCTC

Sub60T-FIB:                         SEQ ID NO: 72
TGCCAACCACguCCAACACGAC

Sub61-FIB:                          SEQ ID NO: 73
CTCGACCCCguCTCCACGCCA

Sub65-FIB:                          SEQ ID NO: 74
TCTCGACCTCguCTCCACGCCA

Sub72-FIB:                          SEQ ID NO: 75
ATCACGCCTCguCTCCTCCCAG

Sub73-FIB:                          SEQ ID NO: 76
TGGCGTCCCCguCCCCTCGTG

Sub74-FIB:                          SEQ ID NO: 77
ATCACTCCCCguCCCCTCCCAG

Sub75-FIB:                          SEQ ID NO: 78
TGACCCTCCTCguCTCCCCACTA

Sub77-FIB:                          SEQ ID NO: 79
CTCCTCCCTCguCCCTCCTCCT

Sub79-FIB:                          SEQ ID NO: 80
TCCTCTCCCCguCCCCTTCAACC

Sub80-FIB:                          SEQ ID NO: 81
AACCGCCCTCguCCCGTGAACC

Sub82-FIB:                          SEQ ID NO: 82
CTCCTCCCTCguCCCTCGTCCA

Sub83-FIB:                          SEQ ID NO: 83
TCCGCTCCCCguCCCCTGCAAC

Sub84-FIB:                          SEQ ID NO: 84
ACCGCACCTCguCTCCTCCCAG

Sub85-FIB:                          SEQ ID NO: 85
ACCGCACCTCguCCCCTCCCAG

Sub86-FIB:                          SEQ ID NO: 86
ATCACGCCTCguCCCCAGCTC

Sub87-FIB:                          SEQ ID NO: 87
ATCACTCCCCguCCCCAGCTC

Sub88-FIB:                          SEQ ID NO: 88
CTCCTCCCTCguCCCCAGCTC

Sub89-FIB:                          SEQ ID NO: 89
ACCGCACCTCguCCCTCCTCCT

Sub90-FIB:                          SEQ ID NO: 90
CTCGACCCTCguCCCTCGTCCA
```

3.3. Target Sequence

The target sequence for this example was a synthetic oligonucleotide AF-TFRC with the sequence, 5' to 3' below. This target sequence has the same sequence as a section of the TFRC gene.

```
                                    SEQ ID NO: 95
Assembly Facilitator AF-TFRC:
AGTCTGTTTTCCAGTCAGAGGGACAGTCTCCTTCCATATTCC
```

3.4. Reaction Components: Direct Isothermal Detection of Target Sequence

Detection of the target sequence was measured by an increase in fluorescent signal caused by, cleavage of the reporter substrate by the catalytically active MNAzyme. The total volume of all reactions was 25 μL and all reactions were conducted on the CFX96™ Real-Time PCR Detection Systems (BioRad), with each combination of partzymes and substrates (Table 10) being tested at 52° C., 54° C., 56° C., 58° C. and 60° C. Fluorescence for each reaction was programmed to be read after 1 second for the first 50 cycles and then programmed to be read after 25 seconds for the next 50 cycles. All reactions contained 1×PCR Buffer II (Applied Biosystems), 10 mM MgCl$_2$, and 0.2 μM of Partzymes A and B and 0.2 μM substrate (tested in combinations as in Table 10). Each reaction was performed in duplicate as either a "test" with 10 nM target sequence (AF-TFRC) or no-template control (NF-H$_2$O).

TABLE 10

| Partzyme combinations used for each substrate | | |
|---|---|---|
| Substrate | Partzyme A | Partzyme B |
| Sub2 | TFRCA/2-P | TFRCB/2-P |
| SEQ ID NO: 21 | SEQ ID NO: 34 | SEQ ID NO: 35 |
| Sub3 | TFRCA/3-P | TFRCB/3-P |
| SEQ ID NO: 22 | SEQ ID NO: 36 | SEQ ID NO: 37 |
| Sub6 | TFRCA/6-P | TFRCB/6-P |
| SEQ ID NO: 23 | SEQ ID NO: 38 | SEQ ID NO: 39 |
| Sub44 | TFRCA/44 | TFRCB/44-P |
| SEQ ID NO: 25 | SEQ ID NO: 40 | SEQ ID NO: 41 |

TABLE 10-continued

Partzyme combinations used for each substrate

| Substrate | Partzyme A | Partzyme B |
|---|---|---|
| Sub45 | TFRCA/45-P | TFRCB/45-P |
| SEQ ID NO: 26 | SEQ ID NO: 42 | SEQ ID NO: 43 |
| Sub46 | TFRCA/46-P | TFRCB/46-P |
| SEQ ID NO: 27 | SEQ ID NO: 44 | SEQ ID NO: 45 |
| Sub49 | TFRCA/49-P | TFRCB/49-P |
| SEQ ID NO: 28 | SEQ ID NO: 93 | SEQ ID NO: 94 |
| Sub55 | TFRCA/55-P | TFRCB/46-P |
| SEQ ID NO: 29 | SEQ ID NO: 46 | SEQ ID NO: 45 |
| Sub60T | TFRCA/60-P | TFRCB/60-P |
| SEQ ID NO: 72 | SEQ ID NO: 48 | SEQ ID NO: 49 |
| Sub61 | TFRCA/61-P | TFRCB/61-P |
| SEQ ID NO: 73 | SEQ ID NO: 50 | SEQ ID NO: 51 |
| Sub65 | TFRCA/65-P | TFRCB/61-P |
| SEQ ID NO: 74 | SEQ ID NO: 52 | SEQ ID NO: 51 |
| Sub72 | TFRCA/6-P | TFRCB/72-P |
| SEQ ID NO: 75 | SEQ ID NO: 38 | SEQ ID NO: 55 |
| Sub73 | TFRCA/73-P | TFRCB/73-P |
| SEQ ID NO: 76 | SEQ ID NO: 56 | SEQ ID NO: 57 |
| Sub74 | TFRCA/74-P | TFRCB/74-P |
| SEQ ID NO: 77 | SEQ ID NO: 58 | SEQ ID NO: 59 |
| Sub75 | TFRCA/75-P | TFRCB/75-P |
| SEQ ID NO: 78 | SEQ ID NO: 60 | SEQ ID NO: 61 |
| Sub77 | TFRCA/77-P | TFRCB/77-P |
| SEQ ID NO: 79 | SEQ ID NO: 62 | SEQ ID NO: 63 |
| Sub79 | TFRCA/79-P | TFRCB/79-P |
| SEQ ID NO: 80 | SEQ ID NO: 64 | SEQ ID NO: 65 |
| Sub80 | TFRCA/80-P | TFRCB/80-P |
| SEQ ID NO: 81 | SEQ ID NO: 66 | SEQ ID NO: 67 |
| Sub82 | TFRCA/77-P | TFRCB/82-P |
| SEQ ID NO: 82 | SEQ ID NO: 62 | SEQ ID NO: 68 |
| Sub83 | TFRCA/83-P | TFRCB/83-P |
| SEQ ID NO: 83 | SEQ ID NO: 69 | SEQ ID NO: 70 |
| Sub84 | TFRCA/55-P | TFRCB/72-P |
| SEQ ID NO: 84 | SEQ ID NO: 46 | SEQ ID NO: 55 |
| Sub85 | TFRCA/55-P | TFRCB/74-P |
| SEQ ID NO: 85 | SEQ ID NO: 46 | SEQ ID NO: 59 |
| Sub86 | TFRCA/6-P | TFRCB/46-P |
| SEQ ID NO: 86 | SEQ ID NO: 38 | SEQ ID NO: 45 |
| Sub87 | TFRCA/74-P | TFRCB/46-P |
| SEQ ID NO: 87 | SEQ ID NO: 58 | SEQ ID NO: 45 |
| Sub88 | TFRCA/77-P | TFRCB/46-P |
| SEQ ID NO: 88 | SEQ ID NO: 62 | SEQ ID NO: 45 |
| Sub89 | TFRCA/55-P | TFRCB/77-P |
| SEQ ID NO: 89 | SEQ ID NO: 46 | SEQ ID NO: 63 |
| Sub90 | TFRCA/90-P | TFRCB/82-P |
| SEQ ID NO: 90 | SEQ ID NO: 71 | SEQ ID NO: 68 |

3.5. Results: Direct Isothermal Detection of Target Sequence

Each reaction with each universal substrate showed an increase in fluorescence over time for reactions containing the synthetic template AF-TFRC (target sequence corresponding to a portion of the TFRC gene). For all substrates, the fluorescence of the no-template control was lower than that in the target sequence-containing reactions. This demonstrates that the increase in fluorescence produced in target-containing reactions is due to target dependent assembly of catalytically active MNAzymes that then cleaved the universal reporter substrate.

For each reaction, the raw fluorescent data points obtained from the CFX96 were normalised by dividing each data point by the value obtained for the paired no-template reaction at the first reading. This normalised data was then used to calculate the signal to noise value at approximately the 10 minute mark by dividing test data points by the no template data points. This calculation was performed for each substrate at each reaction temperature. The signal to noise value provides a measurement of the efficiency of the cleavage of substrates (FIG. 6, (i)), with a high signal to noise indicating efficient cleavage. The standard deviation of the signal to noise ratio for each substrate over the temperature range was also calculated and plotted to determine substrates with consistently high activity over the tested range of temperatures (FIG. 6, (ii)). A low value for this standard deviation indicates minimal change of signal to noise levels between temperatures. This suggests that these substrates are robust with respect to temperature.

Figure 6:
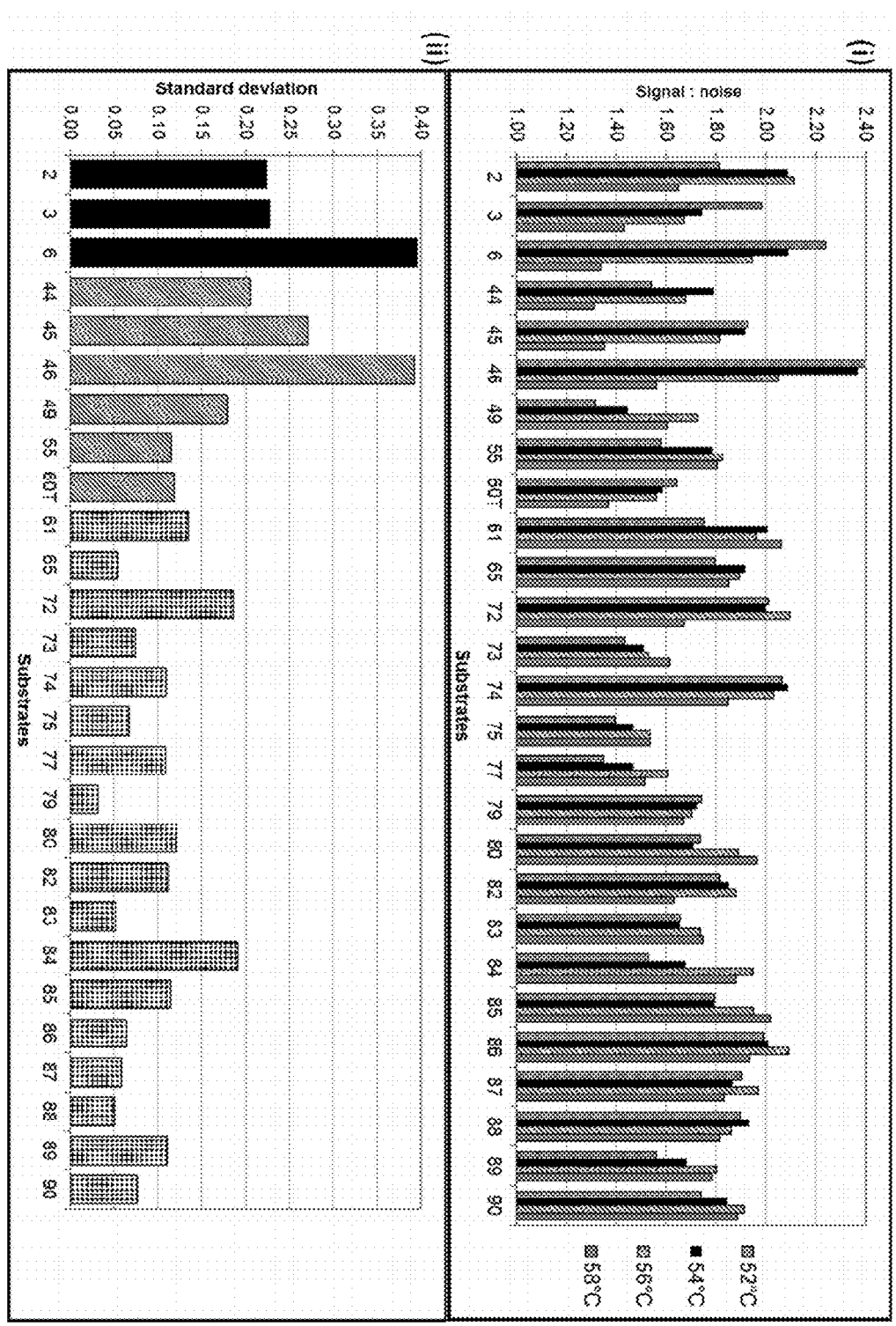
FIG. 6 provides graphs illustrating the signal to noise ratios resulting from MNAzyme mediated cleavage of a range of universal substrates in an isothermal format. Target was a synthetic oligonucleotide. The signal to noise ratio was calculated from normalized fluorescence data collected during cleavage reactions at a range of reaction temperatures. The identity of the universal substrates used in reactions are indicated on the x-axis (where "2" refers to Sub2, "3" refers to Sub3 etc.).

Analysis of the signal to noise ratio for each substrate at the range of temperatures (FIG. 6, (i)) shows that the series 1 substrates (Sub2, Sub3 and Sub6) had a higher signal to noise at the lower temperatures measured. However the cleavage efficiency of these substrates dropped dramatically as the reaction temperature was increased to 58° C. A similar pattern was seen for a subset of the series 2 substrates (Sub44, Sub45, Sub46, and Sub60T). The series 2 substrate, Sub49, performed poorly at the lower temperatures and slightly better at the higher but overall had lower signal to noise than other substrates. The series 2 substrate Sub60T showed a decrease in signal to noise with increasing temperature, and overall lower signal to noise at the lower temperatures than the majority of other series 1 and 2 substrates. The other series 2 substrate (Sub55), and a subset of the series 3 substrates (Sub61, Sub65, Sub74, Sub79, Sub80, Sub82, Sub83, Sub84, Sub85, Sub86, Sub87, Sub88, Sub89 and Sub90) displayed high fluorescence levels and hence were efficiency cleaved across all the temperatures tested. The series 3 substrates Sub73, Sub75 and Sub77 displayed roughly the same signal to noise value across the temperatures tested, however the overall signal to noise level was low. These three substrates all gave good results with relatively low Ct values when tested with MNAzyme qPCR (see Example 2). Comparison of the data for these substrates for Examples 2 and 3 may indicate that when a constant temperature in the range of 52 to 58° C. is used the turnover of these substrates is lower thus affecting the cleavage efficiency. This decreased substrate turnover could be related to the "off" rate of cleaved products. In Example 2, the cleaved products would dissociate from the partzyme substrate arms at least once a cycle when the temperature was increased to above 90° C. as part of the thermocycling profile of PCR.

Overall, the substrates that conform to the design guidelines (Table 9) showed a greater signal to noise ratio across the tested temperature range than the substrates that fell outside these guidelines (FIG. 6, (i)). More specifically reactions with Sub55, Sub61, Sub65, Sub72, Sub74, Sub79, Sub80, Sub82, Sub83, Sub84, Sub85, Sub86, Sub87, Sub88, Sub89 and Sub90 displayed high signal to noise values at every temperature tested demonstrating that these are robust substrates over a range of temperatures. This improvement was further evident when the standard deviation was calculated from the signal to noise ratio across the temperatures for each substrate (FIG. 6, (ii)). This measure of variability paired with the absolute values of signal to noise indicated that, over the temperature range tested, the series 2 substrate Sub55, and the series 3 substrates Sub61, Sub65, Sub74, Sub79, Sub80, Sub82, Sub83, Sub85, Sub86, Sub87 Sub88, Sub89 and Sub90, had a high signal to noise ratio with little variability across a broad temperature range. There were three series 3 substrates, Sub65, Sub72 and Sub84, that only match three of the four design guidelines and two of these, Sub72 and Sub84, had a slightly greater standard deviation of the signal to noise than the series 3 substrates that match all four of the design guidelines as specified in Table 9.

Substrates that had signal to noise values less than 1.6 at 3 or more temperatures (Sub60, Sub73, Sub75 and Sub77) were not considered robust with respect to the range of temperatures tested.

These data suggest that compliance with all four of these design guidelines (Table 9) will, in general, produce substrates that are cleaved efficiently and robustly over a range of temperatures.

A study of the sequence of the most successful substrates from series 2 and 3 shows that these substrates share common features. Substrates that have little variation between signal to noise ratios over the temperatures tested (FIG. 6, (i) and (ii)) generally contained seven or more cytosine nucleotides within the bases $N_4$ to $N_{13}$. This indicates that the core region, i.e. the 10 bases surrounding the ribonucleotides, is highly influential on substrate activity. In addition, it was observed that a low number of guanine nucleotides (e.g. three, two, one or none) in the 10 bases surrounding the ribonucleotides is also beneficial.

Example 4

Use of Universal Substrates with MNAzyme qPCR, at Annealing Temperatures of 52° C. and 58° C.

MNAzymes can be used to monitor amplification of target nucleic acids in real-time using in vitro target amplification methods such as PCR. Further, real-time monitoring during qPCR using MNAzyme substrates labelled with fluorophores and quencher pairs generates a curve that can indicate the efficiency of a reaction by its Ct value and steepness (reaction rate). In this example amplification and detection are performed in a one-step process, wherein PCR amplification and MNAzyme-mediated detection occur simultaneously in a single tube. The rate of production of signal (measured by Ct and steepness of reaction curves) at different annealing temperatures such as 52° C. and 58° C. (the temperature which data was collected), can be influenced by the sequence of the universal substrate.

The annealing/detection temperature for MNAzyme qPCR used in the art is between 50 and 54° C. This temperature was dictated by the fact that the universal substrates known in the art had a limitation on the temperature at which they were efficiently cleaved with 54° C. being the upper limit for the series 1 universal substrates. There is a need for universal substrates that cleave at higher temperatures to allow greater flexibility in design of primers and partzymes that anneal at higher temperatures. This design flexibility for primers and partzymes would be of great benefit for many applications such as genetic targets of interest that have high percentages of G and C bases in their sequence, requiring partzymes and primers with higher Tms for specific detection. Utility of universal substrates would be greatly increased if substrates existed that were efficiently cleaved at a range of temperatures between 52 and 58° C.

In this example, partzymes corresponding to series 1, 2 and 3 universal substrates, were designed to target a range of genes, as outlined in Table 11. One skilled in the art would appreciate that any gene sequence or gene transcript or any other nucleic acid amplification product could be used as a target as described here. Each combination of partzymes and their associated universal substrates were tested at annealing temperatures of 52° C. and 58° C. in qPCR. The results from this comparison will determine if series 1, 2 and 3 substrates targeted to different genes, and at different annealing temperatures allow the same, higher or lower level of cleavage efficiency in real-time PCR. The level of cleavage efficiency was determined by measuring the Ct value and looking at the steepness of reaction curves for reactions containing different universal substrates.

TABLE 11

Substrates used to detect different genes by MNAzyme qPCR

| Gene | Series 1 substrate | Series 2 substrate | Series 3 substrate |
| --- | --- | --- | --- |
| CYP2C9 | Sub3 | — | Sub61 |
| TP53 | Sub6 | — | Sub72, Sub74, and Sub79 |
| B2M | — | Sub60 | Sub61 and Sub79 |
| HMBS | — | Sub49 | Sub75 |
| TFRC | Sub2 | — | Sub72 and Sub80 |
| RPL13a | — | Sub55 | Sub80 and Sub88 |

4.1. Partzyme Oligonucleotides

In the experiments conducted to measure the efficiency of cleavage of the universal substrates in real-time PCR, the partzyme oligonucleotides A and B were designed with sensor arms complementary to the human CYP2C9, TP53, B2M, HMBS, RPL13a or TFRC genes. The sequences of the A and B partzymes are listed below from 5' to 3', where the bases underlined hybridize to the substrate. The "-P" indicates 3' phosphorylation of the oligonucleotide.

```
                                       SEQ ID NO: 96
partzyme A CYP2C9A/3-P:
GGGAAGAGGAGCATTGAGGAACAACGAGGTTGTGCTG SEQ ID NO: 97
partzynie B CYP2C9B/3-P:
CGGTTGGTGAGGCTAGCTCCGTGTTCAAGAGGAAGC SEQ ID NO: 98
partzyme A CYP2C9A/61-P:
GGGAAGAGGAGCATTGAGGAACAACGAGGGGTCGAG SEQ ID NO: 99
partzyme B CYP2C9B/61-P:
TGGCGTGGAGAGGCTAGCTCCGTGTTCAAGAGGAAGC SEQ ID NO: 100
partzyme A TP53A/6-P:
GACGGAACAGCTTTGAGGTGACAACGAGAGGCGTGAT SEQ ID NO: 101
partzyme B TP53B/6-P:
CTGGGAGGAAGGCTAGCTCGTGTTTGTGCCTGTCCTGG SEQ ID NO: 103
partzyme B TP53B/72-P:
CTGGGAGGAGAGGCTAGCTCGTGTTTGTGCCTGTCCTGG SEQ ID NO: 104
partzyme A TP53A/74-P:
GACGGAACAGCTTTGAGGTGACAACGAGGGGAGTGAT SEQ ID NO: 105
partzyme B TP53B/74-P:
CTGGGAGGGGAGGCTAGCTCGTGTTT.GTGCCTGTCCTGG SEQ ID NO: 106
partzyme A TP53A/79-P:
GACGGAACAGCTTTGAGGTGACAACGAGGGGAGAGGA SEQ ID NO: 107
partzyme B TP53B/79-P:
GGTTGAAGGGGAGGCTAGCTCGTGTTTGTGCCTGTCCTG&

SEQ ID NO: 108
partzyme A B2MA/60-P:
ATTCAGGTTTACTCACGTCATCACAACGAGTGGTTGGC
```

-continued

SEQ ID NO: 109
partzyme B B2MB/60-P:
GTCGTGTTGGAGGCTAGCTCAGCAGAGAATGGAAAGTCAAA

SEQ ID NO: 110
partzyme A B2MA/61-P
ATTCAGGTTTACTCACGTCATCACAACGAGGGGTCGAG

SEQ ID NO: 111
partzyme B B2MB/61-P
TGGCGTGGAGAGGCTAGCTCAGCAGAGAATGGAAAGTCAAA

SEQ ID NO: 112
partzyme A B2MA/79-P
ATTCAGGTTTACTCACGTCATCACAACGAGGGAGAGGA

SEQ ID NO: 113
partzyme B B2MB/79-P
GGTTGAAGGGGAGGCTAGCTCAGCAGAGAATGGAAAGTCAAA

SEQ ID NO: 114
partzyme A HMBSA/49-P:
GCCATGTCTGGTAACGGCAAACAACGAGAGCCAAGTTTA

SEQ ID NO: 115
partzyme B HMBSB/49-P:
TATCACAGCCAAGGCTAGCTTGCGGCTGCAACGGCGGTG

SEQ ID NO: 116
partzyme A HMBSA/75-P:
GCCATGTCTGGTAACGGCAAACAACGAGAGGAGGGTCA

SEQ ID NO: 117
partzyme B HMBSB/75-P:
TAGTGGGGAGAGGCTAGCTTGCGGCTGCAACGGCGGTG

SEQ ID NO: 34
partzyme A TFRCA/2-P:
GGAATATGGAAGGAGACTGTCACAACGAGAGGAAACTT

SEQ ID NO: 35
partzyme B TFRCB/2-P:
TGCCCAGGGAGGCTAGCTCCTCTGACTGGAAAACAGACT

SEQ ID NO: 38
partzyme A TFRCA/72-P:
GGAATATGGAAGGAGACTGTCACAACGAGAGGCGTGAT

SEQ ID NO: 55
partzyme B TFRCB/72-P:
CTGGGAGGAGAGGCTAGCTCCTCTGACTGGAAAACAGACT

SEQ ID NO: 66
partzyme A TFRCA/80-P:
GGAATATGGAAGGAGACTGTCACAACGAGAGGGCGGTT

SEQ ID NO: 67
partzyme B TFRCB/80-P:
GGTTCACGGGAGGCTAGCTCCTCTGACTGGAAAACAGACT

SEQ ID NO: 118
partzyme A RPL13aA/55-P
TTGACAAATACACAGAGGTCACAACGAGAGGTGCGGT

SEQ ID NO: 119
partzyme B RPL13aB/55-P
GAGCTGGGGAGGCTAGCTCTCAAGACCCACGGACTCCT

SEQ ID NO: 120
partzyme A RPL13aA/80-P
AATTGACAAATACACAGAGGTCACAACGAGAGGGCGGTT

SEQ ID NO: 121
partzyme B RPL13aB/80-P
GGTTCACGGGAGGCTAGCTCTCAAGACCCACGGACTCCT

SEQ ID NO: 122
partzyme A RPL13aA/88-P
AATTGACAAATACACAGAGGTCACAACGAGAGGGAGGAG 4.2. Reporter Substrates In the current example, the substrates were 5' end labelled with a fluorophore and 3' end labelled with a quencher moiety. Table 12 depicts the Substrate—fluorophore/quencher combinations. Some substrates were tested with more than one particular fluorophore/quencher combination. Cleavage of the substrates was monitored at various emission and excitation wavelengths (Table 12).

TABLE 12

Substrates and their fluorescent labelling

| Substrate | Name | Fluorophore | Quencher^ | Exci-tation* | Emis-sion* |
|---|---|---|---|---|---|
| Sub49 | Sub49-FB | 6-FAM | BHQ1 | 450-490 | 510-530 |
| Sub3 | Sub3-FIB | | IB | | |
| Sub61 | Sub61-FIB | | | | |
| Sub75 | Sub75-FIB | | | | |
| Sub55 | Sub55-HIB | HEX | IB | 515-535 | 560-580 |
| Sub80 | Sub80-HIB | | | | |
| Sub88 | Sub88-HIB | | | | |
| Sub6 | Sub6-TRB2 | Texas Red | BHQ2 | 560-590 | 610-650 |
| Sub72 | Sub72-TRIBR | | IBR | | |
| Sub74 | Sub74-TRIBR | | | | |
| Sub79 | Sub79-TRIBR | | | | |
| Sub2 | Sub2-Q670B2 | Quasar 670 | BHQ2 | 620-650 | 675-690 |
| Sub72 | Sub72-Q670B2 | | | | |
| Sub80 | Sub80-Q670B2 | | | | |
| Sub60 | Sub60-Q705B2 | Quasar 705 | BHQ2 | 672-684 | 705-730 |
| Sub61 | Sub61-Q705B2 | | | | |
| Sub79 | Sub79-Q705B2 | | | | |

^BHQ1; black hole quencher 1, BHQ2; black hole quencher 2, IB; Iowa black ® FQ, IBR; Iowa black ® RQ
*CFX96 Real-Time PCR Detection System (Biorad) excites, and measures emission of, each fluorophore over a range of wavelengths for each channel.

The reporter substrates tested in this example are shown below with the sequence, 5' to 3'. The lower case bases represent RNA and the upper case bases represent DNA.

SEQ ID NO: 21
Sub2:
AAGGTTTCCTCguCCCTGGGCA

SEQ ID NO: 22
Sub3:
CAGCACAACCguCACCAACCG

SEQ ID NO: 23
Sub6:
ATCACGCCTCguTCCTCCCAG

SEQ ID NO: 28
Sub49:
TAAACTTGGCTCguTGGCTGTGATA

SEQ ID NO: 29
Sub55:
ACCGCACCTCguCCCCAGCTC

SEQ ID NO: 30
Sub60:
GCCAACCACguCCAACACGAC

SEQ ID NO: 73
Sub61:
CTCGACCCCguCTCCACGCCA

SEQ ID NO: 75
Sub72:
ATCACGCCTCguCTCCTCCCAG

SEQ ID NO: 77
Sub74:
ATCACTCCCCguCCCCTCCCAG

```
Sub75:                                          SEQ ID NO: 78
TGACCCTCCTCguCTCCCCACTA

Sub79:                                          SEQ ID NO: 80
TCCTCTCCCCguCCCCTTCAACC

Sub80:                                          SEQ ID NO: 81
AACCGCCCTCguCCCGTGAACC

Sub88:                                          SEQ ID NO: 88
CTCCTCCCTCguCCCCAGCTC
```

4.3. Target Sequence and PCR Primers for Amplification of the CYP2C9, TP53, B2M, HMBS, TFRC and RPL13a genes Human genomic DNA extracted from IM9 cell line (Promega) was used as template for in vitro amplification of the target genes. The amplicons were generated by qPCR using the oligonucleotide PCR primers listed below. Primer sequences are listed from 5' to 3'. The sequence in bold in the primer sequences corresponds to a universal tag (U1, U2 or U3) that increases the Tm of the primer without affecting the specificity of the primer to the gene target. This tag improves amplification efficiency in PCR reactions.

```
                                                SEQ ID NO: 91
Forward primer 5TFRC_U1
GCTAAAACAATAACTCAGAACTTACG SEQ ID NO: 92
Reverse primer 3TFRC_U2
CAGCTTTCTGAGGTTACCATCCTA SEQ ID NO: 123
Forward primer 5B2M_U1
GCTAATCTTTTCCCGATATTCCTCAG SEQ ID NO: 124
Reverse primer 3B2M_U2
CAGCCCAGACACATAGCAATTCAG SEQ ID NO: 125
Forward primer 5TP53_U3
CTAACTTACTGCCTCTTGCTTCTC SEQ ID NO: 126
Reverse primer 3TP53_U2
CAGCTCTGTGCGCCGGTCTCTC SEQ ID NO: 127
Forward primer 5RPL13a_U3
CTAAACCGGAAGAAGAAACAGCTCA SEQ ID NO: 128
Reverse primer 3RPL13a_U2
CAGGAGGAATTAACAGTCTTTATTGG SEQ ID NO: 129
Forward primer 5CYP2C9_U3
CTAACCTCATGACGCTGCGGAA SEQ ID NO: 130
Reverse primer 3CYP2C9_U2
CAGATATGGAGTAGGGTCACCCA SEQ ID NO: 131
Forward primer 5HMBS_U3
CTAAACCCACACACAGCCTACTTTC SEQ ID NO: 132
Reverse primer 3HMBS_U2
CAGAGCCCAAAGTGTGCTGGTCA
```

4.4. Reaction Components: Amplification and Quantification of Target Sequence

Real-time PCR amplification and detection of the target sequence was performed in a total reaction volume of 25 μL. All reactions were conducted in a CFX96 Real-Time PCR Detection System (Bio-Rad). Reactions were set up with substrates and their associated partzymes as in Table 13. The cycling parameters were either;

1) 95° C. for 2 minutes, 50 cycles of 95° C. for 15 seconds and 52° C. for 60 seconds (data collected at the 52° C. step) or 2) 95° C. for 2 minutes, 50 cycles of 95° C. for 15 seconds and 58° C. for 60 seconds (data collected at the 58° C. step).

Each set of reaction conditions was run in duplicate and contained 40 nM forward primer and 200 nM of reverse primer, 200 nM each of partzyme A and partzyme B, 200 nM substrate, 8 mM MgCl$_2$, 200 μM of each dNTP, 10 units RiboSafe RNase inhibitor (Bioline), 1× Immobuffer (Bioline), 2 units of MyTaqHS™ DNA polymerase (Bioline) and either genomic DNA template (100 ng) or no target (NF-H$_2$O).

TABLE 13

Oligonucleotide combinations used for each universal substrate

| Substrate | Partzyme A | Partzyme B | Primers |
|---|---|---|---|
| Sub3 | CYP2C9A/3-P | CYP2C9B/3-P | 5CYP2C9_U1 and |
| SEQ ID NO: 22 | SEQ ID NO: 96 | SEQ ID NO: 97 | 3CYP2C9_U2 |
| Sub61 | CYP2C9A/61-P | CYP2C9B/61-P | SEQ ID NO: 129 and SEQ |
| SEQ ID NO: 73 | SEQ ID NO: 98 | SEQ ID NO: 99 | ID NO: 130 respectively |
| Sub6 | TP53A/6-P | TP53B/6-P | 5TP53_U1 and |
| SEQ ID NO: 23 | SEQ ID NO: 100 | SEQ ID NO: 101 | 3TP53_U2 |
| Sub72 | TP53A/6-P | TP53B/72-P | SEQ ID NO: 125 and SEQ |
| SEQ ID NO: 75 | SEQ ID NO: 100 | SEQ ID NO: 103 | ID NO: 126 respectively |
| Sub74 | TP53A/74-P | TP53B/74-P | |
| SEQ ID NO: 77 | SEQ ID NO: 104 | SEQ ID NO: 105 | |
| Sub79 | TP53A/79-P | TP53B/79-P | |
| SEQ ID NO: 80 | SEQ ID NO: 106 | SEQ ID NO: 107 | |
| Sub60 | B2MA/60-P | B2MB/60-P | 5B2M_U1 and 3B2M_U2 |
| SEQ ID NO: 30 | SEQ ID NO: 108 | SEQ ID NO: 109 | SEQ ID NO: 123 and SEQ |
| Sub61 | B2MA/61-P | B2MB/61-P | ID NO: 124 respectively |
| SEQ ID NO: 73 | SEQ ID NO: 110 | SEQ ID NO: 111 | |
| Sub79 | B2MA/79-P | B2MB/79-P | |
| SEQ ID NO: 80 | SEQ ID NO: 112 | SEQ ID NO: 113 | |
| Sub49 | HMBSA/49-P | HMBSB/49-P | 5HMBS_U1 and |
| SEQ ID NO: 28 | SEQ ID NO: 114 | SEQ ID NO: 115 | 3HMBS_U2 |

TABLE 13-continued

Oligonucleotide combinations used for each universal substrate

| Substrate | Partzyme A | Partzyme B | Primers |
|---|---|---|---|
| Sub75 | HMBSA/75-P | HMBSB/75-P | SEQ ID NO: 131 and SEQ |
| SEQ ID NO: 72 | SEQ ID NO: 116 | SEQ ID NO: 117 | ID NO: 132 respectively |
| Sub2 | TFRCA/2-P | TFRCB/2-P | 5TFRC_U1 and |
| SEQ ID NO: 21 | SEQ ID NO: 34 | SEQ ID NO: 35 | 3TFRC_U2 |
| Sub72 | TFRCA/72-P | TFRCB/72-P | SEQ ID NO: 91 and SEQ |
| SEQ ID NO: 75 | SEQ ID NO: 38 | SEQ ID NO: 55 | NO: 92 respectively |
| SEQ ID NO: 81 | SEQ ID NO: 66 | SEQ ID NO: 67 | |
| Sub55 | RPL13aA/55-P | RPL13aB/55-P | 5RPL13a_U1 and |
| SEQ ID NO: 29 | SEQ ID NO: 118 | SEQ ID NO: 119 | 3RPL13a_U2 |
| Sub80 | RPL13aA/80-P | RPL13aB/80-P | SEQ ID NO: 127 and SEQ |
| SEQ ID NO: 81 | SEQ ID NO: 120 | SEQ ID NO: 121 | ID NO: 128 respectively |
| Sub88 | RPL13aA/88-P | RPL13aB/55-P | |
| SEQ ID NO: 88 | SEQ ID NO: 122 | SEQ ID NO: 119 | |

4.5. Results: Amplification of Target and Cleavage of Reporter Substrate

Figure 7:
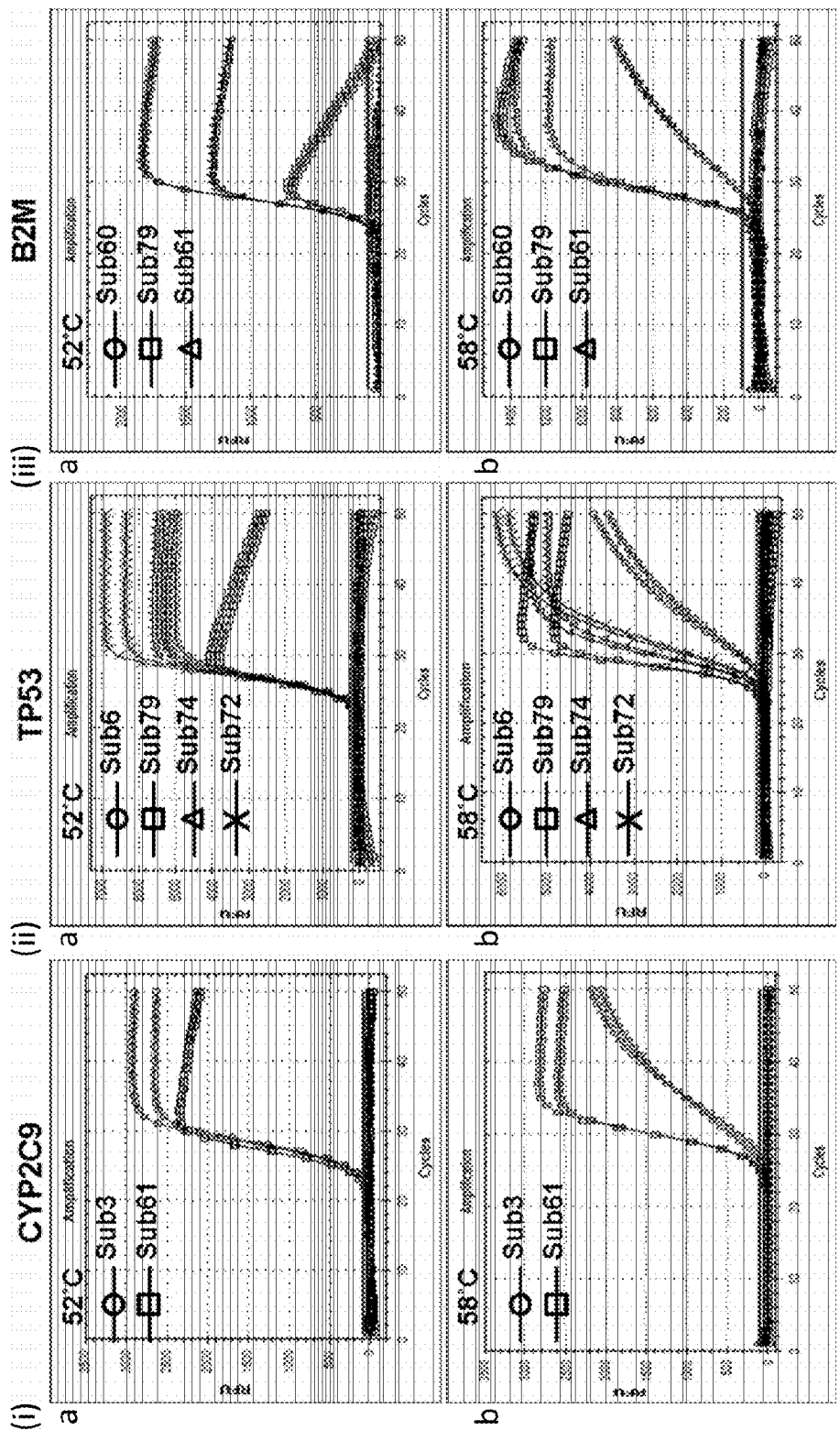
FIG. 7 provides graphs illustrating linear amplification plots generated by MNAzyme qPCR using a range of different universal substrates for detection of a range of human genes. Each combination of substrates and targets was run at an annealing temperature of a) 52° C. or b) 58° C. The universal substrates tested with each gene are indicated by symbols located at the top left of each plot and were (i) Sub3 and Sub61 with CYP2C9, (ii) Sub6, Sub72, Sub74 and Sub79, with TP53, (iii) Sub60, Sub61 and Sub79 with B2M, (iv) Sub49 and Sub75 with HMBS, (v) Sub2, Sub72 and Sub80 with TFRC and (iv) Sub55, Sub80 and Sub88 with RPL13a. The same primer set and genomic DNA were used for all reactions with each different gene, and all partzymes had the same catalytic domains and target-sensor regions matched to the particular gene. The only differences between reactions were the substrate-sensor arms of the partzymes and the fluorescently labelled universal substrates. Thus the difference in the shape of the amplification plot and the Ct values between reactions for the same gene is correlated with efficiency of cleavage of the universal substrates. The steeper the curves and the earlier Ct values indicate a faster number of cycles to achieve a threshold fluorescence, and therefore indicate more efficiently cleaved universal substrates.
Figure 7:
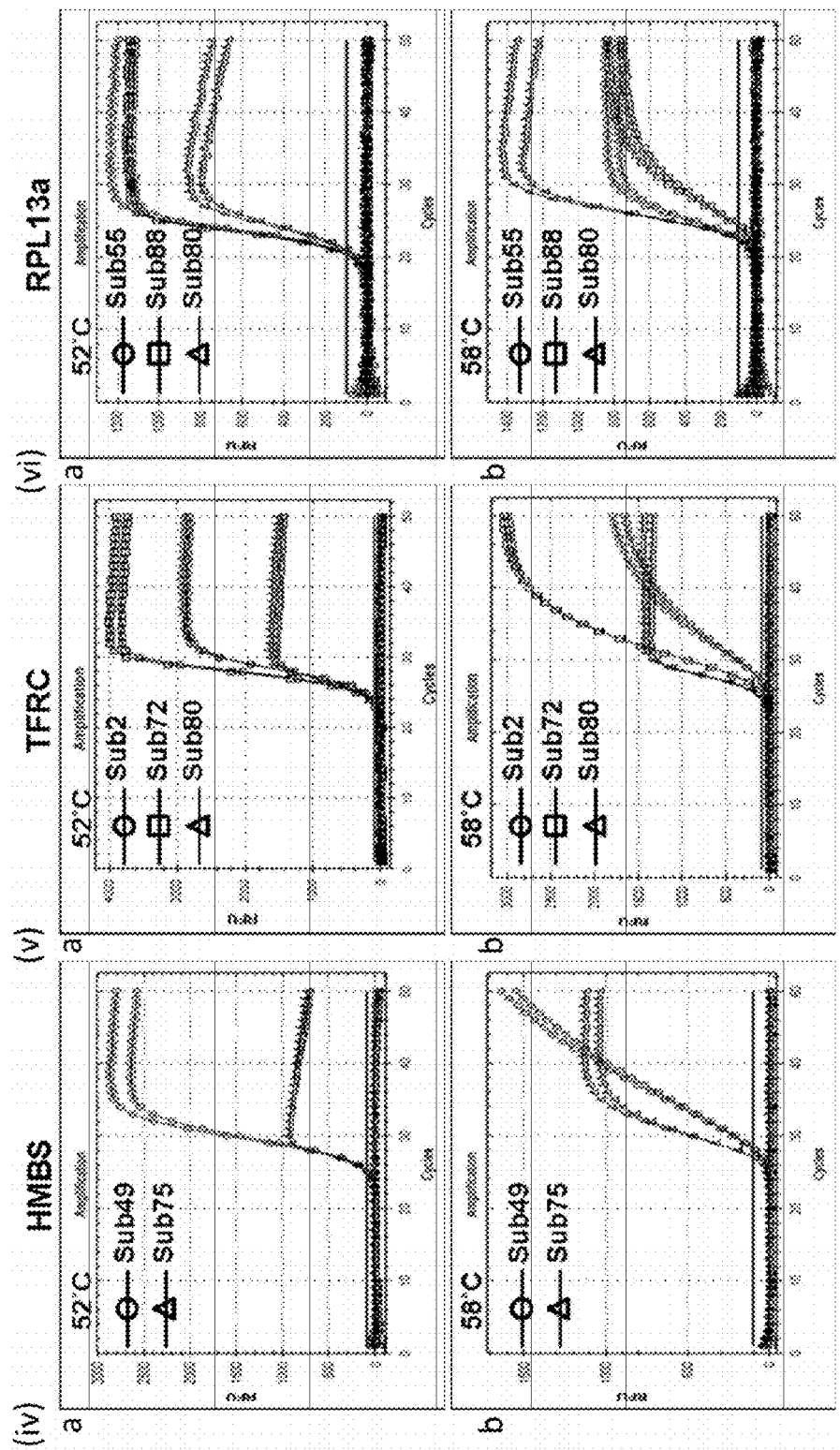

Each MNAzyme qPCR reaction containing human genomic DNA showed an increase in fluorescence over time for the real-time detection of the genes CYP2C9, TP53, B2M, HMBS, RPL13a and TFRC, at annealing temperatures of both 52° C. and 58° C. (FIG. 7). For all universal substrates, the fluorescence of the no-DNA target control was lower than that in the DNA target-containing reactions. This demonstrates that the increase in fluorescence produced in target-containing reactions is due to target dependent assembly of catalytically active MNAzymes that then cleaved one of the universal reporter substrates.

Results from MNAzyme qPCR detection of the CYP2C9 and TP53 genes showed that all universal substrates tested performed equivalently at 52° C. with less than 0.5 Ct difference between the substrates and similar slopes of the amplification curves (Table 14 and FIG. 7, (i)a and (ii)a respectively). The series 1 substrates tested (Sub3 and Sub6) performed worse at the higher temperature of 58° C. than the series 3 substrates tested (Sub61, Sub72, Sub74 and Sub79) with a difference of more than 1 Ct between the substrates and a much shallower slope for the amplification curves for Sub3 and Sub6 indicating a less efficient reaction (Table 14 and FIG. 7, (i)b and (ii)b respectively). These data show that the improved design of these series 3 substrates (Sub61, Sub72, Sub74 and Sub79) leads to more efficient cleavage at 58° C., and that this improved performance at elevated temperatures does not prevent these substrates from being efficiently cleaved at a lower temperature.

Results from MNAzyme qPCR detection of the B2M and HMBS genes showed that all the universal substrates tested performed equivalently at 52° C. with only approximately 0.5 Ct difference between the substrates and similar slopes of the amplification curves (Table 14 and FIG. 7, (iii)a and (iv)a respectively). The series 2 substrates tested (Sub60 and Sub49) performed worse at the higher temperature of 58° C. than the series 3 substrates tested (Sub61 and Sub75, and Sub79) with a difference of more than 1 Ct between the substrates and a shallower slope for the amplification curves for Sub60 and Sub49 indicating a less efficient reaction (Table 14 and FIG. 7, (iii)b and (iv)b respectively). These data show that the improved design of these series 3 substrates (Sub61, Sub75 and Sub79) leads to more efficient cleavage at 58° C., but that this improved performance at elevated temperatures does not prevent the substrates from being efficiently cleaved at a lower temperature. The better performance of the series 3 substrates versus the series 2 substrates at 58° C. is attributable to the fact that the series 3 substrates follow all the design guidelines for highly active substrates and the series 2 substrates do not (see Table 9).

Results from MNAzyme qPCR detection of the TFRC gene showed that all universal substrates tested performed equivalently at 52° C. with only approximately 0.5 Ct difference between the substrates and similar slopes of the amplification curves (Table 14 and FIG. 7, (v)a). The series 3 substrates tested (Sub72 and Sub80) both performed better at 58° C. than the series 1 substrate tested (Sub2) with a difference of more than 1 Ct between the substrates and a shallower slope for the amplification curve for Sub2 indicating a less efficient reaction (Table 14 and FIG. 7, (v)b). The series 3 substrate, Sub80, performed better at 58° C. than the series 3 substrate, Sub72, with a greater than 1 Ct difference between the substrates. Sub80 follows all of the design guidelines for highly active substrates and Sub72 does not (see Table 9).

Results from MNAzyme qPCR detection of the RPL13a gene showed that at 52° C. the series 2 substrate Sub55 and the series 3 substrate Sub88 were better than the series 3 substrate Sub80 (Table 14 and FIG. 7, (vi)a). At 58° C. the series 3 substrate Sub80 and the series 2 Sub55 performed the same, and both these substrates performed better than the series 3 substrate Sub88 (Table 14 and FIG. 7, (vi)b). The series 2 substrate Sub55 meets all the all of the design guidelines for highly active substrates (see Table 9) and would therefore be expected to perform well. The series 3 Sub88 also meets all of the design guidelines for highly active substrates (Table 9) but has not performed as well as Sub55. Overall, the design guidelines show a high probability of producing substrates that are efficiently cleaved under MNAzyme qPCR conditions.

Overall, with a range of different target sequences, the series 1, 2 and 3 substrates performed comparably in MNAzyme qPCR performed at 52° C. At 58° C., the series 3 substrates out-performed the series 1 and 2 substrates, with the exception of the series 2 substrate Sub55 which, as explained above, falls within the all the design guidelines for highly active substrates. These data show that the design guidelines do, in general, produce substrates that are robust and efficiently cleaved at a range of temperatures in the context of thermocycling protocols used for qPCR.

Of note is that some of the series 3 substrates, indicated by (ˆ) in Table 14, have very high Tm's, and therefore at lower temperatures they may have poorer turnover over of the cleaved substrate and hence even though the activity is comparable to the other substrates, the final fluorescence value is lower.

TABLE 14

Substrate cleaved by MNAzymes targeted to different genes.

| Gene | Substrate | 52° C. Amplification curve* | Ct | Diff in Ct | 58° C. Amplification curve* | Ct | Diff in Ct |
|---|---|---|---|---|---|---|---|
| CYP2C9 | Sub3 | Sub3 = | 22.9 | <0.5 | Sub61 > | 26.7 | >1.0 |
|  | Sub61 | Sub61 | 22.5 |  | Sub3 | 25.2 |  |
| TP53 | Sub6 | All equal | 23.0 | <0.5 | Sub79 > | 27.4 | (Sub79 & |
|  | Sub72 | (^Sub79) | 22.7 |  | Sub74 > | 24.2 | Sub6) >1.5 |
|  | Sub74 |  | 22.7 |  | Sub72 >> | 25.1 |  |
|  | Sub79 |  | 22.6 |  | Sub6 | 25.8 |  |
| B2M | Sub60 | Sub60 = | 24.0 | (Sub60 & | Sub61 = | 28.5 | >2.0 |
|  | Sub61 | Sub61 > | 23.9 | Sub61) | Sub79 >> | 25.5 |  |
|  | Sub79 | Sub79 | 24.6 | 0.1 | Sub60 | 25.7 |  |
|  |  | (^Sub79) |  |  |  |  |  |
| HMBS | Sub49 | Sub49 = | 25.1 | 0.1 | Sub75 > | 28.1 | >1.0 |
|  | Sub75 | Sub75 | 25.0 |  | Sub49 | 27.0 |  |
|  |  | (^Sub75) |  |  |  |  |  |
| TFRC | Sub2 | Sub72 > | 23.8 | 0.6 | Sub80 > | 27.1 | (Sub80 & |
|  | Sub72 | Sub2 = | 23.2 |  | Sub72 >> | 25.7 | Sub2) >2.0 |
|  | Sub80 | Sub80 | 23.4 |  | Sub2 | 24.8 |  |
|  |  | (^Sub80) |  |  |  |  |  |
| RPL13a | Sub55 | Sub55 = | 20.3 | (Sub55 & | Sub80 > | 22.6 | (Sub55 & |
|  | Sub80 | Sub88 > | 21.0 | Sub88) <0.5 | Sub55 > | 22.3 | Sub88) >2.0 |
|  | Sub88 | Sub80 | 20.3 |  | Sub88 | 24.3 |  |
|  |  | (^Sub80) |  |  |  |  |  |

*The shape of the amplification curve (steepness and time taken to reach plateau) demonstrates the reaction efficiency.
^Tm of these substrates is too high for lower reaction temperatures and this can result in poor turnover over of the cleaved portions of the substrate and thus lower final fluorescence values.

Example 5

Use of Universal Substrates with DNAzymes

The 10-23 DNAzyme is a unimolecular structure that can directly bind to, and modify, a substrate sequence. The 10-23 DNAzyme has utility in in vitro diagnostic applications. Due to similarity in the catalytic region, the 10-23 DNAzyme can bind and cleave substrates that are cleavable by the MNAzyme based on the 10-23 DNAzyme. Unlike the MNAzyme, the DNAzyme does not need a target sequence to form the active core, and therefore the binding and subsequent cleavage of the substrate by the 10-23 DNAzyme is not influenced by the target sequence and does not utilize a split catalytic core. The ability of matched 10-23 DNAzymes to cleave the series 1 universal substrates (Sub2, Sub3, and Sub6), the series 2 universal substrates (Sub44, Sub45, Sub49, Sub55 and Sub60T) and the series 3 substrates (Sub61, Sub72, Sub73, Sub74, Sub75, Sub77, Sub79, Sub80, Sub84, Sub85, Sub86, Sub87, Sub88, and Sub89) was measured to determine if the design guidelines of the present invention lead to the development of substrates that can be cleaved by the 10-23 DNAzyme with high activity and robustly over a range of temperatures.

5.1. 10-23 DNAzyme Oligonucleotides

A series of 10-23 DNAzymes were designed with sensor arms complementary to the substrates described above and listed in Tables 4 and 5. The sequences of the DNAzymes are listed below from 5' to 3', where the bases underlined hybridize to the substrate and the bases in italics form the catalytic core. Some DNAzyme sequences below contain an extra G at the very 5' and 3' ends (e.g. Dz55). These added bases do not hybridize with the substrates and do not impact on the efficiency at which the DNAzyme cleaved the substrate.

SEQ ID NO: 133
DNAzyme Dz2
TGCCCAGGGA*GGCTAGCTACAACGA*GAGGAAACCTT

SEQ ID NO: 134
DNAzyme Dz3
CGGTTGGTGA*GGCTAGCTACAACGA*GGTTGTGCTG

SEQ ID NO: 135
DNAzyme Dz6
CTGGGAGGAA*GGCTAGCTACAACGA*GAGGCGTGAT

SEQ ID NO: 136
DNAzyme Dz44
TCACTATAGGGA*GGCTAGCTACAACGA*GAGGAGACCTG

SEQ ID NO: 137
DNAzyme Dz45
TTCCAAAGGAGA*GGCTAGCTACAACGA*GGGGACCCGT

SEQ ID NO: 138
DNAzyme Dz49
TATCACAGCCAA*GGCTAGCTACAACGA*GAGCCAAGTTTA

SEQ ID NO: 139
DNAzyme Dz55
GGAGCTGGGGA*GGCTAGCTACAACGA*GAGGTGCGGTG

SEQ ID NO: 140
DNAzyme Dz60
GTCGTGTTGGA*GGCTAGCTACAACGA*GTGGTTGGC

SEQ ID NO: 141
DNAzyme Dz61
GTGGCGTGGAGA*GGCTAGCTACAACGA*GGGGTCGAGG

SEQ ID NO: 142
DNAzyme Dz72
GCTGGGAQGAGA*GGCTAGCTACAACGA*GAGGCGTGATG

SEQ ID NO: 143
DNAzyme Dz73
GCACGAGGGGA*GGCTAGCTACAACGA*GGGGACGCCAG

```
                                SEQ ID NO: 144
DNAzyme Dz74
GCTGGGAGGGAGGCTAGCTACAACGAGGGGAGTGATG SEQ ID NO: 145
DNAzyme Dz75
GTAGTGGGGAGAGGCTAGCTACAACGAGAGGAGGGTCAG SEQ ID NO: 146
DNAzyme Dz77
GAGGAGGAGGGAGGCTAGCTACAACGAGAGGGAGGAGG SEQ ID NO: 147
DNAzyme Dz79
GGGTTGAAGGGGAGGCTAGCTACAACGAGGGGAGAGGAG SEQ ID NO: 148
DNAzyme Dz80
GGGTTCACGGGAGGCTAGCTACAACGAGAGGGCGGTTGG SEQ ID NO: 149
DNAzyme Dz84
GCTGGGAGGAGAGGCTAGCTACAACGAGAGGTGCGGTG SEQ ID NO: 150
DNAzyme Dz85
GCTGGGAGGGGAGGCTAGCTACAACGAGAGGTGCGGTG SEQ ID NO: 151
DNAzyme Dz86
GGAGCTGGGGAGGCTAGCTACAACGAGAGGCGTGATG SEQ ID NO: 152
DNAzyme Dz87
GGAGCTGGGGAGGCTAGCTACAACGAGGGGAGTGATG SEQ ID NO: 153
DNAzyme Dz88
GGAGCTGGGGAGGCTAGCTACAACGAGAGGGAGGAGG SEQ ID NO: 154
DNAzyme Dz89
GAGGAGGAGGGAGGCTAGCTACAACGAGAGGTGCGGTG
```

5.2. Reporter Substrates

In the current example, the substrates were end labelled with a 6-FAM moiety at the 5' end (indicated by a "F" in the name of the substrates below) and an Iowa Black® FQ quencher moiety at the 3' end (indicated by a "IB" in the name of the substrates below). Cleavage of the substrates was monitored between 510-530 nm (FAM emission wavelength range on CFX96 (BioRad)) with excitation between 450-490 nm (FAM excitation wavelength range on CFX96 (BioRad)). The reporter substrates for this example are shown below with the sequence, 5' to 3'. The lower case bases represent RNA and the upper case bases represent DNA.

```
                                SEQ ID NO: 21
Sub2-FIB:
AAGGTTTCCTCguCCCTGGGCA

SEQ ID NO: 22
Sub3-FIB:
CAGCACAACCguCACCAACCG

SEQ ID NO: 23
Sub6-FIB:
ATCACGCCTCguTCCTCCCAG

SEQ ID NO: 25
Sub44-FIB:
CAGGTCTCCTCguCCCTATAGTGA

SEQ ID NO: 26
Sub45-FIB:
ACGGGTCCCguCTCCTTTGGAA

SEQ ID NO: 28
Sub49-FB:
TAAACTTGGCTCguTGGCTGTGATA

SEQ ID NO: 29
Sub55-FIB:
ACCGCACCTCguCCCCAGCTC

SEQ ID NO: 72
Sub60T-FIB:
TGCCAACCACguCCAACACGAC

SEQ ID NO: 73
Sub61-FIB:
CTCGACCCCguCTCCACGCCA

SEQ ID NO: 75
Sub72-FIB:
ATCACGCCTCguCTCCTCCCAG

SEQ ID NO: 76
Sub73-FB:
TGGCGTCCCCguCCCCTCGTG

SEQ ID NO: 77
Sub74-FIB:
ATCACTCCCCguCCCCTCCCAG

SEQ ID NO: 78
Sub75-FIB:
TGACCCTCCTCguCTCCCCACTA

SEQ ID NO: 79
Sub77-FB:
CTCCTCCCTCguCCCTCCTCCT

SEQ ID NO: 80
Sub79-FIB:
TCCTCTCCCCguCCCCTTCAACC

SEQ ID NO: 81
Sub80-FIB:
AACCGCCCTCguCCCGTGAACC

SEQ ID NO: 84
Sub84-FIB:
ACCGCACCTCguCTCCTCCCAG

SEQ ID NO: 85
Sub85-FIB:
ACCGCACCTCguCCCCTCCCAG

SEQ ID NO: 86
Sub86-FIB:
ATCACGCCTCguCCCCAGCTC

SEQ ID NO: 87
Sub87-FIB:
ATCACTCCCCguCCCCAGCTC

SEQ ID NO: 88
Sub88-FIB:
CTCCTCCCTCguCCCCAGCTC

SEQ ID NO: 89
Sub89-FIB:
ACCGCACCTCguCCCTCCTCCT
```

5.3. Reaction Components: Cleavage of a Substrate by a DNAzyme at Temperatures Between 50° C. and 60° C.

Cleavage of a substrate was measured by an increase in fluorescent signal caused by the binding and subsequent cleavage by a matched DNAzyme. Separate reactions were set up to measure the cleavage of each substrate with its matched DNAzyme (oligonucleotides as in Table 15). Reactions contained 1×PCR Buffer II (Applied Biosystems), 10 mM MgCl$_2$, 200 nM Substrate and NF-H$_2$O in total volume of 25 µL. Each reaction was run in duplicate as either a "test" (addition of 1 nM DNAzyme) or "control" (addition of NF-H$_2$O) reaction. Reactions were performed on a CFX96™ Real-Time PCR Detection System (BioRad) at 50, 52, 54, 56, 58 and 60° C. Fluorescence for each reaction was programmed to be read after 1 second for the first 50 cycles and then programmed to be read after 25 seconds for the next 50 cycles.

TABLE 15

DNAzymes tested with matching Substrates

| Substrate | DNAzyme |
|---|---|
| Sub2 SEQ ID NO: 21 | Dz2 SEQ ID NO: 133 |
| Sub3 SEQ ID NO: 22 | Dz3 SEQ ID NO: 134 |
| Sub6 SEQ ID NO: 23 | Dz6 SEQ ID NO: 135 |
| Sub44 SEQ ID NO: 25 | Dz44 SEQ ID NO: 136 |
| Sub45 SEQ ID NO: 26 | Dz45 SEQ ID NO: 137 |
| Sub49 SEQ ID NO: 28 | Dz49 SEQ ID NO: 138 |
| Sub55 SEQ ID NO: 29 | Dz55 SEQ ID NO: 139 |
| Sub60T SEQ ID NO: 72 | Dz60 SEQ ID NO: 140 |
| Sub61 SEQ ID NO: 73 | Dz61 SEQ ID NO: 141 |
| Sub72 SEQ ID NO: 75 | Dz72 SEQ ID NO: 142 |
| Sub73 SEQ ID NO: 76 | Dz73 SEQ ID NO: 143 |
| Sub74 SEQ ID NO: 77 | Dz74 SEQ ID NO: 144 |
| Sub75 SEQ ID NO: 78 | Dz75 SEQ ID NO: 145 |
| Sub77 SEQ ID NO: 79 | Dz77 SEQ ID NO: 146 |
| Sub79 SEQ ID NO: 80 | Dz79 SEQ ID NO: 147 |
| Sub80 SEQ ID NO: 81 | Dz80 SEQ ID NO: 148 |
| Sub84 SEQ ID NO: 84 | Dz84 SEQ ID NO: 149 |
| Sub85 SEQ ID NO: 85 | Dz85 SEQ ID NO: 150 |
| Sub86 SEQ ID NO: 86 | Dz86 SEQ ID NO: 151 |
| Sub87 SEQ ID NO: 87 | Dz87 SEQ ID NO: 152 |
| Sub88 SEQ ID NO: 88 | Dz88 SEQ ID NO: 153 |
| Sub89 SEQ ID NO: 89 | Dz89 SEQ ID NO: 154 |

5.5. Results: Cleavage of a Substrate by a DNAzyme at Various Temperatures

Each test reaction containing DNAzymes with matched substrates showed an increase in fluorescence over time. There was no increase in fluorescence of water only control reactions (no DNAzyme added). This demonstrates that the increase in fluorescence produced in the DNAzyme-containing reactions was due to the binding and subsequent catalytic cleavage of the reporter substrate by the DNAzyme.

For each substrate data set (test and control reactions), the raw fluorescence data points were exported into Excel (Microsoft), duplicate values were averaged and then normalised. Normalisation was performed by dividing each averaged data point by the averaged value of the no-DNAzyme reaction at the first reading of reactions containing the same substrate (e.g. the averaged data for the test reactions for Sub61 was divided by the averaged fluorescence at cycle 1 for the Sub61 no-DNAzyme control reaction; the averaged data for the no-DNAzyme control reactions for Sub61 was divided by the averaged fluorescence at cycle 1 for the Sub61 no-DNAzyme control reaction.) These normalised data were then used to calculate the signal to noise ratio at approximately 10 minutes after the start of the reaction, by dividing the normalized fluorescence of the test reaction at 10 minutes by the normalized fluorescence of the no-DNAzyme reaction at 10 minutes. This calculation of signal to noise was performed for each combination of DNAzyme and substrate and at each temperature tested. The signal to noise value was then plotted on a bar graph to compare the efficiency of cleavage of each substrate by its matched DNAzyme at the various temperatures (FIG. 8, (i)). The standard deviation of the signal to noise ratio for each substrate over the temperature range was also calculated and plotted to determine substrates with consistent signal to noise over the tested range of temperatures (FIG. 8, (ii)). This suggests that these substrates are robust with respect to temperature.

Due to experimental error there are no data for Sub2 at 54° C. or for Sub79 at 58° C., however this has minimal impact on the overall interpretation of the data.

Figure 8:
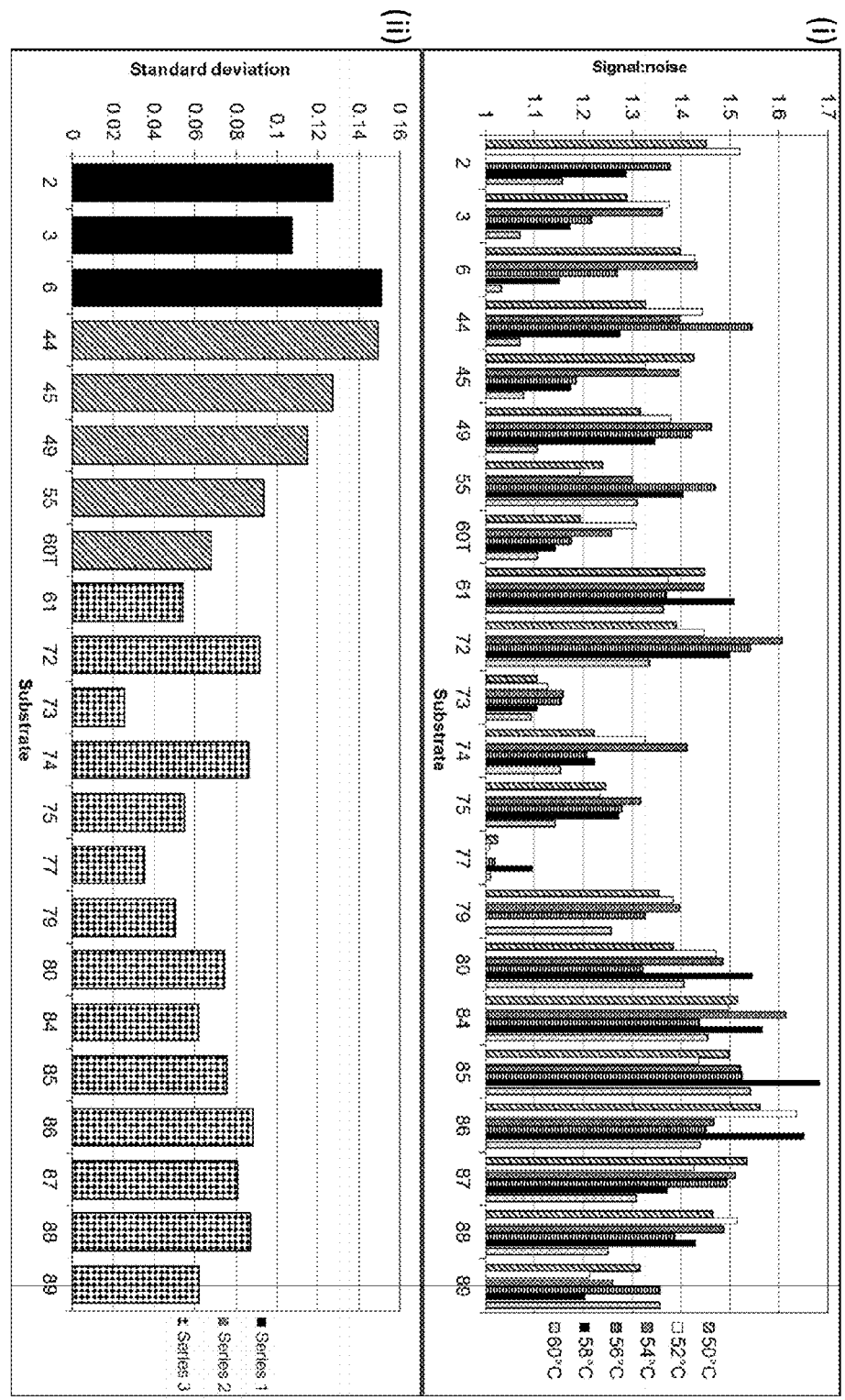
FIG. 8 provides graphs illustrating the signal to noise ratio resulting from DNAzyme mediated cleavage of a range of universal substrates in an isothermal format. The signal to noise ratio was calculated from normalized fluorescence data collected during cleavage reactions at a range of reaction temperatures. The identity of the universal substrates used in reactions is indicated on the x-axis (where "2" refers to Sub2, "3" refers to Sub3 etc.).

Analysis of the signal to noise ratio for each substrate (FIG. 8, (i)) shows that the series 1 substrates (Sub2, Sub3 and Sub6) had high signal to noise at the lower temperatures measured. However the cleavage efficiency of these substrates dropped dramatically as the reaction temperature was increased. A similar pattern was seen for a subset of the series 2 substrates (Sub44, Sub45, Sub49 and Sub60T). The other series 2 substrate (Sub55), and the majority of the series 3 substrates tested (Sub61, Sub72, Sub74, Sub75, Sub79, Sub80, Sub84, Sub85, Sub86, Sub87, Sub88 and Sub89) displayed high signal to noise across all the temperatures tested. The series 3 substrates Sub73 and Sub77 had uniformly low signal to noise at all temperatures tested indicating that although the new design guidelines provide a good probability of design of robust substrates (83% success rate for this application), there will still be some sequences that meet these guidelines but that are unsuitable for a subset of MNAzyme and/or DNAzyme diagnostic applications. The results for Sub73 and Sub77 also prove that methods utilizing DNAzymes for mass screening of potential substrate sequences to find those that are suitable for MNAzyme diagnostic applications may be missing out on detection of substrates that would be robust and efficiently cleaved by MNAzymes in qPCR applications and vice versa (see Example 2 for the successful utilization of Sub73 and Sub77 in MNAzyme qPCR, FIG. 5).

Overall, the majority of the substrates that conform to all of the design guidelines (Table 9) showed a greater signal to noise ratio across the tested temperature range than the substrates that fell outside one or more of these guidelines (FIG. 8, (i)). More specifically reactions with Sub55, Sub61, Sub72, Sub74, Sub75, Sub79, Sub80, Sub84, Sub85, Sub86, Sub87, Sub88 and Sub89 displayed high signal to noise values at every temperature tested, demonstrating that these are robust substrates over a range of temperatures. This improvement was further evident when the standard deviation was calculated from the signal to noise ratio across the temperatures for each substrate (FIG. 8, (ii)). This measure of variability indicated that, over the temperature range tested, the series 2 substrate, Sub55, and the series 3 substrates Sub61, Sub72 Sub74, Sub75, Sub79, Sub80, Sub82, Sub83, Sub85, Sub86, Sub87, Sub88 and Sub89, had similar signal to noise across the temperatures tested demonstrating that they are robust substrates across a broad temperature range. Note that although Sub60T, Sub73 and Sub77 do demonstrate a low standard deviation in signal to noise over the temperature range, the absolute signal to noise is very low at all temperatures excluding these substrates from being a robust substrate in this application.

Example 6

Testing for Non-Specific Cleavage of Universal Substrates with MNAzyme qPCR

MNAzymes can be used to monitor amplification of target nucleic acids in real-time using in vitro target amplification methods such as PCR. Amplification and detection are performed in a one-step process, wherein PCR amplification and MNAzyme-mediated detection occur simultaneously in a single tube. Multiple targets can be amplified and detected in a single reaction vessel using partzymes with target sensor arms specific to the individual targets. Partzymes for the detection of a first target will bind to and cleave a first substrate, partzymes for the detection of a second target will bind to and cleave a second substrate and so on. For the detection of targets to be specific, there can be no non-specific cleavage of a substrate by partzymes designed to cleave any other substrate in the reaction mix.

The degree of complementarity of the substrate sensor arms of MNAzyme partzymes with other substrates present in the reaction impacts on the specificity of binding. Full complementarity of bases closest to the ribonucleotides are more crucial to specific cleavage. The design guidelines for creation of efficiently cleaved universal substrates include constraints around the sequence composition of universal substrates i.e. seven or more cytosine nucleotides in the ten bases surrounding the ribonucleotides ($N_4$-$N_{13}$); the bases immediately adjacent to the ribonucleotides are cytosines ($N_8$ and $N_9$); total content of substrate has >64% pyrimidines. These constraints may lead to similarities in the sequence of the substrate close to the ribonucleotides, and possibly result in non-specific cleavage of a universal substrate by partially matched partzymes, especially in a multiplex format where a range of universal substrates are present with their associated partzymes in a single reaction mix. If a substrate is cleaved in a non-specific manner by partially matched partzymes designed to specifically cleave a second substrate, then that particular combination of substrates may not be suitable for use in multiplex format.

In this example, the universal substrates Sub44, Sub55, Sub61, Sub65, Sub72 and Sub74 were tested for non-specific cleavage activity by the partzymes associated with Sub44, Sub55, Sub72 and Sub74. This involved testing each universal substrate individually with partzyme pairs designed to bind with full complementarity to the other substrates to see if a signal was detected in a MNAzyme qPCR format. The partzymes of Sub72 and Sub74 were chosen for this test as their respective substrates differ by only 3 bases (FIG. 9, (i)a and (ii)a). The partzymes of Sub55 were chosen to be tested with Sub61 and Sub65 as they are very similar in the central region around the ribonucleotides ($N_4$-$N_{13}$) (FIG. 9, (iii)a). The partzymes of Sub44 were chosen as a control as they are less similar to the other substrates (FIG. 9, (iv)a).

6.1. Partzyme Oligonucleotides

In the experiments conducted to test for non-specific cleavage by non-complementary partzymes, partzyme oligonucleotides A and B were designed with target sensor arms complementary to the human RPL13a gene and substrate sensor arms complementary to each of the universal substrates as discussed above. The sequences of the A and B partzymes are listed below from 5' to 3', where the bases underlined hybridize to the substrate. The "-P" indicates 3' phosphorylation of the oligonucleotide.

```
                                       SEQ ID NO: 155
partzyme A RPL13aA/44-P:
AATTGACAAATACACAGAGGTCACAACGAGAGGAGACCTG SEQ ID NO: 156
partzyme B RPL13aB/44-P:
TCACTATAGGGAGGCTAGCTCTCAAGACCCACGGACTCCT SEQ ID NO: 118
partzyme A RPL13aA/55-P
TTGACAAATACACAGAGGTCACAACGAGAGGTGCGGT
```

```
                                       SEQ ID NO: 119
partzyme B RPL13aB/55-P
GAGCTGGGGAGGCTAGCTCTCAAGACCCACGGACTCCT SEQ ID NO: 157
partzyme A RPL13aA/72-P:
AATTGACAAATACACAGAGGTCACAACGAGAGGCGTGAT SEQ ID NO: 158
partzyme B RPL13aB/72-P:
CTGGGAGGAGAGGCTAGCTCTCAAGACCCACGGACTCCT SEQ ID NO: 159
partzyme A RPL13aA/74-P:
AATTGACAAATACACAGAGGTCACAACGAGGGGAGTGAT SEQ ID NO: 160
partzyme B RPL13aB/74-P:
CTGGGAGGGGAGGCTAGCTCTCAAGACCCACGGACTCCT
```

6.2. Reporter Substrates

In the current example, the substrates were end labelled with a 6-FAM moiety at the 5' end (indicated by a "F" in the name of the substrates below) and an Iowa Black® FQ quencher moiety at the 3' end (indicated by a "IB" in the name of the substrates below). Cleavage of the substrates was monitored at 530 nm (FAM emission wavelength) with excitation at 485 nm (FAM excitation wavelength). The reporter substrates for this example are shown below with the sequence, 5' to 3'. The lower case bases represent RNA and the upper case bases represent DNA.

```
                                       SEQ ID NO: 25
Sub44-FB:
CAGGTCTCCTCguCCCTATAGTGA

SEQ ID NO: 29
Sub55-FB:
ACCGCACCTCguCCCCAGCTC

SEQ ID NO: 73
Sub61-FB:
CTCGACCCCguCTCCACGCCA

SEQ ID NO: 74
Sub65-FB:
TCTCGACCTCguCTCCACGCCA

SEQ ID NO: 75
Sub72-FB:
ATCACGCCTCguCTCCTCCCAG

SEQ ID NO: 77
Sub74-FB:
ATCACTCCCCguCCCCTCCCAG
```

6.3. Target Sequence and PCR Primers for Amplification of RPL13a

The target sequence for this example was a PCR amplicon from the RPL13a gene generated by in vitro PCR amplification of human genomic DNA extracted from the IM9 cell line (Promega) using the oligonucleotide PCR primers listed below. The reporter substrates for this example are shown below with the sequence, 5' to 3'.

```
                                       SEQ ID NO: 161
Forward primer 5RPL13a:
ACCGGAAGAAGAAACAGCTCA SEQ ID NO: 162
Reverse primer 3RPL13a:
GAGGAATTAACAGTCTTTATTGG
```

6.4. Reaction Components: Amplification and Measurement of Specific and Non-Specific Cleavage of Universal Substrates Real-time PCR amplification and detection of the target sequence was performed in a total reaction volume of 25 μL. All reactions were conducted in an Mx3005P QPCR system (Stratagene). The cycling parameters were, 95° C. for 2 minutes, 40 cycles of 95° C. for 15 seconds and 52° C. for 60 seconds (data collected at 52° C.). Reactions were set up with substrates and partzymes as in Table 16. Each set of reaction conditions was tested in duplicate and contained 40 nM 5RPL13a and 200 nM of 3RPL13a, 200 nM of partzyme A, 200 nM partzyme B, 200 nM substrate, 8 mM $MgCl_2$, 200 μM of each dNTP, 10 units RNasin (Promega), 1× Immobuffer (Bioline), 2 units of MyTaqHS™ DNA polymerase (Bioline) and either genomic DNA template (50 ng) or no target ($NF-H_2O$).

TABLE 16

Partzyme combinations used for each universal substrate

| Partzymes | Substrate | Testing for: |
|---|---|---|
| RPL13aA/44-P SEQ ID NO: 155 and RPL13aB/44-P SEQ ID NO: 156 | Sub44 SEQ ID NO: 25 | Specific cleavage |
| | Sub55 SEQ ID NO: 29 | Non-specific cleavage |
| | Sub61 SEQ ID NO: 73 | Non-specific cleavage |
| | Sub65 SEQ ID NO: 74 | Non-specific cleavage |
| | Sub72 SEQ ID NO: 75 | Non-specific cleavage |
| | Sub74 SEQ ID NO: 77 | Non-specific cleavage |
| RPL13aA/55-P SEQ ID NO: 118 and RPL 13aB/55-P SEQ ID NO: 119 | Sub44 SEQ ID NO: 25 | Non-specific cleavage |
| | Sub55 SEQ ID NO: 29 | Specific cleavage |
| | Sub61 SEQ ID NO: 73 | Non-specific cleavage |
| | Sub65 SEQ ID NO: 74 | Non-specific cleavage |
| | Sub72 SEQ ID NO: 75 | Non-specific cleavage |
| | Sub74 SEQ ID NO: 77 | Non-specific cleavage |
| RPL13aA/72-P SEQ ID NO: 157 and RPL13aB/72-P SEQ ID NO: 158 | Sub44 SEQ ID NO: 25 | Non-specific cleavage |
| | Sub55 SEQ ID NO: 29 | Non-specific cleavage |
| | Sub61 SEQ ID NO: 73 | Non-specific cleavage |
| | Sub65 SEQ ID NO: 74 | Non-specific cleavage |
| | Sub72 SEQ ID NO: 75 | Specific cleavage |
| | Sub74 SEQ ID NO: 77 | Non-specific cleavage |
| RPL13aA/74-P SEQ ID NO: 159 and RPL13aB/74-P SEQ ID NO: 160 | Sub44 SEQ ID NO: 25 | Non-specific cleavage |
| | Sub55 SEQ ID NO: 29 | Non-specific cleavage |
| | Sub61 SEQ ID NO: 73 | Non-specific cleavage |
| | Sub65 SEQ ID NO: 74 | Non-specific cleavage |
| | Sub72 SEQ ID NO: 75 | Non-specific cleavage |
| | Sub74 SEQ ID NO: 77 | Specific cleavage |

6.5. Results: Measurement of Specific and Potential Non-Specific Cleavage by a MNAzyme There was an increase in fluorescence in all reactions that contained genomic DNA and a universal substrate with partzymes with substrate sensor arms that were fully complementary to the universal substrate (i.e. reactions testing for specific cleavage). The fluorescence of the no-DNA target controls was lower than the fluorescence in the reactions testing for specific cleavage, demonstrating that the increase in fluorescence in reactions testing for specific cleavage was due to target dependent assembly of catalytically active MNAzymes that then cleaved the fully complementary universal reporter substrates.

Figure 9:
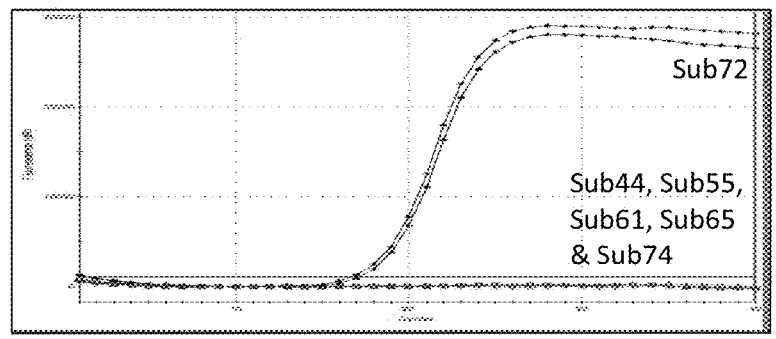
FIG. 9 provides graphs illustrating linear amplification plots from MNAzyme qPCR performed with a range of different universal substrates (Sub44, Sub55, Sub61, Sub65, Sub72 and Sub74) to investigate non-specific cleavage activity with a subset of partzymes (designed with substrate sensor arms to be complementary to Sub44, Sub55, Sub72 and Sub74) for detection of the human RPL13a gene. Each universal substrate was tested individually with partzyme pairs designed to bind with full complementarity to the other substrates to determine if a signal could be detected. The partzymes complementary to (i) Sub72, (ii) Sub74, (iii) Sub55 and (iv) Sub44, were tested with all substrates. In Panel (a) the bottom line of the table indicates the substrate to which the partzymes in the experiment exhibit full complementarity. The other rows of the table show an alignment of the sequences of the other substrates tested in each experiment with differences between the bottom substrate and other substrates sequences indicated by letters that are grey and underlined. In Panel (b) linear amplification plots are illustrated. The normalised fluorescence (y-axis) is plotted against the cycle number (x-axis). Individual amplification curves are labelled on the right of the plot to indicate which amplification curve relates to each substrate. The threshold fluorescence is indicated by a solid horizontal line above the x-axis. An increasing signal above the threshold fluorescence indicates cleavage of the universal substrate.
Figure 9:
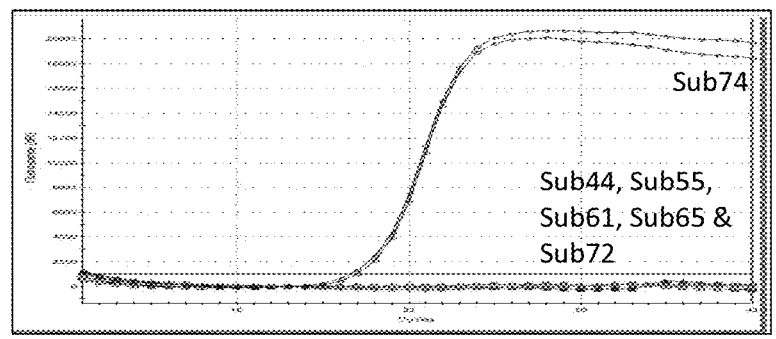

There was no increase in fluorescence in any reaction testing cross-reactivity (FIG. 9, (i)b-(iv)b). This demonstrates that partzymes designed to cleave these closely related universal substrates only cleaved substrates with which they had full complementarity. These data show that these universal substrates are compatible in multiplex MNAzyme qPCR assays.

Example 7

Testing for Non-Specific Cleavage of Universal Substrates with DNAzymes

The 10-23 DNAzyme is a unimolecular structure that can directly bind to and modify a substrate sequence. Unlike the MNAzyme, the 10-23 DNAzyme does not need a target sequence to form the active core therefore the binding and subsequent cleavage of the substrate by the 10-23 DNAzyme is not influenced by the target sequence or having a split catalytic core.

The degree of complementarity of the sensor arms of DNAzymes with the substrate impacts on the specificity of binding. Full complementarity of bases closest to the ribonucleotides are more crucial to specific cleavage. The design guidelines for creation of efficiently cleaved universal substrates include constraints around the sequence composition of universal substrates i.e. seven or more cytosine nucleotides in the ten bases surrounding the ribonucleotides ($N_4$-$N_{13}$); the bases immediately adjacent to the ribonucleotides are cytosines ($N_8$ and $N_9$); total content of substrate has >64% pyrimidines. These constraints may lead to similarities in the sequence of the substrate close to the ribonucleotides, and possibly result in non-specific cleavage of a universal substrate by partially matched DNAzymes, especially in a multiplex format where a range of universal substrates are present with their associated DNAzymes in a single reaction mix. If a substrate is cleaved in a non-specific manner by partially matched DNAzymes designed to specifically cleave a second substrate, then that particular combination of substrates may not be suitable for use in multiplex format.

In this example, the universal substrates Sub55, Sub61, Sub72, Sub74, Sub75, Sub79, Sub80 and Sub85 and their associated 10-23 DNAzymes were tested for non-specific cleavage activity. This involved testing every universal substrate individually with the DNAzymes designed to bind with full complementarity to all the other substrates to see if a signal could be detect in an isothermal detection format. These substrates were chosen to be tested as they have similar sequences in different areas of the substrate.

7.1. 10-23 DNAzyme Oligonucleotides

The 10-23 DNAzymes used in the experiments conducted to test for non-specific cleavage by non-complementary. DNAzymes are listed below from 5' to 3', where the bases underlined hybridize to the substrate and the bases in italics form the catalytic core. Some DNAzyme sequences below contain an extra G at the very 5' and 3' ends. These added bases do not hybridize with the substrate sequence and do not impact on the efficiency at which the DNAzyme cleaved the substrate.

```
                                          SEQ ID NO: 139
DNAzyme Dz55
GGAGCTGGGGAGGCTAGCTACAACGAGAGGTGCGGTG SEQ ID NO: 141
DNAzyme Dz61
GTGGCGTGGAGAGGCTAGCTACAACGAGGGGTCGAGG SEQ ID NO: 142
DNAzyme Dz72
GCTGGGAGGAGAGGCTAGCTACAACGAGAGGCGTGATG SEQ ID NO: 144
DNAzyme Dz74
GCTGGGAGGGGAGGCTAGCTACAACGAGGGGAGTGATG SEQ ID NO: 145
DNAzyme Dz75
GTAGTGGGGAGAGGCTAGCTACAACGAGAGGAGGGTCAG SEQ ID NO: 147
DNAzyme Dz79
GGGTTGAAGGGGAGGCTAGCTACAACGAGGGGAGAGGAG SEQ ID NO: 148
DNAzyme Dz80
GGGTTCACGGGAGGCTAGCTACAACGAGAGGGCGGTTGG SEQ ID NO: 150
DNAzyme Dz85
GCTGGGAGGGGAGGCTAGCTACAACGAGAGGTGCGGTG
```

7.2. Reporter Substrates

In the current example, the substrates were end labelled with a 6-FAM moiety at the 5' end (indicated by a "F" in the name of the substrates below) and an Iowa Black® FQ quencher moiety at the 3' end (indicated by a "IB" in the name of the substrates below). Cleavage of the substrates was monitored between 510-530 nm (FAM emission wavelength range on CFX96 (BioRad)) with excitation between 450-490 nm (FAM excitation wavelength range on CFX96 (BioRad)). The reporter substrates for this example are shown below with the sequence, 5' to 3'. The lower case bases represent RNA and the upper case bases represent DNA.

```
                                          SEQ ID NO: 29
Sub55-FIB:
ACCGCACCTCguCCCCAGCTC

SEQ ID NO: 73
Sub61-FIB:
CTCGACCCCguCTCCACGCCA

SEQ ID NO: 75
Sub72-FIB:
ATCACGCCTCguCTCCTCCCAG

SEQ ID NO: 77
Sub74-FIB:
ATCACTCCCCguCCCCTCCCAG

SEQ ID NO: 78
Sub75-FIB:
TGACCCTCCTCguCTCCCCACTA

SEQ ID NO: 80
Sub79-FIB:
TCCTCTCCCCguCCCCTTCAACC

SEQ ID NO: 81
Sub80-FIB:
AACCGCCCTCguCCCGTGAACC

SEQ ID NO: 85
Sub85-FIB:
ACCGCACCTCguCCCCTCCCAG
```

7.3. Reaction Components: Measurement of Specific and Potential Non-Specific Cleavage of Universal Substrates by a DNAzyme at 52° C. and 58° C.

Cleavage of universal substrates was measured by monitoring fluorescent signal caused by the binding and subsequent modification of a substrate by a DNAzyme. Cleavage of a universal substrate by a DNAzyme will result in the separation of the fluorophore and quencher producing in an increase in fluorescence. All reactions, as outlined in Table 17, contained 1×PCR Buffer II (Applied Biosystems), 10 mM $MgCl_2$, 200 nM Substrate and $NF-H_2O$ in total volume of 25 µL. Each reaction was run in duplicate as either a "test" (addition of 10 nM DNAzyme) or "control" (addition of $NF-H_2O$) reaction. Reactions were performed on a CFX96™ Real-Time PCR Detection System (BioRad) at 52 and 58° C. Fluorescence for each reaction was programmed to be read after 1 second for the first 50 cycles and then programmed to be read after 25 seconds for the next 50 cycles.

TABLE 17

DNAzyme-Substrate combinations tested for specific and non-specific cleavage

| | Dz55 | Dz61 | Dz72 | Dz74 | Dz75 | Dz79 | Dz780 | Dz85 |
|---|---|---|---|---|---|---|---|---|
| Sub55 | test | −ve | −ve | −ve | −ve | −ve | −ve | −ve |
| Sub61 | −ve | test | −ve | −ve | −ve | −ve | −ve | −ve |
| Sub72 | −ve | −ve | test | −ve | −ve | −ve | −ve | −ve |
| Sub74 | −ve | −ve | −ve | test | −ve | −ve | −ve | −ve |
| Sub75 | −ve | −ve | −ve | −ve | test | −ve | −ve | −ve |
| Sub79 | −ve | −ve | −ve | −ve | −ve | test | −ve | −ve |
| Sub80 | −ve | −ve | −ve | −ve | −ve | −ve | test | −ve |
| Sub85 | −ve | −ve | −ve | −ve | −ve | −ve | −ve | test | test; substrate and DNAzyme arms fully complementary (testing for specific cleavage)
−ve; control reactions, substrate and DNAzyme arms not fully complementary (testing for non-specific cleavage)

7.5. Results: Measurement of Specific and Potential Non-Specific Cleavage of Universal Substrates by a DNAzyme There was in increase in fluorescence in each 'test' reaction containing DNAzymes and their fully complementary substrates. There was no increase in fluorescence in any reaction that did not contain DNAzyme (No DNAzyme added). This demonstrates that the increase in fluorescence produced in the DNAzyme-containing 'test' reactions was due to the binding and subsequent catalytic cleavage of the reporter substrate by the DNAzyme.

For each substrate data set (test and control reactions), the raw fluorescence data points were exported into Excel (Microsoft), duplicate values were averaged and then normalised. Normalisation was performed by dividing each averaged data point by the averaged value of the no-DNAzyme reaction after the first reading of reactions containing the same substrate (e.g. the averaged fluorescence for the test reaction for Sub61 was divided by the averaged cycle 1 fluorescence (after the first 8 seconds) for the Sub61 no-DNAzyme reaction; the averaged fluorescence for the no-DNAzyme control reaction for Sub61 was divided by the averaged cycle 1 fluorescence for the no-DNAzyme control reaction.) These normalised data were then used to calculate the signal to noise ratio at 10 minutes, by dividing the test normalized fluorescence at 10 minutes by the no-DNAzyme normalized fluorescence at 10 minutes. This calculation of signal to noise was performed for each temperature. The signal to noise ratio was then plotted on a bar graph to compare the efficiency of cleavage of each universal substrate with each DNAzyme at the various temperatures tested (FIG. 10, (i) and (ii)).

Some reactions with various combinations of substrates and non-complementary DNAzymes showed a slightly raised fluorescence level compared to the paired no-DNAzyme control reaction. This signal did not increase over time and is therefore not indicative of cleavage of the universal substrate by the non-complementary DNAzyme. Detection plots showing this horizontal background fluorescence all had a signal to noise of less than 1.2. Any reaction showing a signal to noise above 1.2 was therefore deemed to either (i) indicate cleavage of a universal substrate (either specific or non-specific), or (ii) indicate that a particular combination of substrate and non-complementary DNAzyme produce a level of background noise that would not be distinguishable from specific cleavage when in a multiplex format.

Figure 10:
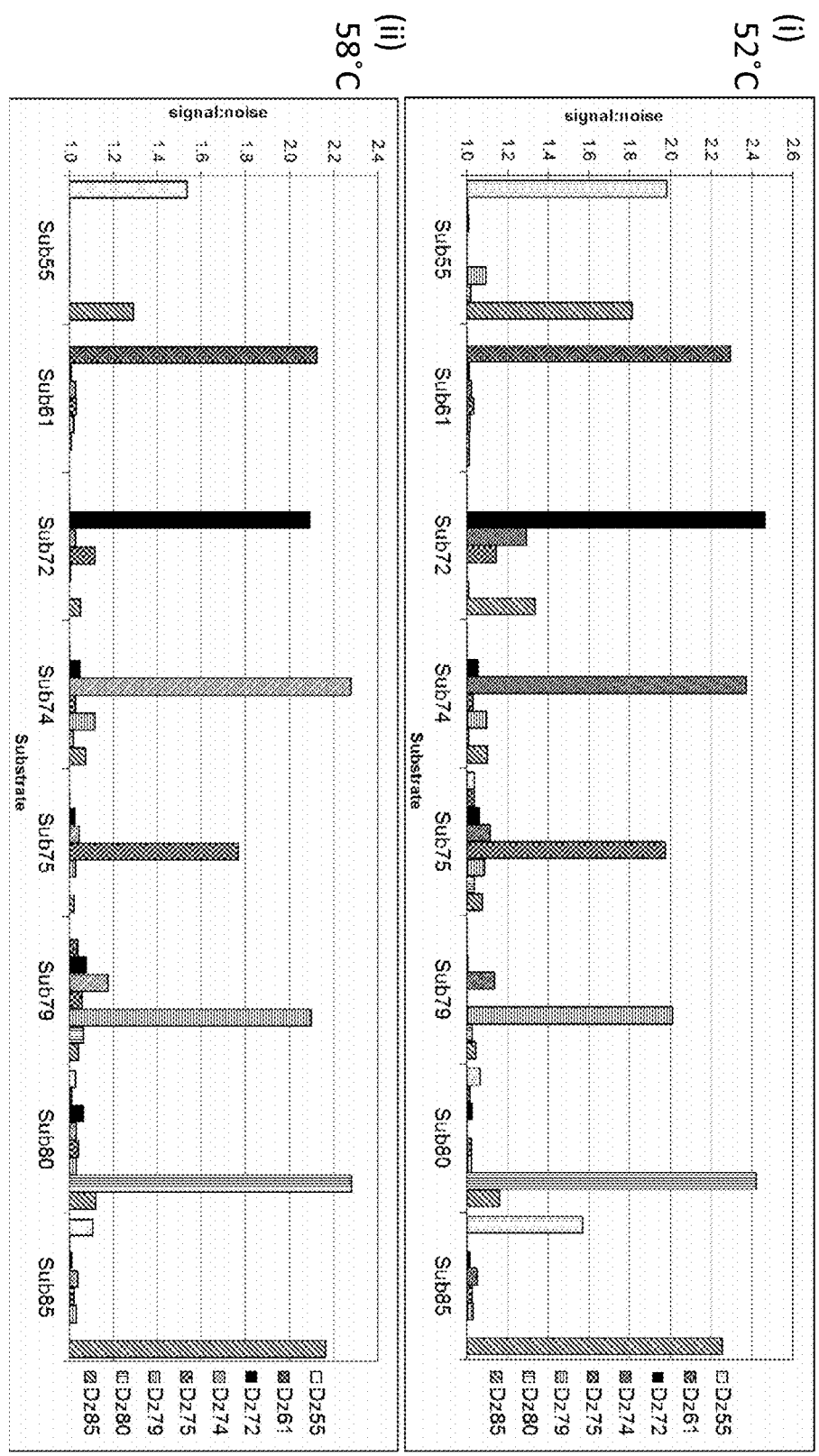
FIG. 10 provides graphs illustrating the signal to noise ratio resulting from DNAzyme mediated cleavage of each universal substrate individually with DNAzymes designed to bind with full complementarity to the other substrates, in an isothermal format. The normalized signal to noise ratio was calculated from normalized fluorescence data collected at reaction temperatures of (i) 52° C. or (ii) 58° C. The identity of the universal substrates used in the reactions is indicated on the x-axis. The different columns of data refer to the cleavage results for each DNAzyme as indicated in the legend, with the signal to noise ratio on the y-axis.

All combinations of universal substrates with their fully matched DNAzymes showed high signal to noise ratios (above the threshold of 1.2) at both temperatures tested (FIG. 10, (i) and (ii)).

There was no non-specific cleavage of the universal substrates Sub61, Sub74, Sub75, Sub79 and Sub80 by any non-complementary DNAzyme at either temperature (FIG. 10, (i) and (ii)).

At 52° C. some universal substrates were cleaved by DNAzymes that were not fully matched to the substrate (where cleavage is defined as a signal to noise ratio above the threshold of 1.2 as described above). The combinations showing non-specific cleavage were: Sub85 non-specifically cleaved by Dz55, Sub72 non-specifically cleaved by Dz74 and Dz85, and Sub55 non-specifically cleaved by Dz85 (FIG. 10, (i)).

The non-specific cleavage of Sub55 by Dz85 could be expected as Sub55 and Dz85 differ by only four bases. Alignment of Sub55 with Dz85 shows the four base mismatch is at the distal end of the 3' substrate arm away from the critical region adjacent to the ribonucleotides (Table 18). Further, one of the 4 bases is a G/T mismatch which is known in the art to bind with some affinity, albeit weaker than for A/T and G/C matches. The non-specific cleavage of Sub85 by Dz55 may also be expected as Sub85 and Dz55 differ by only five bases and this five base mismatch is found at the distal end of the 3' substrate arm away from the critical region adjacent to the ribonucleotides (Table 18). However unlike the reverse scenario above, there are no G/T mismatches present and therefore it appears the Sub85 is not cleaved as efficiently as the reverse combination of Sub55 and Dz85. The non-specific cleavage of Sub72 by Dz74 could be expected as Sub72 and Sub74 differ by only 3 bases. Alignment of Sub72 with Dz74 shows the two mismatches closest to the ribonucleotides are G/T mismatches (Table 18). This also explains why Sub74 is not cleaved by Dz72 as the two mismatches are C/A and occur very close to the ribonucleotides and this is enough to disable cleavage of the substrate by the DNAzyme (Table 18). The non-specific cleavage of Sub72 by Dz85 can be explained by the alignment of the sequences in Table 18, which shows that the mismatch bases are primarily G/T and this would therefore lead Dz85 to bind and cleave Sub72. Again, the reverse situation of Dz72 non-specifically cleaving Sub85 would not be expected as the relevant mismatches become the more destabilising C/A mismatches which are unlikely to lead to strong enough binding between the DNAzyme and the substrate to lead to cleavage.

TABLE 18

Alignment of Substrates and DNAzymes where non-specific cleavage was observed.

| | Name of oligonucleotide | Sequence^ |
|---|---|---|
| Substrate | Sub55 (Seq ID: 29) | ACCGCACCTCguCCCCAGCTC |
| DNAzyme | Dz85 (Seq ID: 150) | GTGGCGTGGAG AGGGGAGGGTCG<br>  GA GG<br> AC    CT<br>  ACATCGA |
| Substrate | Sub85 (Seq ID: 85) | ACCGCACCTCguCCCCTCCCAG |
| DNAzyme | Dz55 (Seq ID: 139) | GTGGCGTGGAG AGGGGTCGAGG<br>  GA GG<br> AC    CT<br>  ACATCGA |
| Substrate | Sub72 (Seq ID: 75) | ATCACGCCTCguCTCCTCCCA |
| DNAzyme | Dz74 (Seq ID: 144) | GTAGTGAGGGG AGGGGAGGGTCG<br>  GA GG<br> AC    CT<br>  ACATCGA |
| Substrate | Sub72 (Seq ID: 75) | ATCACGCCTCguCTCCTCCCAG |
| DNAzyme | Dz85 (Seq ID: 150) | GTGGCGTGGAG AGGGGAGGGTCG<br>  GA GG<br> AC    CT<br>  ACATCGA |

TABLE 18-continued

Alignment of Substrates and DNAzymes where non-specific cleavage was observed.

| | Name of oligonucleotide | Sequence^ |
|---|---|---|
| Substrate | Sub74 (Seq ID: 77) | ATCACTCCCCguCCCTCCCAG |
| DNAzyme | Dz72 (Seq ID: 142) | GTAGTGCGGAG AGAGGAGGGTCG<br>             GA  GG<br>          AC        CT<br>            ACATCGA |

^Substrate sequence written 5' to 3' and DNAzyme sequence written 3' to 5'. Mismatched bases are in bold and underlined and mismatched bases that are G/T are only in bold. The DNAzyme core sequences are in italics.

Increasing the reaction temperature to 58° C. created more stringent conditions for hybridization of oligonucleotides and resulted in the loss of almost all the non-specific cleavage seen at 52° C. (FIG. 10, (ii)). The only combination of universal substrate and DNAzyme that showed non-specific cleavage at 58° C. was Sub55 being cleaved non-specifically by Dz85. This non-specificity is to be expected as Sub55 and Dz85 differ by only four bases and this four base mismatch is found at the distal end of the substrate arm away from the critical region adjacent to the ribonucleotides and one of the mismatches is a G/T (Table 18). Even though there are only three bases different between Sub72 and Sub74, this three base mismatch occurs in the critical region close to the ribonucleotides and are therefore more critical for specificity and will be more destabilising at higher temperatures that create more stringent conditions for binding of oligonucleotides.

These results demonstrate that the design guidelines produce universal substrates that can be effectively multiplexed at a range of temperatures for applications involving 10-23 DNAzymes. There is a need for some optimization of reaction temperature to provide sufficient stringency of binding for some combinations of substrates, but overall the guidelines produce sets of substrates that can be multiplexed. One skilled in the art can appreciate that the length of substrate and DNAzyme binding arms can be adjusted to create more stringent binding at lower and higher temperatures.

Example 8

Use of Universal Substrates with Multiplex MNAzyme qPCR for the Quantification of Five Different Nucleic Acid Targets in a Multiplex Reaction with Annealing Temperatures of 52° C. or 58° C.

Multiple targets can be simultaneously amplified and detected in real time using in vitro target amplification methods such as qPCR. Further, the amplification of the targets can be simultaneously monitored in real-time in one multiplexed reaction that comprises multiple unique MNAzymes. Each MNAzyme can be designed with sensor arms specific for one target and substrate arms specific for a unique member of a series of universal substrates. Each target can be individually detected if each of the series of universal substrates is labelled with a different fluorophore. The amplification and detection of the multiple targets are performed in a one-step process, wherein PCR amplification and MNAzyme-mediated detection occur simultaneously in a single tube. Real-time monitoring generates an amplification curve that can indicate the efficiency of a reaction by the shape of the curve (steepness and speed to reach plateau).

The annealing/detection temperature for MNAzyme qPCR used in the art is between 50 and 54° C. This temperature was dictated by the fact that the universal substrates known in the art had a limitation on the temperature at which they were efficiently cleaved with 54° C. being the upper limit for efficient cleavage of the series 1 universal substrates. There is a need for a panel of universal substrates that can be combined in a multiplex reaction and efficiently cleaved at higher temperatures. Not only does this allow greater flexibility in design of primers and partzymes that anneal at higher temperatures and the targeting of G/C rich templates, but it would also enable MNAzyme qPCR detection to be multiplexed with other real-time chemistries well known in the art such as TaqMan® in which the standard annealing/detection temperature ranges from 60-65° C. Utility of universal substrates would be greatly increased if substrates existed that worked well together at a greater range of temperatures.

In this example, two multiplex reactions were performed both comprising MNAzymes designed to detect five different targets, namely human TFRC, HPRT, TP53, RPL13a and CYP2C9 genes. In Multiplex 1, each target MNAzyme was designed to cleave one of the series 1 universal substrates, Sub2, Sub3, Sub4, Sub6 and Sub7 and in Multiplex 2 each target MNAzyme was designed to cleave one of the improved series 2 or 3 universal substrates, Sub55, Sub61, Sub74, Sub79 and Sub80. It will be appreciated that any number of targets can be used in accordance with the method and that those skilled in the art can design appropriate partzymes to detect any target.

The two multiplex reactions were compared to determine the cleavage efficiency of each set of universal substrates by looking at the shape of the curve (steepness and speed to reach plateau). In this example, amplification and detection are compared at a temperature favourable to all substrates, 52° C., and a temperature outside of the efficient range for series 1 substrates, 58° C.

8.1. Partzyme Oligonucleotides

The sequences of the partzymes A and B for each target are listed below from 5' to 3'. For each target, the partzymes were designed to be used with one of the original series 1 universal substrates and one of the novel improved substrates from series 3. In the following sequences, the bases underlined hybridize to the substrate. The "-P" indicates 3' phosphorylation of the oligonucleotide.

```
partzyme A RPL13aA/6-P                                    SEQ ID NO: 157
AATTGACAAATACACAGAGGTCACAACGAGAGGCGTGAT partzyme B RPL13aB/6-P                                    SEQ ID NO: 163
CTGGGAGGAAGGCTAGCTCTCAAGACCCACGGACTCCT partzyme A RPL13aA/80-P                                   SEQ ID NO: 120
AATTGACAAATACACAGAGGTCACAACGAGAGGGCGGTT partzyme B RPL13aB/80-P                                   SEQ ID NO: 121
GGTTCACGGGAGGCTAGCTCTCAAGACCCACGGACTCCT partzyme A CYP2C9A/3-P                                    SEQ ID NO: 96
GGGAAGAGGAGCATTGAGGAACAACGAGGTTGTGCTG partzyme B CYP2C9B/3-P                                    SEQ ID NO: 97
CGGTTGGTGAGGCTAGCTCCGTGTTCAAGAGGAAGC partzyme A CYP2C9A/61-P                                   SEQ ID NO: 98
GGGAAGAGGAGCATTGAGGAACAACGAGGGGTCGAG partzyme B CYP2C9B/61-P                                   SEQ ID NO: 99
TGGCGTGGAGAGGCTAGCTCCGTGTTCAAGAGGAAGC partzyme A TP53A/4-P                                      SEQ ID NO: 164
GACGGAACAGCTTTGAGGTGACAACGAGTGCGCCATG partzyme B TP53B/4-P                                      SEQ ID NO: 165
TACTTCTCCCAAGGCTAGCTCGTGTTTGTGCCTGTCCTGG partzyme A TP53A/79-P:                                    SEQ ID NO: 106
GACGGAACAGCTTTGAGGTGACAACGAGGGGAGAGGA partzyme B TP53B/79-P:                                    SEQ ID NO: 107
GGTTGAAGGGGAGGCTAGCTCGTGTTTGTGCCTGTCCTGG partzyme A TFRCA/2-P:                                     SEQ ID NO: 34
GGAATATGGAAGGAGACTGTCACAACGAGAGGAAACCTT partzyme B TFRCB/2-P:                                     SEQ ID NO: 35
TGCCCAGGGAGGCTAGCTCCTCTGACTGGAAAACAGACT partzyme A TFRCA/74-P:                                    SEQ ID NO: 58
GGAATATGGAAGGAGACTGTCACAACGAGGGGAGTGAT partzyme B TFRCB/74-P:                                    SEQ ID NO: 59
CTGGGAGGGGAGGCTAGCTCCTCTGACTGGAAAACAGACT partzyme A HPRTA/7-P                                      SEQ ID NO: 166
CTGAATAGAAATAGTGATAGATCACAACGAGTGCCATGTTAA partzyme B HPRTB/7-P                                      SEQ ID NO: 167
TATCACAGCCAAGGCTAGCTCATTCCTATGACTGTAGATTTTA partzyme A HPRTA/55-P                                     SEQ ID NO: 168
CTGAATAGAAATAGTGATAGATCACAACGAGAGGTGCGGT partzyme B HPRTB/55-P                                     SEQ ID NO: 169
GAGCTGGGGAGGCTAGCTCATTCCTATGACTGTAGATTTTA
```

8.2. Reporter Substrates

For this example, in each multiplex five different universal substrates were used together in the one reaction chamber. Each universal substrate in each multiplex was labelled with one of five different fluorophores. In the current example, the substrates were 5' end labelled with a fluorophore and 3' end labelled with a quencher moiety (Table 19). Cleavage of the substrates was monitored at various emission and excitation wavelengths (Table 19).

TABLE 19

Substrates and their fluorescent labelling

| Substrate | Name | Fluorophore | Quencher | Excitation* | Emission* |
|---|---|---|---|---|---|
| Multiplex 1 | | | | | |
| Sub2 | Sub2-Q705B2 | Quasar 705 | BHQ2 | 672-684 | 705-730 |
| Sub6 | Sub6-Q670B2 | Quasar 670 | BHQ2 | 620-650 | 675-690 |
| Sub4 | Sub4-TRB2 | Texas Red | BHQ2 | 560-590 | 610-650 |
| Sub7 | Sub7-JB | JOE | BHQ1 | 515-535 | 560-580 |
| Sub3 | Sub3-FIB | 6-FAM | IB | 450-490 | 510-530 |
| Multiplex 2 | | | | | |
| Sub74 | Sub74-Q705B2 | Quasar 705 | BHQ2 | 672-684 | 705-730 |
| Sub80 | Sub80-Q670B2 | Quasar 670 | BHQ2 | 620-650 | 675-690 |
| Sub79 | Sub79-TRIBR | Texas Red | IBR | 560-590 | 610-650 |
| Sub55 | Sub55-HIB | HEX | IB | 515-535 | 560-580 |
| Sub61 | Sub61-FIB | 6-FAM | IB | 450-490 | 510-530 |

^BHQ1; black hole quencher 1, BHQ2; black hole quencher 2, IB; Iowa black ® FQ, IBR; Iowa black ® RQ
*CFX96 Real-Time PCR Detection System (Biorad) excites, and measures emission of, each fluorophore over a range of wavelengths for each channel.

The reporter substrates tested in this example are shown below with the sequence, 5' to 3'. The lower case bases represent RNA and the upper case bases represent DNA.

```
Sub2-Q705B2:                                              SEQ ID NO: 21
AAGGTTTCCTCguCCCTGGGCA

Sub3-FIB:                                                 SEQ ID NO: 22
CAGCACAACCguCACCAACCG

Sub6-Q670B2:                                              SEQ ID NO: 23
ATCACGCCTCguTCCTCCCAG

Sub7-JB:                                                  SEQ ID NO: 24
TTAACATGGCACguTGGCTGTGATA

Sub4-TRB2:                                                SEQ ID NO: 171
CATGGCGCACguTGGGAGAAGTA

Sub61-FIB:                                                SEQ ID NO: 73
CTCGACCCCguCTCCACGCCA

Sub74-Q705B2:                                             SEQ ID NO: 77
ATCACTCCCCguCCCCTCCCAG

Sub79-TRIBR:                                              SEQ ID NO: 80
TCCTCTCCCCguCCCCTTCAACC

Sub80-Q670B2:                                             SEQ ID NO: 81
AACCGCCCTCguCCCGTGAACC

Sub55-HIB:                                                SEQ ID NO: 29
ACCGCACCTCguCCCCAGCTC
```

8.3 Target Sequences and PCR Primers for Amplification of the CYP2C9, TP53, HPRT, TFRC and RPL13a Genes The target PCR amplicons for all five genes were generated by in vitro amplification of Human DNA extracted from IM9 cell line (Promega). The amplicons were generated using the oligonucleotide PCR primers listed 5' to 3' below. The sequence in bold corresponds to a universal tag (U1, U2 or U3) that increases the Tm of the primer without affecting the specificity of the primer to the gene target. This tag improves amplification efficiency in PCR reactions.

SEQ ID NO: 91
Forward primer 5TFRC_U1
GCTAAACAATAACTCAGAACTTACG

SEQ ID NO: 92
Reverse primer 3TFRC_U2
CAGCTTTCTGAGGTTACCATCCTA

SEQ ID NO: 125
Forward primer 5TP53_U3
CTAACTTACTGCCTCTTGCTTCTC

SEQ ID NO: 126
Reverse primer 3TP53_U2
CAGCTCTGTGCGCCGGTCTCTC

SEQ ID NO: 127
Forward primer 5RPL13a_U3
CTAACCGGAAGAAGAAACAGCTCA

SEQ ID NO: 128
Reverse primer 3RPL13a_U2
CAGGAGGAATTAACAGTCTTTATTGG

SEQ ID NO: 129
Forward primer 5CYP2C9_U3
CTAACCTCATGACGCTGCGGAA

SEQ ID NO: 130
Reverse primer 3CYP2C9_U2
CAGATATGGAGTAGGGTCACCCA

SEQ ID NO: 176
Forward primer 5HPRT_U3
CTAACTTTGCTGACCTGCTGGATTA

SEQ ID NO: 177
Reverse primer 3HPRT_U2
CAGCAATAGCTCTTCAGTCTGATAA

8.4. Reaction Components: Amplification and Detection of Target Sequences in a Multiplex MNAzyme qPCR Format Real-time amplification and detection of the target sequences was performed in total reaction volume of 25 μL. All reactions were conducted in a CFX96 Real-Time PCR Detection System (Bio-Rad). The cycling parameters were either, 1) 95° C. for 2 minutes, 40 cycles of 95° C. for 15 seconds and 52° C. for 60 seconds or 2) 95° C. for 2 minutes, 40 cycles of 95° C. for 15 seconds and 58° C. for 60 seconds. Fluorescent data were collected at either the 52° C. or 58° C. step. Each multiplex reaction was run in duplicate and contained 10 mM $MgCl_2$, 200 μM of each dNTP, 10 units Ribosafe RNase inhibitor (Bioline), 1× Immobuffer (Bioline), 2 units MyTaqHS (Bioline). The identity of the partzymes, primers and substrates and their respective concentrations were as listed in Table 20. Reactions contained either DNA template (100 ng or 391 pg) or no target control (NF-$H_2O$).

Multiplex reactions were set up with primers, substrates and their associated partzymes as in Table 20 (Multiplex 1 or Multiplex 2). The same PCR primers were used for both multiplex reactions and all partzymes had the same target-sensing portions. Any differences in efficiency of reactions detecting the same target will therefore be attributable to differences in the efficiency of cleavage of the substrates.

TABLE 20

| Target | Oligonucleotide combinations used for each multiplex reaction ||||||
|---|---|---|---|---|---|
| | 5' primer (20 nM except * = 80 nM) | 3'Primer (400 nM except * = 200 nM) | PzA & PzB (200 nM each) || Substrate (200 nM each) |
| Multiplex 1 ||||||
| TFRC | 5TFRC_U3 | 3TFRC_U2 | TFRCA/2-P SEQ ID NO: 34 | TFRCB5/2-P SEQ ID NO: 35 | Sub2-Q705B2 SEQ ID NO: 21 |
| HPRT | 5HPRT_U3* | 3HPRT_U2 | HPRTA/7-P SEQ ID NO: 166 | HPRTB5/7-P SEQ ID NO: 167 | Sub7-JB SEQ ID NO: 24 |
| TP53 | 5TP53_U1 | 3TP53_U2* | TP53A/4-P SEQ ID NO: 164 | TP53B5/4-P SEQ ID NO: 165 | Sub4-TRB2 SEQ ID NO: 171 |
| RPL13a | 5RPL13a_U1 | 3RPL13a_U2 | RPL13aA/6-P SEQ ID NO: 157 | RPL13aB/6-P SEQ ID NO: 163 | Sub6Q670B2 SEQ ID NO: 23 |
| CYP2C9 | 5CYP2C9_U1 | 3CYP2C9_U2 | CYP2C9A/3-P SEQ ID NO: 96 | CYP2C9B/3-P SEQ ID NO: 97 | Sub3-FIB SEQ ID NO: 22 |
| Multiplex 2 ||||||
| TFRC | 5TFRC_U3 | 3TFRC_U2 | TFRCA/74-P SEQ ID NO: 58 | TFRCB/74-P SEQ ID NO: 59 | Sub74-Q705B2 SEQ ID NO: 77 |
| HPRT | 5HPRT_U3* | 3HPRT_U2 | HPRTA/55-P SEQ ID NO: 168 | HPRTB/55-P SEQ ID NO: 169 | Sub55-HIB SEQ ID NO: 29 |
| TP53 | 5TP53_U1 | 3TP53_U2* | TP53A/79-P SEQ ID NO: 106 | TP53B/79-P SEQ ID NO: 107 | Sub79-TRIBR SEQ ID NO: 80 |
| RPL13a | 5RPL13a_U1 | 3RPL13a_U2 | RPL13aA/80-P SEQ ID NO: 120 | RPL13aB/80-P SEQ ID NO: 121 | Sub80-Q670B2 SEQ ID NO: 81 |
| CYP2C9 | 5CYP2C9_U1 | 3CYP2C9_U2 | CYP2C9A/61-P SEQ ID NO: 98 | CYP2C9B/61-P SEQ ID NO: 99 | Sub61-FIB SEQ ID NO: 73 |

8.5. Results: Amplification of Target and Cleavage of Reporter Substrate in Multiplex MNAzyme qPCR Format Each multiplex reaction containing human genomic DNA showed an increase in fluorescence over time for the real-time detection of the genes CYP2C9, TP53, HPRT, RPL13a and TFRC. For all reactions, the fluorescence of the no-DNA target control was lower than that in the DNA target-containing reactions. This demonstrates that the increase in fluorescence produced in target-containing reactions is due to target dependent assembly of catalytically active MNAzymes that then cleaved one of the universal substrates.

Figure 11:
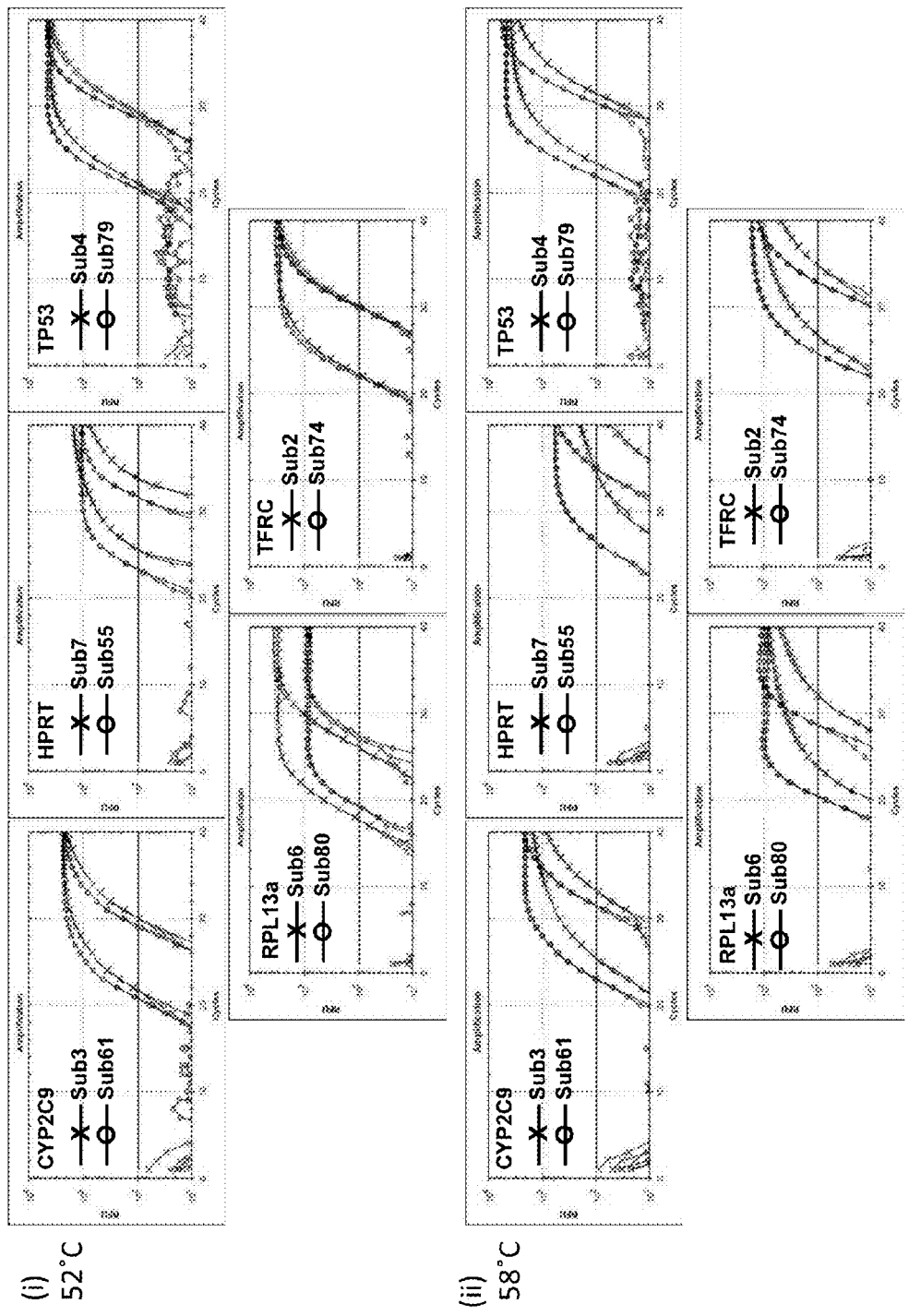
FIG. 11 illustrates exponential amplification plots generated with amplification at either 52° C. (Panel (i)) or 58° C. (Panel (ii)) for two multiplex MNAzyme qPCR reactions Multiplex 1 using series 1 substrates (Sub2, Sub3, Sub4, Sub6 and Sub7) and Multiplex 2 using series 2 and 3 substrates (Sub55, Sub61, Sub74, Sub79 and Sub80). Both multiplexes measured the human genes TFRC, HPRT, TP53, RPL13a and CYP2C9 in a single reaction vessel. For each different gene measured in the two multiplex formats the same primer sets and genomic DNA were used at both temperatures and for all universal substrates, and all partzymes had the same catalytic domains and target-sensor regions matched to the particular gene. The only difference between reactions was the substrate-sensor arms of the partzymes and the fluorescently labelled universal substrates. The universal substrates tested with each gene are indicated at the top left of each plot. The amplification plots for Multiplex 1 (crosses) and Multiplex 2 (circles) were overlayed to allow for a direct comparison between the two multiplexes at two different DNA concentrations, 100 ng (cross and circle plot on the left) and 391 pg (cross and circle plot on the right). The difference in the shape of the amplification plots correlated with efficiency of cleavage of the universal substrates. The steeper the curves and the earlier Ct values indicate a faster number of cycles to achieve a threshold fluorescence, and therefore indicate more efficiently cleaved universal substrates.

The amplification plots of the CYP2C9, TP53, HPRT, RPL13a and TFRC genes at 52° C. demonstrated that Multiplex 2 (FIG. 11, (i)), which used the new improved series 2 and 3 universal substrates, had steeper curves that reached plateau faster than those observed for Multiplex 1 (FIG. 11, (i)), which used series 1 universal substrates. There was only a small difference in the amplification plots for detection of TFRC with Sub2 versus Sub74 at 52° C. One skilled in the art would appreciate that all of the amplification plots of Multiplex 1, using series 1 vs series 2 and 3 substrates, are of a sufficiently good quality to be readily acceptable in the field for detection of these targets.

The amplification plots of the CYP2C9, TP53, HPRT, RPL13a and TFRC genes at 58° C. demonstrated that Multiplex 2 (FIG. 11, (ii)), which used the new improved series 2 and 3 universal substrates, had considerably steeper curves and reached plateau substantially faster than Multiplex 1 (FIG. 11, (ii)), which used series 1 universal substrates. Further, one skilled in the art would acknowledge that the amplification curves produced by use of Sub2, Sub3, Sub6 and Sub7 in Multiplex 1 may not be of sufficient quality for robust detection of target and thus may not be generally acceptable in the field.

Overall, the new series 2 and 3 substrates show improved quality, and therefore robustness, of multiplex data at temperatures currently in use with MNAzyme qPCR reactions and enable multiplex detection at a temperature much higher than previously capable. The new design guidelines increase the probability of designing universal substrates that extend the ability to multiplex at temperatures currently used for MNAzyme qPCR and that produce robust data at higher reaction temperatures.

Example 9

Use of Universal Substrates, Designed to be Functional at Various Temperatures, with MNAzymes in Real-Time PCR A new series of highly active substrates has been invented, using a novel set of design guidelines, for use with the 10-23 DNAzyme or MNAzyme based on the 10-23 DNAzyme.

MNAzymes can be tailored to produce a detectable effect, via cleavage or ligation of a substrate, at various temperatures. The efficiency and stringency of catalytic activity of an MNAzyme or DNAzyme can be manipulated by changing the reaction temperature. Another way to optimise efficiency and stringency of catalytic activity is to modify the Tm and/or length of the substrate(s) and matching partzymes or matching DNAzyme. The Tm of a substrate can be increased by adding nucleotides on to the 5' and/or 3' ends of the substrate sequence. These changes can be made within the design guidelines. The nucleotides chosen for this extension can also have an effect on the Tm. Addition of extra G or C bases to the 3' or 5' end will have a greater impact on the Tm than the addition of extra A or T bases. Similarly, the Tm of substrates can be reduced by removing nucleotides from the 3' or 5' end. MNAzyme partzymes and DNAzymes can be truncated or extended to match the adjusted substrate sequence.

In this example, the length and base composition of the series 2 substrate, Sub55, was modified to produce a range of derivative substrates with a variety of Tm's (Table 21). Modifications included truncating the substrate by removal of one to three nucleotides from each of the 5' and 3' ends; extending the substrate by the addition of nucleotides to both of the 5' and 3' ends. The effect of adding different nucleotides to produce this extension was also tested by designing substrates with either additional A or C nucleotides at the 5' and 3' ends. The resulting substrates were then tested in a MNAzyme qPCR reaction to assess the flexibility of design of derivatives of substrates and their utility at a range of temperatures. The PCR amplification and MNAzyme-mediated detection were performed in a one-step process, wherein PCR amplification and MNAzyme-mediated detection occurred simultaneously in a single tube. The efficiency of cleavage of substrates can be measured by the Ct value generated at several annealing temperatures. Reactions that produce a lower Ct value are indicative of more efficient cleavage of a specific substrate since such reactions reach the threshold cycle faster.

TABLE 21

Sub55 and derivatives

| Name | Sequence^ | Length (bp) | Tm* |
|---|---|---|---|
| Sub55(16) | GCACCTCguCCCCAGC<br>SEQ ID NO: 172 | 16 | 52 |
| Sub55(18) | CGCACCTCguCCCCAGCT<br>SEQ ID NO: 173 | 18 | 58 |
| Sub55 | ACCGCACCTCguCCCCAGCTC<br>SEQ ID NO: 29 | 21 | 68 |
| Sub55(23A) | AACCGCACCTCguCCCCAGCTCA<br>SEQ ID NO: 174 | 23 | 72 |
| Sub55(23C) | CACCGCACCTCguCCCCAGCTCC<br>SEQ ID NO: 175 | 23 | 76 |

^All sequences written 5' to 3'; uppercase represents DNA and lowercase represents RNA
*Tm given here equates to the melting temperature of the bases bound to the two partzymes calculated using the Wallace rule. When the substrate is bound to the MNAzyme based on the 10-23 DNAzyme, or the 10-23 DNAzyme itself, the "g" ribonucleotide remains unbound therefore does not contribute to the overall bound Tm.

9.1. Partzyme Oligonucleotides

In the experiments conducted to measure the rate of catalytic activity of Sub55 and its' derivatives described in Table 21, the partzyme oligonucleotides A and B were designed with target sensor arms complementary to the human TFRC gene. The sequences of the A and B partzymes are listed below from 5' to 3', where the bases underlined hybridize to the substrate. The "-P" indicates 3' phosphorylation of the oligonucleotide.

SEQ ID NO: 179
partzyme A TFRCA/55(18)-P:
GGAATATGGAAGGAGACTGTCACAACGA<u>GAGGTGCG</u>

```
                                         SEQ ID NO: 180
partzyme B TFRCB/55(18)-P:
AGCTGGGGAGGCTAGCTCCTCTGACTGGAAAACAGACT SEQ ID NO: 181
partzyme A TFRCA/55(16)-P:
GGAATATGGAAGGAGACTGTCACAACGAGAGGTGC SEQ ID NO: 182
partzyme B TFRCB/55(16)-P:
GCTGGGGAGGCTAGCTCCTCTGACTGGAAAACAGACT SEQ ID NO: 183
partzyme A TFRCA/55(23A)-P:
GGAATATGGAAGGAGACTGTCACAACGAGAGGTGCGGTT SEQ ID NO: 184
partzyme B TFRCB/55(23A)-P:
TGAGCTGGGGAGGCTAGCTCCTCTGACTGGAAAACAGACT SEQ ID NO: 185
partzyme B TFRCA/55(23C)-P:
GGAATATGGAAGGAGACTGTCACAACGAGAGGTGCGGTG SEQ ID NO: 186
partzyme B TFRCB/55(23C)-P:
GGAGCTGGGGAGGCTAGCTCCTCTGACTGGAAAACAGACT SEQ ID NO: 46
partzyme A TFRCA/55-P:
GGAATATGGAAGGAGACTGTCACAACGAGAGGTGCGGT SEQ ID NO: 45
partzyme B TFRCB/55-P:
GAGCTGGGGAGGCTAGCTCCTCTGACTGGAAAACAGACT
```

9.2. Reporter Substrates

In the current example, the substrates were end labelled with a Quasar 670 moiety at the 5' end and a BHQ2 moiety at the 3' end. Cleavage of the substrates was monitored at 665 nm (Quasar 670 emission wavelength) with excitation at 635 nm (Quasar 670 excitation wavelength). The reporter substrates tested in this example are shown below with the sequence, 5' to 3'. The lower case bases represent RNA and the upper case bases represent DNA.

```
                                         SEQ ID NO: 29
Sub55-Q670B2:
ACCGCACCTCguCCCCAGCTC

SEQ ID NO: 172
Sub55(16)-Q670B2:
GCACCTCguCCCCAGC

SEQ ID NO: 173
Sub55(18)-Q670B2:
CGCACCTCguCCCCAGCT

SEQ ID NO: 174
Sub55(23A)-Q670B2:
AACCGCACCTCguCCCCAGCTCA

SEQ ID NO: 175
Sub55(23C)-Q670B2:
CACCGCACCTCguCCCCAGCTCC
```

9.3. Target Sequence and PCR Primers for Amplification of TFRC

The target sequence for this example was a PCR amplicon generated by in vitro amplification of human genomic DNA, extracted from the IM9 cell line (Promega), using the oligonucleotide PCR primers listed below. Primer sequences are listed 5' to 3'.

```
                                         SEQ ID NO: 187
Forward primer 5TFRC:
AACAATAACTCAGAACTTACG SEQ ID NO: 188
Reverse primer 3TFRC:
CTTTCTGAGGTTACCATCCTA
```

9.4. Reaction Components: Amplification and Detection of Target Sequence

Real-time amplification and detection of the target sequence was performed in a total reaction volume of 25 µL. All reactions were conducted in a Mx3005P QPCR system (Stratagene/Agilent). The cycling parameters were varied by the annealing temperature, (underlined as follows), and were either, 1) 95° C. for 10 minutes, 5 cycles of 95° C. for 15 seconds and 55° C. for 30 seconds, 50 cycles of 95° C. for 15 seconds and 50° C. for 60 seconds, or 2) 95° C. for 10 minutes, 5 cycles of 95° C. for 15 seconds and 55° C. for 30 seconds, 50 cycles of 95° C. for 15 seconds and 52° C. for 60 seconds, or 3) 95° C. for 10 minutes, 5 cycles of 95° C. for 15 seconds and 55° C. for 30 seconds, 50 cycles of 95° C. for 15 seconds and 55° C. for 60 seconds, or 4) 95° C. for 10 minutes, 5 cycles of 95° C. for 15 seconds and 55° C. for 30 seconds, 50 cycles of 95° C. for 15 seconds and 60° C. for 60 seconds.

All fluorescent data were collected at the annealing temperature. Reactions were set up with substrates and their associated partzymes as in Table 22. Each set of reaction conditions were run in duplicate and contained 40 nM 5TFRC, 200 nM of 3TFRC, 200 nM each of partzyme A and partzyme B, 200 nM of substrate, 8 mM MgCl$_2$, 200 µM of each dNTP, 10 units Rnasin (Promega), 1× Immobuffer (Bioline), 1 unit of Immolase (Bioline) and either genomic DNA template (100 ng) or no target (NF-H$_2$O). Separate reactions were set up to test each substrate with its matched partzymes. The same PCR primers were used for all reactions and all partzymes had the same target-sensing portions. Any differences in efficiency of reactions will therefore be attributable to differences in the efficiency of cleavage of the substrates at various temperatures.

TABLE 22

| Partzyme combinations used for each universal substrate | | |
| --- | --- | --- |
| Substrate | Partzyme A | Partzyme B |
| Sub55 | TFRCA/55-P | TFRCB/55-P |
| SEQ ID NO: 29 | SEQ ID NO: 46 | SEQ ID NO: 45 |
| Sub55(16) | TFRCA/55(16)-P | TFRCB/55(16)-P |
| SEQ ID NO: 172 | SEQ ID NO: 181 | SEQ ID NO: 182 |
| Sub55(18) | TFRCA/55(18)-P | TFRCB/55(18)-P |
| SEQ ID NO: 173 | SEQ ID NO: 179 | SEQ ID NO: 180 |
| Sub55(23A) | TFRCA/55(23A)-P | TFRCB/55(23A)-P |
| SEQ ID NO: 174 | SEQ ID NO: 183 | SEQ ID NO: 184 |
| Sub55(23C) | TFRCA/55(23C)-P | TFRCB/55(23C)-P |
| SEQ ID NO: 175 | SEQ ID NO: 185 | SEQ ID NO: 186 |

9.5. Results: Amplification of Target and Cleavage of Reporter Substrate

Each reaction containing human genomic DNA showed an increase in fluorescence over time for real time detection of the TFRC gene using Sub55 and various derivatives. The fluorescence of the no-DNA target control was lower than that in the DNA target-containing reactions. This demonstrates that the increase in fluorescence produced in target-containing reactions is due to target dependent assembly of catalytically active MNAzymes that then cleaved one of the universal substrates.

The efficiency of the reactions, measured by the Ct, was dependent on the compatibility of the reaction temperature (annealing/cleavage temperature) and the Tm of the substrate used in the reaction. The various Sub55 derivatives have different lengths and nucleotide compositions and thus different melting temperatures (Tm) and are therefore expected to perform differently at the various annealing temperatures tested (50, 52, 55, and 60° C.). The results, in Table 23, show the Ct for each substrate at the different reaction temperatures. The Ct values in bold indicate the substrates(s) which performed most efficiently at the temperatures indicated.

At lower temperatures the shorter substrate (Sub55(18)) performed better (had the lowest Ct value). As the annealing temperature increased, substrates with increased length and therefore Tm, performed optimally. One skilled in the art could produce derivatives of substrates that could be efficiently cleaved at a chosen reaction temperature by lengthening or shortening the substrate arms from the 5' and/or 3' ends, and/or changing the nucleotide composition at the 5' and 3' ends of the substrate.

TABLE 23

Ct values for MNAzyme qPCR performed using Sub55 and derivatives at various annealing temperatures

| Name | 50° C. | 52° C. | 55° C. | 60° C. |
|---|---|---|---|---|
| Sub55(16) | 26.1 | 26.7 | 31.2 | n/a |
| Sub55(18) | 23.9 | 23 | 24.8 | n/a |
| Sub55 | 24.4 | 22.8 | 23.0 | 26.8 |
| Sub55(23A) | 25.3 | 23.9 | 23.0 | 25.8 |
| Sub55(23C) | 25.8 | 24.1 | 23.9 | 26.2 |

Example 10

Use of Universal Substrates with MNAzymes qPCR at an Annealing Temperature of 58° C.

MNAzymes can be used to monitor amplification of target nucleic acids in real-time using in vitro target amplification methods such as PCR. Furthermore, real-time monitoring during qPCR using MNAzyme substrates labelled with fluorophore and quencher pairs generates a curve on which a threshold line, of an arbitrary level of fluorescence, can be placed over the exponential phase of the reactions, producing a value which can be known as a Ct (cycle threshold). Reactions that produce a lower Ct value are indicative of more efficient cleavage of a specific substrate since such reactions reach the threshold cycle faster. In this example, amplification and detection are performed in a one-step process, wherein PCR amplification and MNAzyme-mediated detection occur simultaneously in a single tube. Where all other reaction conditions are the same the Ct value can be influenced by the sequence of the universal substrate. The annealing/detection temperature for MNAzyme qPCR used in the art is between 50 and 54° C. This temperature was dictated by the fact that the universal substrates known in the art had a limitation on the temperature at which they were efficiently cleaved with 54° C. being the upper limit for the series 1 universal substrates. There is a need for universal substrates that cleave at higher temperatures to allow greater flexibility in design of primers and partzymes that anneal at higher temperatures. This design flexibility for primers and partzymes could be of great benefit for many applications such as genetic targets of interest that have high percentages of G and C bases in their sequence, requiring higher reaction temperatures and hence partzymes and primers with higher Tms for specific detection.

Investigation into efficiency of cleavage of substrates based on the performance of the series 1 and 2 substrates, lead to the development of guidelines to aid in a third round of substrate designs, resulting in the series 3 substrates. These guidelines included but were not limited to (i) seven or more cytosine nucleotides in the ten bases surrounding the ribonucleotides ($N_4$-$N_{13}$), (ii) bases immediately adjacent to the ribonucleotides are cytosines ($N_8$ and $N_9$) (iii) total content of substrate has >64% pyrimidines and (iv) total Tm of the oligonucleotide is 66° C. or greater (where this latter guideline is only applicable if the reaction temperature for substrate cleavage is above 50° C.).

In this example, the series 2 universal substrate, Sub59 is compared to the series 3 substrate, Sub77 to compare the cleavage efficiency in real-time PCR at 58° C. to ensure that the design guidelines produce universal substrates with a high probability of applicability to MNAzyme qPCR at an elevated temperature. The level of cleavage efficiency was determined by measuring the Ct value for reactions containing different universal substrates.

10.1. Partzyme Oligonucleotides

In the experiments conducted to measure the efficiency of cleavage of the series 2 and series 3 universal substrate in real-time PCR, all the partzyme oligonucleotides A and B were designed with sensor arms complementary to the same sequence of the human TFRC gene. The sequences of the A and B partzymes are listed below from 5' to 3', where the bases underlined hybridize to their matched universal substrate. The "-P" indicates 3' phosphorylation of the oligonucleotide.

```
                                            SEQ ID NO: 47
    partzyme A TFRCA/59-P:
    GGAATATGGAAGGAGACTGTCACAACGAAGGGAGGAGG SEQ ID NO: 62
    partzyme A TFRCA/77-P:
    GGAATATGGAAGGAGACTGTCACAACGAGAGGGAGGAG SEQ ID NO: 63
    partzyme B TFRCB/77-P:
    AGGAGGAGGGAGGCTAGCTCCTCTGACTGGAAAACAGACT
```

10.2. Reporter Substrates

The reporter substrates for this example are shown below with the sequence, 5' to 3'. The lower case bases represent RNA and the upper case bases represent DNA. In the current example, the substrates were end labelled with a 6-FAM moiety at the 5' end (indicated by a "F" in the name of the substrates below) and an Iowa Black' FQ quencher moiety at the 3' end (indicated by a "IB" in the name of the substrates below). Cleavage of the substrates was monitored at 530 nm (FAM emission wavelength on Mx3005P (Stratagene)) with excitation at 485 nm (FAM excitation wavelength on Mx3005P (Stratagene)).

```
                                            SEQ ID NO: 33
    Sub59-FIB:
    CCTCCTCCCTguCCCTCCTCCT
```

-continued

SEQ ID NO: 79
Sub77-FIB:
CTCCTCCCTCguCCCTCCTCCT

10.3. Target' Sequence and PCR Primers for Amplification of TFRC

The target sequence for this example was a PCR amplicon from the TFRC gene generated by in vitro amplification of human genomic DNA, extracted from the IM9 cell line (Promega), using the oligonucleotide PCR primers listed below. Primer sequences are listed 5' to 3'.

SEQ ID NO: 187
Forward primer 5TFRC:
AACAATAACTCAGAACTTACG

SEQ ID NO: 188
Reverse primer 3TFRC:
CTTTCTGAGGTTACCATCCTA

10.4. Reaction Components: Amplification and Quantification of Target Sequence Real-time PCR amplification and detection of the target sequence was performed in a total reaction volume of 25 µL. All reactions were conducted in an Mx3005P QPCR system (Stratagene). Reactions were set up with substrates and their associated partzymes as in Table 24. The cycling parameters were, 95° C. for 2 minutes, 40 cycles of 95° C. for 15 seconds and 58° C. for 60 seconds (data collected at the 58° C. step). Each set of reaction conditions were run in duplicate and contained 40 nM 5TFRC, 200 nM of 3TFRC, 200 nM each of partzyme A and partzyme B, 200 nM substrate, 8 mM MgCl$_2$, 200 µM of each dNTP, 10 units RNasin (Promega), 1× Immobuffer (Bioline), 2 units of MyTaqHS™ DNA polymerase (Bioline) and either genomic DNA template (50 ng) or no target (NF-H$_2$O).

TABLE 24

Partzyme combinations used for each universal substrate

| Substrate | Partzyme A | Partzyme B |
|---|---|---|
| Sub59 | TFRCA/59-P | TFRCB/77-P |
| SEQ ID NO: 33 | SEQ ID NO: 47 | SEQ ID NO: 63 |
| Sub77 | TFRCA/77-P | TFRCB/77-P |
| SEQ ID NO: 79 | SEQ ID NO: 62 | SEQ ID NO: 63 |

10.5. Results: Amplification of Target and Cleavage of Reporter Substrate

Each MNAzyme qPCR reaction containing human genomic DNA showed an increase in fluorescence over time for the real-time detection of TFRC from human genomic DNA. For all reactions the fluorescence of the no-DNA target control was lower than that in the DNA target-containing reactions. This demonstrates that the increase in fluorescence produced in target-containing reactions is due to target dependent assembly of catalytically active MNAzymes that then cleaved one of the universal reporter substrates.

The reactions with the series 2, substrate Sub59, showed an averaged Ct value of 28.5 while the reactions with the series 3 substrate Sub77 showed an averaged Ct value of 26.5.

Of note is that Sub59 and Sub77 have the same Tm and % C/T but differ in the number of cytosines in the central region $N_4$-$N_{13}$ and the composition of $N_8$. In the central region surrounding the ribonucleotides Sub77 has a cytosine in position $N_8$ which appears to have led to improved cleavage efficiency over Sub59 indicated by a lower Ct value (26.5). Sub59 contains a thymine at position Ng and an added cytosine at the distal end of the 5' arm which has led to a reduced cleavage reaction and hence a higher Ct value (28.5).

Of note is the importance of the nature of the nucleotide sequence of the efficiently cleaved substrate and the proximity of specific nucleotides to the ribonucleotides of the substrates. These features form the basis of a set of guidelines that result in universal substrates with a higher probability of being cleaved efficiently at elevated temperatures. These design guidelines include but are not limited to (not all may be necessary): (i) seven or more cytosine nucleotides in the ten bases surrounding the ribonucleotides ($N_4$-$N_{13}$); (ii) the bases immediately adjacent to the ribonucleotides are cytosines ($N_8$ and $N_9$); (iii) total content of substrate has >64% pyrimidine's; (iv) total Tm of the oligonucleotide is 66° C. or greater (where this latter guideline is only applicable if the reaction temperature for substrate cleavage is above 50° C.) (Table 25). The earlier Ct value for the series 3 substrate, Sub77, is expected as this substrate complies with all of these design guidelines, while Sub59 complies with only two of these design guidelines (Table 25).

TABLE 25

Efficiency of cleavage of universal substrates (listed in order of cleavage efficiency based on Ct)

| Name Sequence^ | # C's $N_4$-$N_{13}$ | CguC | % C/T+ | Tm* | Ct | #(i - iv)~ |
|---|---|---|---|---|---|---|
| Sub77 CTCCT<u>CCCT</u>Cgu<u>CCCT</u>CCTCCT<br>SEQ ID NO: 79 | 8 | Yes | 100 | 70 | 26.5 | 4 |
| Sub59 CCTCC<u>TCCCT</u>gu<u>CCCT</u>CCTCCT<br>SEQ ID NO: 33 | 6 | No | 100 | 70 | 28.5 | 2 |

^uppercase bases represent DNA and lowercase bases represent RNA and position of base in a substrate is represented by (N$_x$)-N$_1$-N$_2$-N$_3$-N$_4$-N$_5$-N$_6$-N$_7$-N$_8$-rR-rY-N$_9$-N$_{10}$-N$_{11}$-N$_{12}$-N$_{13}$-N$_{14}$-N$_{15}$-(N$_x$)
+% C/T (pyrimidines) of sequence length shown above for each substrate, does not include ribonucleotides
*Tm given here equates to the melting temperature of the bound bases calculated using the Wallace rule - only calculated for bases that hybridize to their complement. When the substrate is bound to the MNAzyme based on the 10-23 DNAzyme the "g" ribonucleotide remains unbound therefore does not contribute to the overall bound Tm.
~The number of the design guidelines (i), (ii), (iii) and/or (iv) that have been met by the substrate sequence.

REFERENCES

PCT International Publication No. WO/2007/041774
PCT International Publication No. WO/2008/040095
PCT International Publication No. WO/2008/122084
U.S. Pat. No. 4,683,202
U.S. Pat. No. 4,683,195
U.S. Pat. No. 4,800,159
U.S. Pat. No. 4,965,188
U.S. Pat. No. 5,176,995
US publication number 2007-0231810
US publication number 2010-0136536
US publication number 2011-0143338
Cairns, M. J, Hopkins, T. M., Witherington, G., Wang, L. and Sun, L (1999) Target site selection for an RNA-cleaving catalytic DNA. Nat. Biotech. 17: 480-486.
Cruz, R. P., Withers, J. B. and Li, Y. (2004) Dinucleotide junction cleavage versatility of 8-17 deoxyribozyme. Chem Biol. January; 11(1): 57-67.
Perreault, J., Labuda, D., Usman, N., Yang, J. and Cedergren, R. (1991) Relationship between 2'-hydroxyls and magnesium binding in the hammerhead RNA domain: a model for ribozyme catalysis. Biochemistry 30(16): 4020-5.
Perreault, J., Wu, T., Cousineau, B., Ogilvie, K. and Cedergren, R. (1990) Mixed deoxyribo- and ribo-oligonucleotides with catalytic activity. Nature 344(6266): 565-7.
Silverman, S. (2004) Breaking up is easy to do (if you're a DNA enzyme that cleaves RNA). Chem Biol. January; 11(1): 7-8. Wallace, R. B., Shaffer, J., Murphy, R. F.,
Bonner, J., Hirose, T. and Itakura K. (1979) Hybridization of synthetic oligodeoxyribonucleotides to $\phi_x$174 DNA: the effect of single base pair mismatch. Nucl. Acids Res. 6(11): 3543-3558.
Zaborowska, Z., Furste, J., Erdmann, V. and Kurreck, J. (2002) Sequence requirements in the catalytic core of the "10-23" DNA enzyme. J Biol Chem. 277(43): 240617-22.

The invention claimed is:

1. An isolated polynucleotide substrate for a catalytic nucleic acid enzyme, said polynucleotide substrate comprising a sequence $N_1$-$N_2$-$N_3$-$N_4$-$N_5$-$N_6$-$N_7$-$N_8$-rR-rY-$N_9$-$N_{10}$-$N_{11}$-$N_{12}$-$N_{13}$-$N_{14}$-$N_{15}$ wherein:
rR is a purine ribonucleotide;
rY is a pyrimidine ribonucleotide;
each of $N_1$-$N_{15}$ are deoxyribonucleotides;
six or more of $N_5$-$N_{13}$ are cytosine nucleotides; and
less than three of $N_9$-$N_{15}$ are guanine nucleotides;
wherein the polynucleotide substrate comprises or consists of a sequence defined by any one of SEQ ID NOs: 25-27, 29-30, 33, 72-90, or 172-175.

2. The isolated polynucleotide substrate according to claim 1, wherein seven or more of $N_5$-$N_{13}$ are cytosine nucleotides and the polynucleotide substrate comprises or consists of a sequence defined by any one of SEQ ID NOs: 29, 73, 76-80, 82-83, 85-90, or 172-175.

3. The isolated polynucleotide substrate according to claim 1, wherein seven or more of $N_4$-$N_{13}$ are cytosine nucleotides and the polynucleotide substrate comprises or consists of a sequence defined by any one of SEQ ID NOs: 27, 29, 73, 76-83, 85-90, or 172-175.

4. The isolated polynucleotide substrate according to claim 1, wherein $N_8$ and $N_9$ are cytosine nucleotides, and the polynucleotide substrate comprises or consists of a sequence defined by any one of SEQ ID NOs: 25-26, 29-30, 72-90, or 172-175.

5. The isolated polynucleotide substrate according to claim 1, wherein one or none of $N_9$-$N_{15}$ are guanine nucleotides and the polynucleotide substrate comprises or consists of a sequence defined by any one of SEQ ID NOs: 25-27, 29-30, 33, 72-80, 82-90, or 172-175.

6. The isolated polynucleotide substrate according to claim 1, wherein eleven, twelve, or more than twelve of $N_1$-$N_{15}$ are pyrimidine nucleotides and the polynucleotide substrate comprises or consists of a sequence defined by any one SEQ ID NOs: 25-27, 29, 33, 73-90 or 173-175.

7. The isolated polynucleotide substrate of claim 1, further comprising a detectable label for detecting the polynucleotide substrate.

8. The isolated polynucleotide substrate of claim 1, further comprising a detectable portion and a quencher portion, wherein a detectable effect provided by the detectable portion is increased or decreased upon modification of the polynucleotide substrate by said catalytic nucleic acid enzyme.

9. The isolated polynucleotide substrate of claim 1, wherein:
(i) the purine ribonucleotide comprises guanine;
(ii) the pyrimidine ribonucleotide comprises uracil; or
(iii) the purine ribonucleotide comprises guanine and the pyrimidine ribonucleotide comprises uracil.

10. The isolated polynucleotide substrate of claim 1, wherein said catalytic nucleic acid enzyme is:
(a) a multi-component nucleic acid enzyme (MNAzyme) and said portion binds to at least one substrate arm of said MNAzyme; or
(b) a DNAzyme.

11. A method for detecting the presence of at least one target comprising:
(a) providing two or more oligonucleotide partzymes, wherein at least a first oligonucleotide partzyme and a second oligonucleotide partzyme self-assemble in the presence of said target to form at least a first catalytically active multi-component nucleic acid enzyme (MNAzyme);
(b) providing an isolated polynucleotide substrate comprising a sequence $N_1$-$N_2$-$N_3$-$N_4$-$N_5$-$N_6$-$N_7$-$N_8$-rR-rY-$N_9$-$N_{10}$-$N_{11}$-$N_{12}$-$N_{13}$-$N_{14}$-$N_{15}$ wherein:
rR is a purine ribonucleotide;
rY is a pyrimidine ribonucleotide;
each of $N_1$-$N_{15}$ are deoxyribonucleotides;
six or more of $N_5$-$N_{13}$ are cytosine nucleotides; and
less than three of $N_9$-$N_{15}$ are guanine nucleotides, wherein said polynucleotide substrate is capable of being modified by said first MNAzyme, wherein said modification of said polynucleotide substrate by said MNAzyme provides a detectable effect;
(c) contacting said two or more oligonucleotide partzymes with a sample putatively containing said target under conditions permitting:
(1) the self-assembly of said at least first MNAzyme, and
(2) the catalytic activity of said at least first MNAzyme; and
(d) detecting said detectable effect.

12. The method according to claim 11, wherein the first and second oligonucleotide partzymes comprise respective sequences defined by: SEQ ID NO: 9 and SEQ ID NO: 10; SEQ ID NO: 11 and SEQ ID NO: 12; SEQ ID NO: 13 and SEQ ID NO: 14; SEQ ID NO: 16 and SEQ ID NO: 14; SEQ ID NO: 17 and SEQ ID NO: 18; SEQ ID NO: 40 and SEQ ID NO: 41; SEQ ID NO: 42 and SEQ ID NO: 43; SEQ ID NO: 44 and SEQ ID NO: 45; SEQ ID NO: 46 and SEQ ID NO: 45; SEQ ID NO: 47 and SEQ ID NO: 63; SEQ ID NO: 48 and SEQ ID NO: 49; SEQ ID NO: 50 and SEQ ID NO: 51; SEQ ID NO: 52 and SEQ ID NO: 51; SEQ ID NO: 38 and SEQ ID NO: 55; SEQ ID NO: 56 and SEQ ID NO: 57; SEQ ID NO: 58 and SEQ ID NO: 59; SEQ ID NO: 60 and SEQ ID NO: 61; SEQ ID NO: 62 and SEQ ID NO: 63; SEQ ID NO: 64 and SEQ ID NO: 65; SEQ ID NO: 66 and SEQ ID NO: 67; SEQ ID NO: 62 and SEQ ID NO: 68; SEQ ID NO: 69 and SEQ ID NO: 70; SEQ ID NO: 46 and SEQ ID NO: 55; SEQ ID NO: 46 and SEQ ID NO: 59; SEQ ID NO: 38 and SEQ ID NO: 45; SEQ ID NO: 58 and SEQ ID NO: 45; SEQ ID NO: 62 and SEQ ID NO: 45; SEQ ID NO: 46 and SEQ ID NO: 63; SEQ ID NO: 71 and SEQ ID NO: 68; SEQ ID NO: 98 and SEQ ID NO: 99; SEQ ID NO: 100 and SEQ ID NO: 103; SEQ ID NO: 104 and SEQ ID NO: 105; SEQ ID NO: 106 and SEQ ID NO: 107; SEQ ID NO: 108 and SEQ ID NO: 109; SEQ ID NO: 110 and SEQ ID NO: 111; SEQ ID NO: 112 and SEQ ID NO: 113; SEQ ID NO: 116 and SEQ ID NO: 117; SEQ ID NO: 118 and SEQ ID NO: 119; SEQ ID NO: 120 and SEQ ID NO: 121; SEQ ID NO: 122 and SEQ ID NO: 119; SEQ ID NO: 155 and SEQ ID NO: 156; SEQ ID NO: 157 and SEQ ID NO: 158; SEQ ID NO: 159 and SEQ ID NO: 160; SEQ ID NO: 168 and SEQ ID NO: 169; SEQ ID NO: 179 and SEQ ID NO: 180; SEQ ID NO: 181 and SEQ ID NO: 182; SEQ ID NO: 183 and SEQ ID NO: 184 or SEQ ID NO: 185 and SEQ ID NO: 186.

13. The method of claim 11, wherein said detecting in part (d) comprises use of fluorescence spectroscopy, surface plasmon resonance, mass spectroscopy, NMR, electron spin resonance, polarization fluorescence spectroscopy, circular dichroism, immunoassay, chromatography, radiometry, electrochemical, photometry, scintigraphy, electronic methods, UV, visible light or infra-red spectroscopy, enzymatic methods, or any combination thereof.

14. A kit comprising the isolated polynucleotide substrate of claim 1 and a catalytic nucleic acid enzyme capable of catalytically modifying the polynucleotide substrate.

15. An assembly comprising a solid support bound to a polynucleotide substrate of claim 1.

* * * * *

SEQUENCE LISTING

```
<160> NUMBER OF SEQ ID NOS: 190

<210> SEQ ID NO 1
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 1
caaacgagtc ctggccttgt ctacaacgag aggaaacctt                              40

<210> SEQ ID NO 2
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 2
tgcccaggga ggctagctgt ggagacggat tacaccttc                               39

<210> SEQ ID NO 3
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 3
caaacgagtc ctggccttgt ctacaacgag gttgtgctg                               39

<210> SEQ ID NO 4
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 4
cggttggtga ggctagctgt ggagacggat tacaccttc                               39

<210> SEQ ID NO 5
<211> LENGTH: 39
<212> TYPE: DNA
<213> ORGANISM: Artificial Sequence
```

<220> FEATURE:
<223> OTHER INFORMATION: Synthetic oligonucleotide

<400> SEQUENCE: 5
caaacgagtc ctggccttgt ctacaacgag aggcgtgat        39

<210> SEQ ID NO 6
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 6
ctgggaggaa ggctagctgt ggagacggat tacaccttc        39

<210> SEQ ID NO 7
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 7
caaacgagtc ctggccttgt ctacaacgag tgccatgtta a        41

<210> SEQ ID NO 8
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 8
tatcacagcc aaggctagct gtggagacgg attacacctt c        41

<210> SEQ ID NO 9
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 9
caaacgagtc ctggccttgt ctacaacgag aggagacctg        40

<210> SEQ ID NO 10
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 10
tcactatagg gaggctagct gtggagacgg attacacctt c        41

<210> SEQ ID NO 11
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 11
caaacgagtc ctggccttgt ctacaacgag ggacccgt        38

```
<210> SEQ ID NO 12
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 12
ttccaaagga gaggctagct gtggagacgg attacacctt c                41

<210> SEQ ID NO 13
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 13
caaacgagtc ctggccttgt ctacaacgaa ggtgcggt                   38

<210> SEQ ID NO 14
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 14
gagctgggga ggctagctgt ggagacggat tacaccttc                  39

<210> SEQ ID NO 15
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 15
caaacgagtc ctggccttgt ctacaacgag agccaagttt a               41

<210> SEQ ID NO 16
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 16
caaacgagtc ctggccttgt ctacaacgag aggtgcggt                  39

<210> SEQ ID NO 17
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 17
caaacgagtc ctggccttgt ctacaacgag tggttggc                   38

<210> SEQ ID NO 18
<211> LENGTH: 40
<212> TYPE: DNA
<213> ORGANISM: Artificial Sequence
<220> FEATURE:
<223> OTHER INFORMATION: Synthetic oligonucleotide
```

```
<400> SEQUENCE: 18
gtcgtgttgg aggctagctg tggagacgga ttacaccttc                           40

<210> SEQ ID NO 19

<400> SEQUENCE: 19

000

<210> SEQ ID NO 20

<400> SEQUENCE: 20

000

<210> SEQ ID NO 21
<211> LENGTH: 22
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions twelve
      and thirteen
<220> FEATURE:
<223> OTHER INFORMATION: Description of Artificial Sequence: synthetic
      oligonucleotide

<400> SEQUENCE: 21
aaggtttcct cguccctggg ca                                              22

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 22
cagcacaacc gucaccaacc g                                               21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 23
atcacgcctc gutcctccca g                                               21

<210> SEQ ID NO 24
<211> LENGTH: 25
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions
      thirteen and fourteen
```

```
<220> FEATURE:
<223> OTHER INFORMATION: Description of Artificial Sequence: synthetic
      oligonucleotide

<400> SEQUENCE: 24
ttaacatggc acgutggctg tgata                                            25

<210> SEQ ID NO 25
<211> LENGTH: 24
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions twelve
      and thirteen
<220> FEATURE:
<223> OTHER INFORMATION: Description of Artificial Sequence: synthetic
      oligonucleotide

<400> SEQUENCE: 25
caggtctcct cgucsctata gtga                                             24

<210> SEQ ID NO 26
<211> LENGTH: 22
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions ten
      and eleven
<220> FEATURE:
<223> OTHER INFORMATION: Description of Artificial Sequence: synthetic
      oligonucleotide

<400> SEQUENCE: 26
acgggtcccg uctcctttgg aa                                               22

<210> SEQ ID NO 27
<211> LENGTH: 20
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions ten
      and eleven
<220> FEATURE:
<223> OTHER INFORMATION: Description of Artificial Sequence: synthetic
      oligonucleotide

<400> SEQUENCE: 27
accgcacctg uccccagctc                                                  20

<210> SEQ ID NO 28
<211> LENGTH: 25
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions
      thirteen and fourteen
<220> FEATURE:
<223> OTHER INFORMATION: Description of Artificial Sequence: synthetic
      oligonucleotide

<400> SEQUENCE: 28
taaacttggc tcgutggctg tgata                                            25

<210> SEQ ID NO 29
<211> LENGTH: 21
```

```
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 29
accgcacctc gucccagct c                                                  21

<210> SEQ ID NO 30
<211> LENGTH: 21
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions ten
      and eleven
<220> FEATURE:
<223> OTHER INFORMATION: Description of Artificial Sequence: synthetic
      oligonucleotide

<400> SEQUENCE: 30
gccaaccacg uccaacacga c                                                 21

<210> SEQ ID NO 31
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 31
cccattctat catcaacggg ta                                                22

<210> SEQ ID NO 32
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 32
gcccactgtg gtcctggtg                                                    19

<210> SEQ ID NO 33
<211> LENGTH: 22
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 33
cctcctccct gucctcctc ct                                                 22

<210> SEQ ID NO 34
<211> LENGTH: 39
<212> TYPE: DNA
<213> ORGANISM: Artificial Sequence
<220> FEATURE:
<223> OTHER INFORMATION: Synthetic oligonucleotide
```

<400> SEQUENCE: 34
ggaatatgga aggagactgt cacaacgaga ggaaacctt                                39

<210> SEQ ID NO 35
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 35
tgcccaggga ggctagctcc tctgactgga aaacagact                                39

<210> SEQ ID NO 36
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 36
ggaatatgga aggagactgt cacaacgagg ttgtgctg                                 38

<210> SEQ ID NO 37
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 37
cggttggtga ggctagctcc tctgactgga aaacagact                                39

<210> SEQ ID NO 38
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 38
ggaatatgga aggagactgt cacaacgaga ggcgtgat                                 38

<210> SEQ ID NO 39
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 39
ctgggaggaa ggctagctcc tctgactgga aaacagact                                39

<210> SEQ ID NO 40
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 40
ggaatatgga aggagactgt cacaacgaga ggagacctg                                39

<210> SEQ ID NO 41

```
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 41
tcactatagg gaggctagct cctctgactg gaaaacagac t                      41

<210> SEQ ID NO 42
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 42
ggaatatgga aggagactgt cacaacgagg gacccgt                           37

<210> SEQ ID NO 43
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 43
ttccaaagga gaggctagct cctctgactg gaaaacagac t                      41

<210> SEQ ID NO 44
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 44
ggaatatgga aggagactgt cacaacgaag gtgcggt                           37

<210> SEQ ID NO 45
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 45
gagctgggga ggctagctcc tctgactgga aaacagact                         39

<210> SEQ ID NO 46
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 46
ggaatatgga aggagactgt cacaacgaga ggtgcggt                          38

<210> SEQ ID NO 47
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 47
```
ggaatatgga aggagactgt cacaacgaag ggaggagg                              38

<210> SEQ ID NO 48
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 48
ggaatatgga aggagactgt cacaacgagt ggttggc                               37

<210> SEQ ID NO 49
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 49
gtcgtgttgg aggctagctc ctctgactgg aaaacagact                            40

<210> SEQ ID NO 50
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 50
ggaatatgga aggagactgt cacaacgagg ggtcgag                               37

<210> SEQ ID NO 51
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 51
tggcgtggag aggctagctc ctctgactgg aaaacagact                            40

<210> SEQ ID NO 52
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 52
ggaatatgga aggagactgt cacaacgaga ggtcgaga                              38

<210> SEQ ID NO 53

<400> SEQUENCE: 53

000

<210> SEQ ID NO 54

<400> SEQUENCE: 54

000

<210> SEQ ID NO 55

-continued

<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 55
ctgggaggag aggctagctc ctctgactgg aaaacagact                40

<210> SEQ ID NO 56
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 56
ggaatatgga aggagactgt cacaacgagg ggacgcca                 38

<210> SEQ ID NO 57
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 57
cacgagggga ggctagctcc tctgactgga aaacagact                39

<210> SEQ ID NO 58
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 58
ggaatatgga aggagactgt cacaacgagg ggagtgat                 38

<210> SEQ ID NO 59
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 59
ctgggagggg aggctagctc ctctgactgg aaaacagact                40

<210> SEQ ID NO 60
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 60
ggaatatgga aggagactgt cacaacgaga ggagggtca                39

<210> SEQ ID NO 61
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 61
tagtggggag aggctagctc ctctgactgg aaaacagact         40

<210> SEQ ID NO 62
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 62
ggaatatgga aggagactgt cacaacgaga gggaggag           38

<210> SEQ ID NO 63
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 63
aggaggaggg aggctagctc ctctgactgg aaaacagact         40

<210> SEQ ID NO 64
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 64
ggaatatgga aggagactgt cacaacgagg ggagagga           38

<210> SEQ ID NO 65
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 65
ggttgaaggg gaggctagct cctctgactg gaaaacagac t        41

<210> SEQ ID NO 66
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 66
ggaatatgga aggagactgt cacaacgaga gggcggtt           38

<210> SEQ ID NO 67
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 67
ggttcacggg aggctagctc ctctgactgg aaaacagact         40

<210> SEQ ID NO 68
<211> LENGTH: 40
<212> TYPE: DNA

```
<213> ORGANISM: Artificial Sequence
<220> FEATURE:
<223> OTHER INFORMATION: Synthetic oligonucleotide

<400> SEQUENCE: 68
tggacgaggg aggctagctc ctctgactgg aaaacagact                           40

<210> SEQ ID NO 69
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 69
ggaatatgga aggagactgt cacaacgagg ggagcgga                             38

<210> SEQ ID NO 70
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 70
gttgcagggg aggctagctc ctctgactgg aaaacagact                           40

<210> SEQ ID NO 71
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 71
ggaatatgga aggagactgt cacaacgaga gggtcgag                             38

<210> SEQ ID NO 72
<211> LENGTH: 22
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 72
tgccaaccac guccaacacg ac                                              22

<210> SEQ ID NO 73
<211> LENGTH: 21
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions ten
      and eleven
<220> FEATURE:
<223> OTHER INFORMATION: Description of Artificial Sequence: synthetic
      oligonucleotide

<400> SEQUENCE: 73
ctcgaccccg uctccacgcc a                                               21
```

<210> SEQ ID NO 74
<211> LENGTH: 22
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 74
tctcgacctc guctccacgc ca                                            22

<210> SEQ ID NO 75
<211> LENGTH: 22
<212> TYPE: DNA
<213> ORGANISM: Artificial Sequence
<220> FEATURE:
<223> OTHER INFORMATION: description of combined dna/rna sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 75
atcacgcctc guctcctccc ag                                            22

<210> SEQ ID NO 76
<211> LENGTH: 21
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 76
tggcgtcccc gucccctcgt g                                             21

<210> SEQ ID NO 77
<211> LENGTH: 22
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 77
atcactcccc gucccctccc ag                                            22

<210> SEQ ID NO 78
<211> LENGTH: 23
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions twelve
      and thirteen
<220> FEATURE:
<223> OTHER INFORMATION: Description of Artificial Sequence: synthetic
      oligonucleotide

<400> SEQUENCE: 78
tgaccctcct cguctcccca cta                                    23

<210> SEQ ID NO 79
<211> LENGTH: 22
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 79
ctcctccctc guccctcctc ct                                     22

<210> SEQ ID NO 80
<211> LENGTH: 23
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 80
tcctctcccc guccccttca acc                                    23

<210> SEQ ID NO 81
<211> LENGTH: 22
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 81
aaccgccctc guccgtgaa cc                                      22

<210> SEQ ID NO 82
<211> LENGTH: 22
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 82
ctcctccctc guccctcgtc ca                                     22

<210> SEQ ID NO 83
<211> LENGTH: 22
<212> TYPE: DNA
<213> ORGANISM: Artificial Sequence
<220> FEATURE:

```
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 83
tccgctcccc gucccctgca ac                                              22

<210> SEQ ID NO 84
<211> LENGTH: 22
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 84
accgcacctc guctcctccc ag                                              22

<210> SEQ ID NO 85
<211> LENGTH: 22
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 85
accgcacctc guccctccc ag                                               22

<210> SEQ ID NO 86
<211> LENGTH: 21
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 86
atcacgcctc gucccagct c                                                21

<210> SEQ ID NO 87
<211> LENGTH: 21
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 87
atcactcccc gucccagct c                                                21
```

<210> SEQ ID NO 88
<211> LENGTH: 21
<212> TYPE: DNA
<213> ORGANISM: Artificial Sequence
<220> FEATURE:
<223> OTHER INFORMATION: Description of Combined DNA/RNA Sequence: synthetic oligonucleotide with ribonucleotides at positions eleven and twelve
<220> FEATURE:
<223> OTHER INFORMATION: Description of Artificial Sequence: synthetic oligonucleotide

<400> SEQUENCE: 88
ctcctccctc gucccagct c                                              21

<210> SEQ ID NO 89
<211> LENGTH: 22
<212> TYPE: DNA
<213> ORGANISM: Artificial Sequence
<220> FEATURE:
<223> OTHER INFORMATION: Description of Combined DNA/RNA Sequence: synthetic oligonucleotide with ribonucleotides at positions eleven and twelve
<220> FEATURE:
<223> OTHER INFORMATION: Description of Artificial Sequence: synthetic oligonucleotide

<400> SEQUENCE: 89
accgcacctc guccctcctc ct                                            22

<210> SEQ ID NO 90
<211> LENGTH: 22
<212> TYPE: DNA
<213> ORGANISM: Artificial Sequence
<220> FEATURE:
<223> OTHER INFORMATION: Description of Combined DNA/RNA Sequence: synthetic oligonucleotide with ribonucleotides at positions eleven and twelve
<220> FEATURE:
<223> OTHER INFORMATION: Description of Artificial Sequence: synthetic oligonucleotide

<400> SEQUENCE: 90
ctcgaccctc guccctcgtc ca                                            22

<210> SEQ ID NO 91
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 91
gctaaaacaa taactcagaa cttacg                                        26

<210> SEQ ID NO 92
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 92
cagctttctg aggttaccat ccta                                          24

<210> SEQ ID NO 93
<211> LENGTH: 40
<212> TYPE: DNA

<213> ORGANISM: Artificial Sequence
<220> FEATURE:
<223> OTHER INFORMATION: Synthetic oligonucleotide

<400> SEQUENCE: 93
ggaatatgga aggagactgt cacaacgaga gccaagttta                    40

<210> SEQ ID NO 94
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 94
tatcacagcc aaggctagct cctctgactg gaaaacagac t                  41

<210> SEQ ID NO 95
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 95
agtctgtttt ccagtcagag gacagtctc cttccatatt cc                  42

<210> SEQ ID NO 96
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 96
gggaagagga gcattgagga acaacgaggt tgtgctg                       37

<210> SEQ ID NO 97
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 97
cggttggtga ggctagctcc gtgttcaaga ggaagc                        36

<210> SEQ ID NO 98
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 98
gggaagagga gcattgagga acaacgaggg gtcgag                        36

<210> SEQ ID NO 99
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 99
tggcgtggag aggctagctc cgtgttcaag aggaagc                       37

<210> SEQ ID NO 100
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 100
gacggaacag ctttgaggtg acaacgagag gcgtgat                    37

<210> SEQ ID NO 101
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 101
ctgggaggaa ggctagctcg tgtttgtgcc tgtcctgg                   38

<210> SEQ ID NO 102

<400> SEQUENCE: 102

000

<210> SEQ ID NO 103
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 103
ctgggaggag aggctagctc gtgtttgtgc ctgtcctgg                  39

<210> SEQ ID NO 104
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 104
gacggaacag ctttgaggtg acaacgaggg gagtgat                    37

<210> SEQ ID NO 105
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 105
ctgggagggg aggctagctc gtgtttgtgc ctgtcctgg                  39

<210> SEQ ID NO 106
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 106
gacggaacag ctttgaggtg acaacgaggg gagagga                    37

<210> SEQ ID NO 107
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 107
ggttgaaggg gaggctagct cgtgtttgtg cctgtcctgg          40

<210> SEQ ID NO 108
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 108
attcaggttt actcacgtca tcacaacgag tggttggc            38

<210> SEQ ID NO 109
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 109
gtcgtgttgg aggctagctc agcagagaat ggaaagtcaa a        41

<210> SEQ ID NO 110
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 110
attcaggttt actcacgtca tcacaacgag gggtcgag            38

<210> SEQ ID NO 111
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 111
tggcgtggag aggctagctc agcagagaat ggaaagtcaa a        41

<210> SEQ ID NO 112
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 112
attcaggttt actcacgtca tcacaacgag gggagagga           39

<210> SEQ ID NO 113
<211> LENGTH: 42
<212> TYPE: DNA
<213> ORGANISM: Artificial Sequence
<220> FEATURE:

<223> OTHER INFORMATION: Synthetic oligonucleotide

<400> SEQUENCE: 113
ggttgaaggg gaggctagct cagcagagaa tggaaagtca aa    42

<210> SEQ ID NO 114
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 114
gccatgtctg gtaacggcaa acaacgagag ccaagttta    39

<210> SEQ ID NO 115
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 115
tatcacagcc aaggctagct tgcggctgca acggcggtg    39

<210> SEQ ID NO 116
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 116
gccatgtctg gtaacggcaa acaacgagag gagggtca    38

<210> SEQ ID NO 117
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 117
tagtggggag aggctagctt gcggctgcaa cggcggtg    38

<210> SEQ ID NO 118
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 118
ttgacaaata cacagaggtc acaacgagag gtgcggt    37

<210> SEQ ID NO 119
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 119
gagctgggga ggctagctct caagacccac ggactcct    38

```
<210> SEQ ID NO 120
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 120
aattgacaaa tacacagagg tcacaacgag agggcggtt                              39

<210> SEQ ID NO 121
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 121
ggttcacggg aggctagctc tcaagaccca cggactcct                              39

<210> SEQ ID NO 122
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 122
aattgacaaa tacacagagg tcacaacgag agggaggag                              39

<210> SEQ ID NO 123
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 123
gctaatcttt tcccgatatt cctcag                                           26

<210> SEQ ID NO 124
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 124
cagcccagac acatagcaat tcag                                             24

<210> SEQ ID NO 125
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 125
ctaacttact gcctcttgct tctc                                             24

<210> SEQ ID NO 126
<211> LENGTH: 22
<212> TYPE: DNA
<213> ORGANISM: Artificial Sequence
<220> FEATURE:
<223> OTHER INFORMATION: Synthetic oligonucleotide
```

```
<400> SEQUENCE: 126
cagctctgtg cgccggtctc tc                                              22

<210> SEQ ID NO 127
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 127
ctaaaccgga agaagaaaca gctca                                           25

<210> SEQ ID NO 128
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 128
caggaggaat taacagtctt tattgg                                          26

<210> SEQ ID NO 129
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 129
ctaacctcat gacgctgcgg aa                                              22

<210> SEQ ID NO 130
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 130
cagatatgga gtagggtcac cca                                             23

<210> SEQ ID NO 131
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 131
ctaaacccac acacagccta ctttc                                           25

<210> SEQ ID NO 132
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 132
cagagcccaa agtgtgctgg tca                                             23

<210> SEQ ID NO 133
<211> LENGTH: 36
```

```
<212> TYPE: DNA
<213> ORGANISM: Artificial Sequence
<220> FEATURE:
<223> OTHER INFORMATION: Synthetic oligonucleotide

<400> SEQUENCE: 133
tgcccaggga ggctagctac aacgagagga aacctt                              36

<210> SEQ ID NO 134
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 134
cggttggtga ggctagctac aacgaggttg tgctg                               35

<210> SEQ ID NO 135
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 135
ctgggaggaa ggctagctac aacgagaggc gtgat                               35

<210> SEQ ID NO 136
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 136
tcactatagg gaggctagct acaacgagag gagacctg                            38

<210> SEQ ID NO 137
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 137
ttccaaagga gaggctagct acaacgaggg acccgt                              36

<210> SEQ ID NO 138
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 138
tatcacagcc aaggctagct acaacgagag ccaagttta                           39

<210> SEQ ID NO 139
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 139
```
ggagctgggg aggctagcta caacgagagg tgcggtg        37

<210> SEQ ID NO 140
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 140
gtcgtgttgg aggctagcta caacgagtgg ttggc          35

<210> SEQ ID NO 141
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 141
gtggcgtgga gaggctagct acaacgaggg gtcgagg        37

<210> SEQ ID NO 142
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 142
gctgggagga gaggctagct acaacgagag gcgtgatg       38

<210> SEQ ID NO 143
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 143
gcacgagggg aggctagcta caacgagggg acgccag        37

<210> SEQ ID NO 144
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 144
gctgggaggg gaggctagct acaacgaggg gagtgatg       38

<210> SEQ ID NO 145
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 145
gtagtgggga gaggctagct acaacgagag gagggtcag      39

<210> SEQ ID NO 146
<211> LENGTH: 38
<212> TYPE: DNA
<213> ORGANISM: Artificial Sequence

```
<220> FEATURE:
<223> OTHER INFORMATION: Synthetic oligonucleotide

<400> SEQUENCE: 146
gaggaggagg gaggctagct acaacgagag ggaggagg                                38

<210> SEQ ID NO 147
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 147
gggttgaagg ggaggctagc tacaacgagg ggagaggag                               39

<210> SEQ ID NO 148
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 148
gggttcacgg gaggctagct acaacgagag ggcggttgg                               39

<210> SEQ ID NO 149
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 149
gctgggagga gaggctagct acaacgagag gtgcggtg                                38

<210> SEQ ID NO 150
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 150
gctgggaggg gaggctagct acaacgagag gtgcggtg                                38

<210> SEQ ID NO 151
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 151
ggagctgggg aggctagcta caacgagagg cgtgatg                                 37

<210> SEQ ID NO 152
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 152
ggagctgggg aggctagcta caacgagggg agtgatg                                 37
```

<210> SEQ ID NO 153
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 153
ggagctgggg aggctagcta caacgagagg gaggagg    37

<210> SEQ ID NO 154
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 154
gaggaggagg gaggctagct acaacgagag gtgcggtg    38

<210> SEQ ID NO 155
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 155
aattgacaaa tacacagagg tcacaacgag aggagacctg    40

<210> SEQ ID NO 156
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 156
tcactatagg gaggctagct ctcaagaccc acggactcct    40

<210> SEQ ID NO 157
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 157
aattgacaaa tacacagagg tcacaacgag aggcgtgat    39

<210> SEQ ID NO 158
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 158
ctgggaggag aggctagctc tcaagaccca cggactcct    39

<210> SEQ ID NO 159
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 159
aattgacaaa tacacagagg tcacaacgag gggagtgat                                39

<210> SEQ ID NO 160
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 160
ctgggagggg aggctagctc tcaagaccca cggactcct                                39

<210> SEQ ID NO 161
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 161
accggaagaa gaaacagctc a                                                  21

<210> SEQ ID NO 162
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 162
gaggaattaa cagtctttat tgg                                                23

<210> SEQ ID NO 163
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 163
ctgggaggaa ggctagctct caagacccac ggactcct                                38

<210> SEQ ID NO 164
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 164
gacggaacag ctttgaggtg acaacgagtg cgccatg                                 37

<210> SEQ ID NO 165
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 165
tacttctccc aaggctagct cgtgtttgtg cctgtcctgg                              40

<210> SEQ ID NO 166

```
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 166
ctgaatagaa atagtgatag atcacaacga gtgccatgtt aa                      42

<210> SEQ ID NO 167
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 167
tatcacagcc aaggctagct cattcctatg actgtagatt tta                     43

<210> SEQ ID NO 168
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 168
ctgaatagaa atagtgatag atcacaacga gaggtgcggt                         40

<210> SEQ ID NO 169
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 169
gagctgggga ggctagctca ttcctatgac tgtagatttt a                       41

<210> SEQ ID NO 170

<400> SEQUENCE: 170

000

<210> SEQ ID NO 171
<211> LENGTH: 23
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eleven
      and twelve
<220> FEATURE:
<223> OTHER INFORMATION: Description of Artificial Sequence: synthetic
      oligonucleotide

<400> SEQUENCE: 171
catggcgcac gutgggagaa gta                                           23

<210> SEQ ID NO 172
<211> LENGTH: 16
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions eight
      and nine
```

```
<220> FEATURE:
<223> OTHER INFORMATION: Description of Artificial Sequence: synthetic
      oligonucleotide

<400> SEQUENCE: 172
gcacctcguc cccagc                                                        16

<210> SEQ ID NO 173
<211> LENGTH: 18
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions nine
      and ten
<220> FEATURE:
<223> OTHER INFORMATION: Description of Artificial Sequence: synthetic
      oligonucleotide

<400> SEQUENCE: 173
cgcacctcgu ccccagct                                                      18

<210> SEQ ID NO 174
<211> LENGTH: 23
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions twelve
      and thirteen
<220> FEATURE:
<223> OTHER INFORMATION: Description of Artificial Sequence: synthetic
      oligonucleotide

<400> SEQUENCE: 174
aaccgcacct cgucccagc tca                                                 23

<210> SEQ ID NO 175
<211> LENGTH: 23
<212> TYPE: DNA
<213> ORGANISM: Artificial Sequence
<220> FEATURE:
<223> OTHER INFORMATION: Description of Combined DNA/RNA Sequence:
      synthetic oligonucleotide with ribonucleotides at positions twelve
      and thirteen
<220> FEATURE:
<223> OTHER INFORMATION: Description of Artificial Sequence: synthetic
      oligonucleotide

<400> SEQUENCE: 175
caccgcacct cgucccagc tcc                                                 23

<210> SEQ ID NO 176
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 176
ctaactttgc tgacctgctg gatta                                              25

<210> SEQ ID NO 177
<211> LENGTH: 25
<212> TYPE: DNA
<213> ORGANISM: Artificial Sequence
<220> FEATURE:
<223> OTHER INFORMATION: Synthetic oligonucleotide
```

```
<400> SEQUENCE: 177
cagcaatagc tcttcagtct gataa                                          25

<210> SEQ ID NO 178

<400> SEQUENCE: 178

000

<210> SEQ ID NO 179
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 179
ggaatatgga aggagactgt cacaacgaga ggtgcg                              36

<210> SEQ ID NO 180
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 180
agctggggag gctagctcct ctgactggaa aacagact                            38

<210> SEQ ID NO 181
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 181
ggaatatgga aggagactgt cacaacgaga ggtgc                               35

<210> SEQ ID NO 182
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 182
gctggggagg ctagctcctc tgactggaaa acagact                             37

<210> SEQ ID NO 183
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 183
ggaatatgga aggagactgt cacaacgaga ggtgcggtt                           39

<210> SEQ ID NO 184
<211> LENGTH: 40
<212> TYPE: DNA
<213> ORGANISM: Artificial Sequence
<220> FEATURE:
<223> OTHER INFORMATION: Synthetic oligonucleotide
```

<400> SEQUENCE: 184
tgagctgggg aggctagctc ctctgactgg aaaacagact            40

<210> SEQ ID NO 185
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 185
ggaatatgga aggagactgt cacaacgaga ggtgcggtg            39

<210> SEQ ID NO 186
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 186
ggagctgggg aggctagctc ctctgactgg aaaacagact            40

<210> SEQ ID NO 187
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 187
aacaataact cagaacttac g            21

<210> SEQ ID NO 188
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 188
ctttctgagg ttaccatcct a            21

<210> SEQ ID NO 189
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is any number of a, c, g, t or u
<220> FEATURE:
<221> NAME/KEY: misc_feature
<222> LOCATION: (3)..(5)
<223> OTHER INFORMATION: n is a, c, g, t or u
<220> FEATURE:
<221> NAME/KEY: misc_feature
<222> LOCATION: (9)..(11)
<223> OTHER INFORMATION: n is a, c, g, t or u
<220> FEATURE:
<221> NAME/KEY: misc_feature
<222> LOCATION: (12)..(12)
<223> OTHER INFORMATION: w is a, t, or u
<220> FEATURE:
<221> NAME/KEY: misc_feature
<222> LOCATION: (15)..(15)
<223> OTHER INFORMATION: r is a, g , or aa

```
<220> FEATURE:
<221> NAME/KEY: misc_feature
<222> LOCATION: (16)..(16)
<223> OTHER INFORMATION: n is any number of a, c, g, t or u

<400> SEQUENCE: 189
ntnnnagcnn nwcgrn                                                    16

<210> SEQ ID NO 190
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, t, g, or u
<220> FEATURE:
<221> NAME/KEY: misc_feature
<222> LOCATION: (4)..(4)
<223> OTHER INFORMATION: m is a or c
<220> FEATURE:
<221> NAME/KEY: misc_feature
<222> LOCATION: (6)..(6)
<223> OTHER INFORMATION: m is a or c
<220> FEATURE:
<221> NAME/KEY: misc_feature
<222> LOCATION: (8)..(8)
<223> OTHER INFORMATION: h is a, c, t, or u
<220> FEATURE:
<221> NAME/KEY: misc_feature
<222> LOCATION: (9)..(9)
<223> OTHER INFORMATION: n is a, c, t, g or u
<220> FEATURE:
<221> NAME/KEY: misc_feature
<222> LOCATION: (10)..(10)
<223> OTHER INFORMATION: d is a, t, g or u
<220> FEATURE:
<221> NAME/KEY: misc_feature
<222> LOCATION: (11)..(13)
<223> OTHER INFORMATION: n is a, c, t, g or u
<220> FEATURE:
<221> NAME/KEY: misc_feature
<222> LOCATION: (14)..(14)
<223> OTHER INFORMATION: m is a or c
<220> FEATURE:
<221> NAME/KEY: misc_feature
<222> LOCATION: (16)..(16)
<223> OTHER INFORMATION: d is g, a, t or u
<220> FEATURE:
<221> NAME/KEY: misc_feature
<222> LOCATION: (17)..(17)
<223> OTHER INFORMATION: n is a, c, t, g, or u

<400> SEQUENCE: 190
nggmtmghnd nnnmgdn                                                   17
```